(12) United States Patent
Jiang et al.

(10) Patent No.: US 7,405,300 B2
(45) Date of Patent: Jul. 29, 2008

(54) SUBSTITUTED INDOLES AS INHIBITORS OF POLY (ADP-RIBOSE) POLYMERASE (PARP)

(75) Inventors: John Z. Jiang, Hillsborough, NJ (US); Jack Roger Koehl, Whitehouse Station, NJ (US); Shujaath Mehdi, Manville, NJ (US); Neil David Moorcroft, Bloomsbury, NJ (US); Kwon Yon Musick, Raritan, NJ (US); Philip Marvin Weintraub, Warren, NJ (US); Paul Robert Eastwood, Barcelona (ES)

(73) Assignee: Aventis Pharmaveuticals Inc., Bridgewater, NJ (US)

( * ) Notice: Subject to any disclaimer, the term of this patent is extended or adjusted under 35 U.S.C. 154(b) by 550 days.

(21) Appl. No.: 10/933,098

(22) Filed: Sep. 1, 2004

(65) Prior Publication Data

US 2005/0054631 A1 Mar. 10, 2005

Related U.S. Application Data

(60) Provisional application No. 60/500,039, filed on Sep. 4, 2003.

(51) Int. Cl.
C07D 403/04 (2006.01)
C07D 209/04 (2006.01)

(52) U.S. Cl. .................. 544/373; 548/465; 548/466; 548/467; 548/483

(58) Field of Classification Search ............... 540/554, 540/602; 544/373; 548/465, 466, 467, 483
See application file for complete search history.

(56) References Cited

U.S. PATENT DOCUMENTS

| 4,148,895 | A | 4/1979 | Lattrell et al. |
| 6,303,629 | B1 | 10/2001 | Kun |
| 7,169,925 | B2 * | 1/2007 | Merriman et al. ............ 544/333 |

FOREIGN PATENT DOCUMENTS

| DE | 2707268 | 8/1978 |
| WO | WO 99/11628 | 3/1999 |
| WO | WO 01/85687 | 11/2001 |

OTHER PUBLICATIONS

Aldo Andreani et al., Nonsteroidal Antiinflammatory Agents. 2. Synthesis and Biological Activity of 2-Chloroindolecarboxylic Acids, Journal of Medicinal Chemistry, (1977, pp. 1344-1346, vol. 20-Issue 10).

Antonella Capperucci et al., Hexamethyldisilathiane: Its Use in the Conversion Of Aromatic And Heteroaromatic Azides to Amines, J. Org. Chem. (1995, pp. 2254-2256, vol. 60).

Dana Ferraris, et al et al., Design And Synthesis of Poly ADP-Ribose Polymerase-1 Inhibitors. 2. Biological Evaluation of Aza-5[H]-Phenanthridin-6-ones as Potent, Aqueous-Soluble Compounds For The Treatment Of Ischemic Injuries, Journal Med. Chem. (2003, pp. 3138-3151, vol. 46).

Pauline C. Ting et al., Substituted 1,3-Dihydro-2H-Pyrrolo[2,3-b] Pyridin-2-Ones As Potential Antiinflammatory Agents, J. Med. Chem. (1990, pp. 2697-2706, vol. 33).

Shigenobu Okuda et al., 7-Azaindole V. Investigations of Alternative Syntheses of the Ring System, J. Am. Chem. Soc. ( 1959, pp. 740-743, vol. 81).

Kadriye Benkil et al., Synthesis And Antimicrobial Activities Of Some Imidazole Substituted Indoles, Indian J. Chem., Sect B: Org. Chem. incl. Med. Chem. (2004, 43B (1), 174-179); Chem. Abst. 2004:84341 (Chem abstract only attached—2 pages).

Mark R. Player et al., 1,3-Oxazino[4,5-b]Indole-2,4-(1H,9H)-Diones And 5,6-Dimethylpyrrolo-[2,3-d]-1,3-Oxazin-2,4-(1H,7H)-Diones As Serine Protease Inhibitors, Bioorganic & Medicinal Chemistry Letters (1994, pp. 949-954, vol. 4 No. 7).

Mark R. Player et al., Synthesis Of 1,3-Disubstituted-2-Amino-5-Hydroxyindoles By Reductive Aromatization, J. Heterocyclic Chem (1993, pp. 125-127, vol. 30).

* cited by examiner

*Primary Examiner*—James O. Wilson
*Assistant Examiner*—Ebenezer Sackey
(74) *Attorney, Agent, or Firm*—Balaram Gupta

(57) ABSTRACT

The present invention relates to a series of substituted indole derivatives of the formula I:

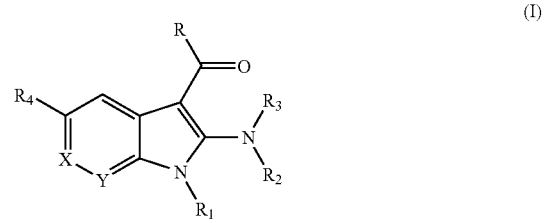

(I)

wherein R, $R_1$, $R_2$, $R_3$, $R_4$, X and Y are as defined herein. This invention also relates to methods of making these compounds. The compounds of this invention are inhibitors of poly(adenosine 5'-diphosphate ribose) polymerase (PARP) and are therefore useful as pharmaceutical agents, especially in the treatment and/or prevention of a variety of diseases, including diseases associated with the central nervous system and cardiovascular disorders.

9 Claims, No Drawings

SUBSTITUTED INDOLES AS INHIBITORS OF POLY (ADP-RIBOSE) POLYMERASE (PARP)

This application claims the benefit of U.S. Provisional Application No. 60/500,039, filed Sep. 4, 2003.

BACKGROUND OF THE INVENTION

1. Field of the Invention

The present invention relates to a series of substituted indole compounds. More specifically, the present invention relates to a novel series of N,2,3-substituted indole derivatives. This invention also relates to methods of making these compounds. The compounds of this invention are inhibitors of poly(adenosine 5'-diphosphate ribose) polymerase (PARP) and are, therefore, useful as pharmaceutical agents, especially in the treatment and/or prevention of a variety of diseases including diseases associated with the central nervous system and cardiovascular disorders.

2. Description of the Art

Poly(adenosine 5'-diphosphate ribose) polymerase [poly (ADP-ribose) polymerase, PARP, EC 2.4.2.30] also known as poly(ADP-ribose) synthetase (PARS) is a chromatin-bound nuclear enzyme of eukaryotic cells, present at about $2 \times 10^5$ molecules/nucleus. The high degree of evolutionary conservation of PARP in multicellular organisms can be taken as an indication of the physiological importance of poly(ADP-ribosyl)ation. Activated by DNA strand breaks PARP transfers ADP-ribose units from $NAD^+$ to nuclear proteins including histones and PARP itself. This reaction generates poly(ADP) ribose and nicotinamide, with the latter being a negative feedback inhibitor of PARP. The role of $NAD^+$ in this sequence is distinct from its role as a redox cofactor in other enzymatic processes. The poly(ADP-ribose) thus formed typically contains in the order of 200 ribose units having linear and branched connections with one branch approximately every 25 units of ADP-ribose. The links are by $\alpha$-(1"-2')ribosyl-glycosic bonds. Because of the negative charges of ADP-ribose polymers, poly(ADP-ribosylated)proteins lose their affinity for DNA and are, therefore, inactivated. Poly (ADP-ribosyl)ation is an immediate, covalent, but transient post-translational modification. Poly(ADP-ribose) is in a dynamic state, its rapid synthesis being followed by a degradation catalyzed by the enzyme poly(ADP) glycohydrolase (PARG). Thus, PARP and other modified proteins are returned to their native state. For reviews on PARP see: Liadet. L., "Poly(adenosine 5'-diphosphate) ribose polymerase activation as a cause of metabolic dysfunction in critical illness"; Current Opinions Clin. Nutrition Metabolic Care, 5, 175-184 (2002). Burkle, A., "Physiology and pathophysiology of poly(ADP-ribosyl)ation"; BioEssays, 23, 795-806 (2001). Hageman, G. J. and Stierum, R. H., "Niacin, Poly (ADP-ribose) polymerse-1 and genomic stability"; Mutation Res., 475, 45-56 (2001). Smith, S., "The world according to PARP"; Trends Biochem Sci., 26, 174-179 (2001). Tong, W.-M. et al., Poly(ADP-ribose) polymerase: a guardian angel protecting the genome and suppressing tumorigenisis"; Biochim. Biophys. Acta, 1552, 27-37 (2001).

In cerebral ischemia, calcium influx into neurons causes the activation of nitric oxide synthase, leading to production of nitric oxide and subsequently the reactive radical peroxynitrite. Peroxynitrite causes extensive damage to DNA and results in uncontrolled activation of PARP. Cellular NAD and ATP are quickly used up and the cell dies a necrotic death due to loss of the source of cellular energy. DNA is similarly damaged by peroxynitrite in myocardial ischemia and in inflammation.

Several studies with PARP −/− animals and with a variety of inhibitors support the role of PARP in the pathophysiology of a number of disease models. In a stroke model, for example, the infarct size in PARP-deficient animals is 80% smaller compared to control PARP +/+ animals. See, for example, Eliasson, M. J. L. et al., "Poly(ADP-ribose)polymerase gene disruption renders mice resistant to cerebral ischemia"; Nature Med., 3, 1089 (1997). In addition, many studies using various PARP inhibitors (e.g. 3-aminobenzamide, GPI 6150, PJ-34 and nicotinamide) have shown reduction in stroke-induced infarction volume and reduced behavioral deficits in post-stroke treatment paradigms. See, generally, Takahashi, K. et al., "Post-treatment with an inhibitor of poly(ADP-ribose) polymerase attenuates cerebral damage in focal ischemia"; Brain Res., 829, 46, (1999). Mokudai, T. et al., "Delayed treatment with nicotinamide (vitamin B3) improves neurological outcome and reduces infarct volume after transient focal ischemia in Wistar rats"; Stroke, 31, 1679 (2000). Abdelkarim, G. E. et al., "Protective effects of PJ34, a novel, potent inhibitor of poly(ADP ribose) polymerase (PARP) in vitro and in vivo models of stroke"; Int. J. Mol. Med., 7, 255 (2000). Ding, Y. et al., "Long-term neuroprotective effect of inhibiting poly(ADP-ribose) polymerase in rats with middle cerebral artery occlusion using a behavioral assessment"; Brain Res., 915, 210 (2001).

Other disease models in which the role of PARP has been established by using inhibitors or the knockout are streptozocin-induced diabetes (see, Mabley, J. G. et al., "Inhibition of poly(ADP-ribose) synthetase by gene disruption or inhibition with 5-iodo-6-amino-1,2-benzopyrone protects mice from multiple-low-dose-streptozotocin-induced diabetes"; Br. J. Pharmacol., 133, 909-919 (2001); Gale, E. A. et al., "Molecular mechanisms of beta-cell destruction in IDDM: the role of nicotinamide"; Horm. Res., 45, 39-43 (1996); and Heller, B. et al., "Inactivation of the poly(ADP-ribose) polymerase gene affects oxygen radical and nitric oxide toxicity in islet cells"; J. Biol. Chem., 270, 11176-11180 (1995).

The PARP is also implicated in diabetic cardiomyopathy, see, Pacher, P. et al., "The role of poly(ADP-ribose) polymerase activation in the development of myocardial and endothelial dysfunction in diabetes"; Diabetes, 51, 514-521 (2002); and in head trauma, see, LaPlaca, M. C. et al., "Pharmacological inhibition of poly(ADP-ribose) polymerase is neuroprotective following traumatic brain injury in rats"; J. Neurotrauma, 18, 369-376 (2001). Also see, Verma, A., "Opportunities for neuroprotection in traumatic brain injury"; J. Head Trauma Rehabil., 15, 1149-1161 (2000).

Further diseases involving PARP include myocardial ischemia, see generally, Pieper, A. A. et al., "Myocardial postischemic injury is reduced by poly(ADP-ribose) polymerase-1 gene disruption"; Mol. Med., 6, 271-282 (2000). Also see, Grupp, I. L. et al., "Protection against hypoxia reoxygenation in the absence of poly(ADP-ribose) synthetase in isolated working hearts"; J. Mol. Cell. Cardio., 31, 297-303 (1999).

Additional diseases include experimental allergic encephalomyelitis (EAE), see for example, Scott, G. S. et al., "Role of poly(ADP-ribose) synthetase activation in the development of experimental allergic encephalomyelitis"; J. Neuroimmunology, 117, 78-86 (2001).

It has also been reported that cancer may be caused due to the effects of PARP, see for example, Martin, N. M., "DNA repair inhibition and cancer therapy"; J. Photochem. Photobiol. B, 63, 162-170 (2001). Finally, aging related diseases also have been implicated due to PARP, see Von Zglinicki, T. et al., "Stress, DNA damage and aging—an integrative approach"; Exp. Geront., 36, 1049-1062 (2001). Also see, Rosenthal, D. S. et al., "Poly(ADP-ribose) polymerase and aging"; in "The role of DNA damage and repair in aging", Gilchrist, B. A. and Bohr, V. A., eds., Elsevier Science B. V. (2001), pp 113-133.

All of the references described herein are incorporated herein by reference in their entirety.

It is an object of this invention to provide a series of substituted indole derivatives which are potent, selective inhibitors of PARP-1.

It is also an object of this invention to provide processes for the preparation of the substituted indole derivatives as disclosed herein.

It is further an object of this invention to provide a series of novel indole-3-carboxaldehydes that are potent inhibitors of PARP-1 enzyme as demonstrated by their activity against the enzyme in vitro and in a whole cell assay.

SUMMARY OF THE INVENTION

Thus in accordance with the practice of this invention there is provided a method of treating a disease or a condition caused by the effects of poly(adenosine 5'-diphosphate ribose) polymerase (PARP) in a patient comprising administering to said patient a therapeutically effective amount of a compound including enantiomers, stereoisomers, and tautomers of said compound and pharmaceutically acceptable salts, solvates or derivatives thereof, with said compound having the general structure shown in formula (I):

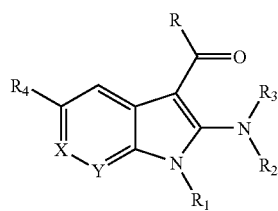

(I)

wherein

R is hydrogen, hydroxy, $C_{1-4}$alkoxy or amino;

$R_1$ is $C_{1-6}$alkyl, $C_{6-12}$aryl, $C_{6-12}$aryl$C_{1-4}$alkyl, $C_{6-12}$arylsulfonyl or heteroaryl, and wherein said alkyl, aryl or heteroaryl is optionally substituted with one or more substituents selected from the group consisting of halogen, $C_{1-6}$alkyl, $C_{2-6}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy, $C_{1-4}$thioalkyl, hydroxy, hydroxy$C_{1-4}$alkyl, $C_{1-4}$acyloxy, nitro, amino, $C_{1-4}$alkylamino, $C_{1-4}$dialkylamino, amino$C_{1-4}$alkyl, $C_{1-4}$alkylamino$C_{1-4}$ alkyl, $C_{1-4}$dialkylamino$C_{1-4}$alkyl, —CN, —$CO_2$H, —$CO_2C_{1-4}$alkyl, —NHCO$C_{1-4}$alkyl, substituted or unsubstituted phenyl, substituted or unsubstituted phenoxy, substituted or unsubstituted benzyloxy, substituted or unsubstituted pyrrolyl, and substituted or unsubstituted pyridyl;

$R_2$ and $R_3$ are the same or different and are each independently selected from:

hydrogen, $C_{1-4}$alkyl, $C_{1-4}$dialkylamino$C_{1-4}$alkyl, pyrrolidinyl$C_{1-4}$alkyl, imidazolyl or heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO and —$CO_2C_{1-4}$alkyl; or $R_2$ and $R_3$ taken together with the nitrogen atom to which they are attached form an imidazolyl or a heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO, —$CO_2C_{1-4}$alkyl, hydroxy$C_{1-4}$alkyl, oxiranyl$C_{1-4}$alkyl, dihydroxy$C_{1-4}$alkyl, —$(CH_2)_a$N—$CO_2C_{1-4}$ alkyl, hydroxyl, and —$(CH_2)_a$OPO$(OC_{1-4}$alkyl$)_2$, wherein a is an integer from 1 to 4;

$R_4$ is $C_{1-4}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy or $C_{1-4}$thioalkyl; and X and Y are the same or different and are each independently selected from: CH or N.

In a further aspect of this invention there is also provided a method of effecting a neuronal activity not mediated by NMDA toxicity in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula (I), as described herein.

In an additional aspect of this invention there is provided a compound, including enantiomers, stereoisomers, and tautomers of said compound and pharmaceutically acceptable salts, solvates or derivatives thereof, with said compound having the general structure shown in formula (I), as described herein.

These and various other aspects of this invention are apparent from the detailed description that follows.

DETAILED DESCRIPTION OF THE INVENTION

The terms as used herein have the following meanings:

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$thioalkyl" "$C_{1-4}$alkoxy$C_{1-4}$alkyl", "hydroxy$C_{1-4}$alkyl", "$C_{1-4}$alkylcarbonyl", "$C_{1-4}$alkoxycarbonyl$C_{1-4}$alkyl", "$C_{1-4}$alkoxycarbonyl", "amino$C_{1-4}$alkyl", "$C_{1-4}$alkylamino", "$C_{1-4}$alkylcarbamoyl$C_{1-6}$alkyl", "$C_{1-4}$dialkylcarbamoyl$C_{1-4}$alkyl" "mono- or di-$C_{1-4}$alkylamino$C_{1-4}$alkyl", "amino$C_{1-4}$alkylcarbonyl" "diphenyl$C_{1-4}$alkyl", "phenyl$C_{1-4}$alkyl", "phenylcarboyl$C_{1-4}$ alkyl" and "phenoxy$C_{1-4}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein the expression "$C_{1-4}$acyl" shall have the same meaning as "$C_{1-6}$alkanoyl", which can also be represented structurally as "R—CO—," where R is a $C_{1-3}$alkyl as defined herein. Additionally, "$C_{1-3}$alkylcarbonyl" shall mean same as $C_{1-4}$acyl. Specifically, "$C_{1-4}$acyl" shall mean formyl, acetyl or ethanoyl, propanoyl, n-butanoyl, etc. Derived expressions such as "$C_{1-4}$acyloxy" and "$C_{1-4}$acyloxyalkyl" are to be construed accordingly.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{6-12}$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$C_{6-12}$arylsulfonyl," is to be construed accordingly.

As used herein, the expression "$C_{6-12}$aryl$C_{1-4}$alkyl" means that the $C_{6-12}$aryl as defined herein is further attached to $C_{1-4}$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-memebered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, benzimidazolyl, indazolyl, pyridofuranyl, pyridothienyl, and the like radicals.

As used herein, the expression "heterocycle" includes all of the known reduced heteroatom containing cyclic radicals. Representative 5-memebered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$-$C_6$alkoxy, $C_1$-$C_6$thioalkyl, $C_1$-$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

The term "ischemia" refers to localized tissue anemia due to obstruction of the inflow of arterial blood. Global ischemia occurs when blood flow to the entire brain (or heart) ceases for a period of time. Global ischemia may result from cardiac arrest. Focal ischemia occurs when a portion of the brain is deprived of its normal blood supply. Focal ischemia may result from thromboembolytic occlusion of a cerebral vessel, traumatic head injury, edema or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity (no glutamate toxicity in the heart) and to the secondary consequences of tissue reperfusion, such as the release of vasoactive products damaged endothelium and the release of cytotoxic products, such as free radicals and leukotrienes, by the damaged tissue. Ischemia can also occur in the heart in myocardial infarction and other cardiovascular disorders in which the coronary arteries have been obstructed as a result of atherosclerosis, thrombi, or spasm and in the eyes in retinal ischemia.

The term "neural tissue damage resulting from ischemia and reperfusion injury and neurodegenerative diseases" includes neurotoxicity, such as seen in vascular stroke and global and focal ischemia, as well as retinal ischemia.

The term "neurodegenerative diseases" includes Alzheimer's disease, Parkinson's disease, and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed with a neurodegenerative disease or who are at risk of developing a neurodegenerative disease. The term also encompasses preventing further neurodegeneration in patients who are already suffering from or have symptoms of a neurodegenerative disease.

The term "treating" refers to:

(i) preventing a disease, disorder or condition from occurring in a patient that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

In one aspect of this invention, there is disclosed a method of treating a disease or a condition caused by the effects of poly(adenosine 5'-diphosphate ribose) polymerase (PARP) in a patient comprising administering to said patient a therapeutically effective amount of a compound including enantiomers, stereoisomers, and tautomers of said compound and pharmaceutically acceptable salts, solvates or derivatives thereof, with said compound having the general structure shown in formula (I):

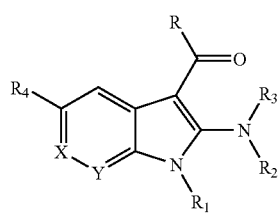

(I)

wherein
R is hydrogen, hydroxy, $C_{1-4}$alkoxy or amino;
$R_1$ is $C_{1-6}$alkyl, $C_{6-12}$aryl, $C_{6-12}$aryl$C_{1-4}$alkyl, $C_{6-12}$arylsulfonyl or heteroaryl, and wherein said alkyl, aryl or heteroaryl is optionally substituted with one or more substituents selected from the group consisting of halogen, $C_{1-6}$alkyl, $C_{2-6}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy, $C_{1-4}$thioalkyl, hydroxy, hydroxy$C_{1-4}$alkyl, $C_{1-4}$acyloxy, nitro, amino, $C_{1-4}$alkylamino, $C_{1-4}$dialkylamino, amino$C_{1-4}$alkyl, $C_{1-4}$alkylamino$C_{1-4}$alkyl, $C_{1-4}$dialkylamino$C_{1-4}$alkyl, —CN, —$CO_2H$, —$CO_2C_{1-4}$alkyl, —NHCO$C_{1-4}$alkyl, substituted or unsubstituted phenyl, substituted or unsubstituted phenoxy, substituted or unsubstituted benzyloxy, substituted or unsubstituted pyrrolyl, and substituted or unsubstituted pyridyl;
$R_2$ and $R_3$ are the same or different and are each independently selected from: hydrogen, $C_{1-4}$alkyl, $C_{1-4}$dialkylamino$C_{1-4}$alkyl, pyrrolidinyl$C_{1-4}$alkyl, imidazolyl or heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO and —$CO_2C_{1-4}$alkyl; or $R_2$ and $R_3$ taken together with the nitrogen atom to which they are attached form an imidazolyl or a heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO, —$CO_2C_{1-4}$alkyl, hydroxy$C_{1-4}$alkyl, oxiranyl$C_{1-4}$alkyl, dihydroxy$C_{1-4}$alkyl, —$(CH_2)_a$N-$CO_2C_{1-4}$alkyl, hydroxyl, and —$(CH_2)_a$OPO$(OC_{1-4}$alkyl$)_2$, wherein a is an integer from 1 to 4;
$R_4$ is $C_{1-4}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy or $C_{1-4}$thioalkyl; and
X and Y are the same or different and are each independently selected from: CH or N.

In one of the embodiments of this method of the invention, a compound in which X and Y are carbon, R is hydrogen and $R_1$ is phenyl is disclosed. In this embodiment, the compound in which $R_2$ and $R_3$ taken together with the nitrogen atom to which they are attached form a heterocycle moiety is preferred. The preferred heterocycle moiety is selected from morpholinyl, thiomorpholinyl, aziridinyl, pyrrolidinyl, piperidinyl, azepanyl, piperazinyl, diazepanyl, diazabicyclo[2.2.1]hept-2-yl, and triazocanyl.

Specific compounds that are part of this embodiment without limitation include:

1-phenyl-2-(thiomorphin4-yl)-1H-indole-3-carboxaldehyde,
2-(piperazin-1-yl)-1-phenyl-1H-indol-3-carboxaldehyde,
5-methyl-1-phenyl-2-(piperazin-1-yl)-1H-indole-3-carboxaldehyde,
2-(piperidin-1-yl)-1-phenyl-1H-indole-3-carboxaldehyde,
2-(azepan-1-yl)-1-phenyl-1H-indole-3-carboxaldehyde,
2-(2,5-diazabicyclo[2.2.1]hept-2-yl)-1-phenyl-1H-indole-3-carboxaldehyde,
2-[1,4]diazepan-1-yl-1-phenyl-1H-indole-3-carboxaldehyde, 1-phenyl-2-[1,4,7]triazocan-1-yl-1H-indole-3-carboxaldehyde and
2-(morpholin-4-yl)-1-phenyl-1H-indole-3-carboxaldehyde.

In a further aspect of this method of the embodiment of the invention, a compound in which $R_1$ is phenyl and is substituted with one or more substituents selected from the group consisting of: nitro, bromine, chlorine, fluorine, iodine, methoxy, ethoxy, thiomethyl, methyl, ethyl, n-butyl, tert-butyl, vinyl, hydroxymethyl, —CHO, —CN, phenyl, phenoxy, dimethylamino, —NHCOCH$_3$, and pyridyl. In addition, in the compounds of this embodiment, $R_2$ and $R_3$ taken together with the nitrogen atom to which they are attached form heterocycle selected from piperidinyl or piperazinyl.

Representative examples of compounds within the scope of this embodiment are selected from the group consisting of:
2-(piperazin-1-yl)-1-(3-nitrophenyl)-1H-indole-3-carboxaldehyde,
2-(piperazin-1-yl)-1-(4-methoxyphenyl)-1H-indole-3-carboxaldehyde,
2-(piperazin-1-yl)-1-(4-tert-butylphenyl)-1H-indole-3-carboxaldehyde,
2-(piperazin-1-yl)-1-(4-bromophenyl)-1H-indole-3-carboxaldehyde,
2-(piperazin-1-yl)-1-(4-chlorophenyl)-1H-indole-3-carboxaldehyde,
2-(piperazin-1-yl)-1-(3-chloro-4-fluorophenyl)-1H-indole-3-carboxaldehyde,
2-(piperazin-1-yl)-1-(3-methoxyphenyl)-1H-indole-3-carboxaldehyde,
2-(piperazin-1-yl)-1-(4-thiomethylphenyl)-1H-indole-3-carboxaldehyde,
2-(piperazin-1-yl)-1-(3-fluorophenyl)-1H-indole-3-carboxaldehyde,
2-(piperazin-1-yl)-1-(3-methylphenyl)-1H-indole-3-carboxaldehyde,
1-(4-tert-butylphenyl)-2-piperazin-1-yl-1H-indole-3-carboxaldehyde,
1-(4-tert-butylphenyl)-2-piperidin-1-yl-1H-indole-3-carboxaldehyde,
1-(3-formylphenyl)-2-(piperazin-2-yl)-1H-indole-3-carboxaldehyde,
1-(biphenyl-4-yl)-2-(piperazin-1-yl)-1H-indole-3-carboxaldehyde hydrochloride,
1-(4-ethylphenyl)-2-(piperazin-1-y)-1H-indole-3-carboxaldehyde hydrochloride,
1-(3-bromophenyl)-2-piperazin-1-yl-1H-indole-3-carboxaldehyde,
1-(4-methyl-3-nitrophenyl)-2-(piperazin-1-yl)-1H-indole-3-carboxaldehyde,
1-(4-dimethylaminophenyl)-2-piperazin-1-yl-1H-indole-3-carboxaldehyde,
1-(4-phenoxyphenyl)-2-piperazin-1-yl-1H-indole-3-carboxaldehyde,
1-(4-methylphenyl)-2-(piperazin-1-yl)-1H-indole-3-carboxaldehyde,
1-(4-fluorophenyl)-2-(piperazin-1-yl)-1H-indole-3-carboxaldehyde hydrochloride,
1-(3-chlorophenyl)-2-(piperazin-1-yl)-1H-indole-3-carboxaldehyde,
2-(piperazin-1-yl)-1-(4-vinylphenyl)-1H-indole-3-carboxaldehyde,
1-(3-hydroxymethylphenyl)-2-(piperazin-1-yl)-1H-indole-3-carboxaldehyde,
1-(3-ethoxyphenyl)-2-(piperazin-1-yl)-1H-indole-3-carboxaldehyde,
1-(4-butylphenyl)-2-(piperazin-1-yl)-1H-indole-3-carboxaldehyde hydrochloride,
N-{3-[3-Formyl-2-(piperazin-1-yl)-indol-1-yl]phenyl}-acetamide hydrochloride,
4-[3-formyl-2-(piperazin-1-yl)-indol-1-yl]-benzonitrile and
2-piperazin-1-yl-1-[(4-pyridin-4-yl)phenyl]-1H-indole-3-carboxaldehyde.

In a further aspect of this embodiment, the compounds in which the heterocycle is further substituted with one ore more substituents selected from the group consisting of: methyl, hydroxyethyl, 2,3-dihydroxypropyl, oxiranylmethyl, oxo, —(CH$_2$)$_2$NHCO$_2$-tert-butyl, —CO$_2$CH$_3$, —CO$_2$-tert-butyl, —CHO, and —(CH$_2$)$_2$OPO(OC$_2$H$_5$)$_2$ are disclosed.

Representative examples of compounds within the scope of this embodiment may be enumerated as follows:
2-[4-(2-hydroxyethyl)piperazin-1-yl]-1-phenyl-1H-indole-3-carboxaldehyde,
2-(4-oxiranylmethylpiperazin-1-yl)-1-phenyl-1H-indole-3-carboxaldehyde,
{2-[4-(3-formyl-1-phenyl-2,3-dihydro-1H-indol-2-yl)-piperazin-1-yl]-ethyl}-carbamic acid tert-butyl ester,
4-(3-formyl-1-phenyl-1H-indole-2-yl)-piperazine-2-carboxylic acid methyl ester,
2-(4-formyl-[1,4]diazepan-1-yl)-1-phenyl-1H-indole-3-carboxaldehyde,
2-[4-(2-hydroxyethyl)diazepan-1-yl]-1-phenyl-1H-indole-3-carboxaldehyde,
2-(4-oxiranylmethyl-[1,4]diazepan-1-yl)-1-phenyl-1H-indole-3-carboxaldehyde,
2-[4-(2,3-dihydroxypropyl)-[1,4]diazepan-1-yl]-1-phenyl-1H-indole-3-carboxaldehyde,
2-(5-oxo-[1,4]diazepam-1-yl)-1-phenyl-1H-indole-3-carboxaldehyde,
4-(3-formyl-1-phenyl-1H-indol-2-yl)piperazine-1-carboxylic acid tert-butyl ester,
2-[4-(2-hydroxyethyl)piperazin-1-yl]-1-phenyl-1H-indole-3-carboxaldehyde hydrochloride,
phosphoric acid diethyl ester 2-[4-(3-formyl-1-phenyl-1H-indol-2-yl)-piperazin-1-yl]-ethyl ester hydrochloride,
2-(3,5-dimethylpiperazin-1-yl)-1-phenyl-1H-indole-3-carboxaldehyde hydrochloride and
5-(3-formyl-1-phenyl-1H-indol-2yl)-2,5-diazabicyclo[2.2.1]heptane-2-carboxylic acid tert-butyl ester.

In a further aspect of this embodiment of the invention, a compound wherein $R_1$ is phenyl which is further substituted with one or more substituents selected from the group consisting of: tert-butyl, iodo, cyanophenyl, and tert-butoxycarbonyl-1-pyrrolyl are described.

Specific compounds of this embodiment may be selected from the group consisting of:
1-(4-tert-butylphenyl)-2-[4-(2-hydroxyethyl)piperazin-1-yl]-1H-indole-3-carboxaldehyde,
phosphoric acid 2-{4-[1-(4-tert-butylphenyl)-3-formyl-1H-indol-2-yl]-piperazin-1-yl}-ethyl ester diethyl ester hydrochloride,
1-(4-tert-butylphenyl)-2-(4-methyl-piperazin-1-yl)-1H-indole-3-carboxaldehyde,
4-[1-(4-tert-butylphenyl)-3-formyl-1H-indol-2-yl]piperazine-1-carboxylic acid tert-butyl ester,
5-[1-(4-tert-butylphenyl)-3-formyl-1H-indol-2-yl]-2,5-diazabicyclo[2.2.1]heptane-2-carboxylic acid tert-butyl ester,
1-(4-tert-butyl-phenyl)-2-(2-methyl-aziridin-1-yl)-1H-indole-3-carboxaldehyde, 4-[3-formyl-1-(4-iodophenyl)-1H-indol-2-yl]-piperazine-1-carboxylic acid tert-butyl ester, 4-[1-(4'-cyanobiphenyl-4-yl)-3-formyl-1H-indol-2-yl]-piperazine-1-carboxylic acid tert-butyl ester, and 4-{1-[4-(tert-butoxylcarbonyl-1H-pyrrol-2-yl)-phenyl]-3-formyl-1H-indol-2-yl}-piperazine-1-carboxylic acid tert-butyl ester.

In yet another embodiment of the method of this invention, the compound of formula (I), wherein X is nitrogen and Y is carbon or X is carbon and Y is nitrogen, are described.

Specific compounds of this embodiment include without any limitation:

1-phenyl-2-(piperazin-1-yl)-1,3-dihydropyrrolo[2,3-b]pyridine-3-carboxaldehyde, and 1-phenyl-2-(piperazin-1-yl)-1H-pyrrolo[2,3-c]pyridine-3-carboxaldehyde.

In yet another embodiment of the method of this invention, there are provided compounds of formula (I), wherein $R_2$ and $R_3$ taken together with the nitrogen atom to which they are attached form imidazolyl. An example of this embodiment is 2-imidazol-1-yl-1-phenyl-1H-indole-3-carboxaldehyde.

In another embodiment of the method of this invention, there is disclosed a compound of formula (I), wherein $R_2$ is hydrogen or methyl, and $R_3$ is dimethylaminoethyl, pyrrolidinylethylamino, and piperidinyl.

Specific compounds of this embodiment are selected from the group consisting of:

2-(2-dimethylaminoethylamino)-1-phenyl-1H-indole-3-carboxaldehyde,

2-[(methylpiperidin-4-yl)amino]-1-phenyl-1H-indole-3-carboxaldehyde, 1-(4-tert-butylphenyl)-2-[(2-dimethylaminoethyl)-methylamino]-1H-indole-3-carboxaldehyde, 1-(4-tert-butylphenyl)-2-(2-dimethylaminoethylamino)-1H-indole-3-carboxaldehyde, and 1-(4-tert-butylphenyl)-2-(2-pyrrolidin-1-yl-ethylamino)-1H-indole-3-carboxaldehyde hydrochloride.

In another embodiment of the method of this invention, there are provided compounds of formula (I), wherein $R_1$ is methyl, benzyl, naphthyl, thienyl, pyridinyl, and benzenesulfonyl. Examples of this embodiment include:

2-(piperazin-1-yl)-1-methyl-1H-indole-3-carboxaldehyde, 2-(piperazin-1-yl)-1-benzyl-1H-indole-3-carboxaldehyde, 2-(piperazin-1-yl)-1-(1-naphthyl)-1H-indole-3-carboxaldehyde, 2-(piperazin-1-yl)-1-(thien-3-yl)-1H-indole-3-carboxaldehyde, 2-(piperazin-1-yl)-1-(pyridin-2-yl)-1H-indole-3-carboxaldehyde, 2-(piperazin-1-yl)-1-(pyridin-3-yl)-1H-indole-3-carboxaldehyde and 1-benzenesulfonyl-2-(piperazin-1-yl)-1H-indole-3-carboxaldehyde.

Finally, in another embodiment of the method of this invention there is provided a compound of formula (I), wherein R is hydroxy, methoxy or amino; $R_1$ is phenyl, $R_2$ and $R_3$ taken together with the nitrogen atom to which they are attached form piperazinyl, $R_4$ is hydrogen, and X and Y are carbon. Representative examples within the scope of this embodiment include:

2-(piperazin-1-yl)-1-phenyl-1H-indole-3-carboxylic acid, 2-(piperazin-1-yl)-1-phenyl-1H-indole-3-carboxylic acid amide, and 2-(piperazin-1-yl)-1-phenyl-1H-indole-3-carboxylic acid methyl ester.

In this embodiment, a specific disease or a disorder or a condition that can be treated with the compound of this invention include, without any limitation: tissue damage resulting from cell damage or death due to necrosis or apoptosis, neuronal mediated tissue damage or diseases, neural tissue damage resulting from ischemia and reperfusion injury, neurological disorders and neurodegenerative diseases, vascular stroke, cardiovascular disorders, age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock and aging.

In another aspect of this embodiment, a specific disease, a disorder or a condition that can be treated with the compound of this invention include, without any limitation: tissue damage resulting from cell damage or death due to necrosis or apoptosis, neuronal mediated tissue damage or diseases, cerebral ischemia, head trauma, stroke, reperfusion injury, neurological disorders and neurodegenerative diseases, vascular stroke, cardiovascular disorders, myocardial infarction, myocardial ischemia, experimental allergic encephalomyelitis (EAE), multiple sclerosis (MS), ischemia related to cardiac surgery, age-related macular degeneration, arthritis, atherosclerosis, cancer, degenerative diseases of skeletal muscle involving replicative senescence, diabetes and diabetic cardiomyopathy. As used herein, ischemia related to cardiac surgery refers to any brain damage occurring during open heart and other cardiac surgeries at which time the patient may be on a heart and/or a lung machine.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of PARP. That is, the compounds of the present invention have PARP inhibitory activity and may be effectively administered to ameliorate any disease state which is mediated all or in part by PARP.

In yet another embodiment of this invention, there is provided a method of effecting a neuronal activity in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula (I) as described herein. The neuronal activity as described herein may or may not be mediated by NMDA toxicity.

In this aspect of the embodiment of this invention, specific neuronal activity without any limitations may be enumerated as follows. Stimulation of damaged neurons, promotion of neuronal regeneration, prevention of neurodegeneration, and treatment of a neurological disorder. Generally, damaged neurons result from cerebral ischemia, retinal ischemia, or reperfusion injury. Thus the compounds of this invention improve neuronal activity thereby ameliorate the effects of ischemia.

In a further aspect of this embodiment, specific neurological disorders that may be enumerated without any limitation include: peripheral neuropathy caused by physical injury or disease state, traumatic brain injury, physical damage to the spinal cord, stroke associated with brain damage, neurological disorder relating to neurodegeneration.

Further, in this embodiment specific neurological disorder relating to neurodegeneration that may be enumerated without any limitation include: Alzheimer's disease, Parkinson's disease, Huntington's Disease and amyotrophic lateral sclerosis.

In still another embodiment of this invention, there is also provided a method of treating a cardiovascular disorder in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula (I) as described herein.

In this embodiment of this invention specific cardiovascular disorder that may be enumerated include, without any limitation, coronary artery disease, myocardial infarction, angina pectoris, cardiogenic shock and cardiovascular tissue damage.

All of the various embodiments of the compounds used in the methods of this invention as disclosed herein can be used in the method of treating various disease states as described herein. As stated herein, the compounds used in the method of this invention are capable of inhibiting the effects of PARP and thereby alleviating the effects and/or conditions caused due to the activity of PARP. In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

Several of the indole derivatives used in the method of this invention are known. For instance, a compound where R, $R_2$, $R_3$, $R_4$, are hydrogen, X and Y are carbon, and $R_1$ is phenyl or methyl is disclosed in Becher et al., Synthesis, 530-533 (1989). A compound in which R and $R_4$ are hydrogen, $R_2$ and $R_3$ are methyl, X and Y are carbon, and $R_1$ is phenyl is disclosed in DE 2 707 268 (1978). Finally, a compound in which R, $R_2$, $R_3$, $R_4$, are hydrogen, X and Y are carbon, and $R_1$ is ethyl is disclosed in Capperucci et al., J. Org. Chem., 60, 2254-2256 (1995). A series of indole derivatives is also disclosed in U.S. Pat. No. 4,148,895. All of the references described herein are incorporated herein by reference in their entirety.

However, several of the compounds of this invention are novel. Thus, in this aspect of the invention there is provided a compound, including enantiomers, stereoisomers, and tautomers of said compound and pharmaceutically acceptable salts, solvates or derivatives thereof, with said compound having the general structure shown in formula (I):

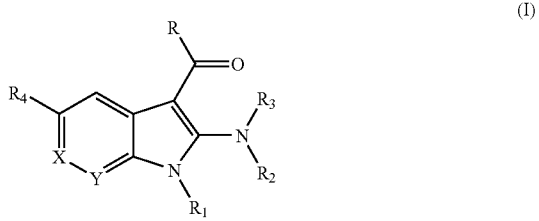

(I)

wherein

R is hydrogen, hydroxy, $C_{1-4}$alkoxy or amino;

$R_1$ is naphthyl, substituted phenyl, $C_{6-12}$aryl$C_{1-4}$alkyl, $C_{6-12}$arylsulfonyl or heteroaryl, and wherein said naphthyl, aryl or heteroaryl is optionally substituted with one or more substituents selected from the group consisting of halogen, $C_{1-6}$alkyl, $C_{1-6}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy, $C_{1-4}$thioalkyl, hydroxy, hydroxy$C_{1-4}$alkyl, $C_{1-4}$acyloxy, nitro, amino, $C_{1-4}$alkylamino, $C_{1-4}$dialkylamino, amino$C_{1-4}$alkyl, $C_{1-4}$alkylamino$C_{1-4}$alkyl, $C_{1-4}$dialkylamino$C_{1-4}$alkyl, —CN, —CO$_2$H, —CO$_2$C$_{1-4}$alkyl, —NHCOC$_{1-4}$alkyl, substituted or unsubstituted phenyl, substituted or unsubstituted phenoxy, substituted or unsubstituted benzyloxy, substituted or unsubstituted pyrrolyl and substituted or unsubstituted pyridyl;

$R_2$ and $R_3$ are the same or different and are each independently selected from: hydrogen, $C_{1-4}$alkyl, $C_{1-4}$dialkylamino$C_{1-4}$alkyl, pyrrolidinyl$C_{1-4}$alkyl, imidazolyl or heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO and —CO$_2$C$_{1-4}$alkyl; or $R_2$ and $R_3$ taken together with the nitrogen atom to which they are attached form an imidazolyl or a heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO, —CO$_2$C$_{1-4}$alkyl, hydroxy$C_{1-4}$alkyl, oxiranyl$C_{1-4}$alkyl, dihydroxy$C_{1-4}$alkyl, —(CH$_2$)$_a$N—CO$_2$C$_{1-4}$alkyl, hydroxyl and —(CH$_2$)$_a$OPO(OC$_{1-4}$alkyl)$_2$, wherein a is an integer from 1 to 4;

$R_4$ is $C_{1-4}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$alkoxy or $C_{1-4}$thioalkyl; and X and Y are the same or different and are each independently selected from: CH or N.

A few of the novel compounds within the scope of this invention may be listed as follows:

2-(piperazin-1-yl)-1-(3-nitrophenyl)-1H-indole-3-carboxaldehyde, 2-(piperazin-1-yl)-1-(4-methoxyphenyl)-1H-indole-3-carboxaldehyde, 2-(piperazin-1-yl)-1-(4-tert-butylphenyl)-1H-indole-3-carboxaldehyde, 2-(piperazin-1-yl)-1-(4-bromophenyl)-1H-indole-3-carboxaldehyde, 2-(piperazin-1-yl)-1-(4-chlorophenyl)-1H-indole-3-carboxaldehyde, 2-(piperazin-1-yl)-1-(3-chloro-4-fluorophenyl)-1H-indole-3-carboxaldehyde, 2-(piperazin-1-yl)-1-(3-methoxyphenyl)-1H-indole-3-carboxaldehyde, 2-(piperazin-1-yl)-1-(4-thiomethylphenyl)-1H-indole-3-carboxaldehyde, 2-(piperazin-1-yl)-1-(3-fluorophenyl)-1H-indole-3-carboxaldehyde, 2-(piperazin-1-yl)-1-(3-methylphenyl)-1H-indole-3-carboxaldehyde, 1-(4-tert-butylphenyl)-2-piperazin-1-yl-1H-indole-3-carboxaldehyde, 1-(4-tert-butylphenyl)-2-piperidin-1-yl-1H-indole-3-carboxaldehyde, 1-(3-formylphenyl)-2-(piperazin-2-yl)-1H-indole-3-carboxaldehyde,
1-(biphenyl-4-yl)-2-(piperazin-1-yl)-1H-indole-3-carboxaldehyde hydrochloride,
1-(4-ethylphenyl)-2-(piperazin-1-y)-1H-indole-3-carboxaldehyde hydrochloride,
1-(3-bromophenyl)-2-piperazin-1-yl-1H-indole-3-carboxaldehyde,
1-(4-methyl-3-nitrophenyl)-2-(piperazin-1-yl)-1H-indole-3-carboxaldehyde,
1-(4-dimethylaminophenyl)-2-piperazin-1-yl-1H-indole-3-carboxaldehyde,
1-(4-phenoxyphenyl)-2-piperazin-1-yl-1H-indole-3-carboxaldehyde,
1-(4-methylphenyl)-2-(piperazin-1-yl)-1H-indole-3-carboxaldehyde,
1-(4-fluorophenyl)-2-(piperazin-1-yl)-1H-indole-3-carboxaldehyde hydrochloride,
1-(3-chlorophenyl)-2-(piperazin-1-yl)-1H-indole-3-carboxaldehyde,
2-(piperazin-1-yl)-1-(4-vinylphenyl)-1H-indole-3-carboxaldehyde,
1-(3-hydroxymethylphenyl)-2-(piperazin-1-yl)-1H-indole-3-carboxaldehyde,
1-(3-ethoxyphenyl)-2-(piperazin-1-yl)-1H-indole-3-carboxaldehyde,
1-(4-butylphenyl)-2-(piperazin-1-yl)-1H-indole-3-carboxaldehyde hydrochloride,
N-{3-[3-Formyl-2-(piperazin-1-yl)-indol-1-yl]phenyl}-acetamide hydrochloride,
4-[3-formyl-2-(piperazin-1-yl)-indol-1-yl]-benzonitrile, and
2-piperazin-1-yl-1-[(4-pyridin-4-yl)phenyl]-1H-indole-3-carboxaldehyde.

The following compounds are also novel:
1-(4-tert-butylphenyl)-2-[4-(2-hydroxyethyl)piperazin-1-yl]-1H-indole-3-carboxaldehyde,
phosphoric acid 2-{4-[1-(4-tert-butylphenyl)-3-formyl-1H-indol-2-yl]-piperazin-1-yl}-ethyl ester diethyl ester hydrochloride,
1-(4-tert-butylphenyl)-2-(4-methyl-piperazin-1-yl)-1H-indole-3-carboxaldehyde,
4-[1-(4-tert-butylphenyl)-3-formyl-1H-indol-2-yl]piperazine-1-carboxylic acid tert-butyl ester,
5-[1-(4-tert-butylphenyl)-3-formyl-1H-indol-2-yl]-2,5-diazabicyclo[2.2.1]heptane-2-carboxylic acid tert-butyl ester,
1-(4-tert-butyl-phenyl)-2-(2-methyl-aziridin-1-yl)-1H-indole-3-carboxaldehyde,
4-[3-formyl-1-(4-iodophenyl)-1H-indol-2-yl]-piperazine-1-carboxylic acid tert-butyl ester,
4-[1-(4'-cyanobiphenyl-4-yl)-3-formyl-1H-indol-2-yl]-piperazine-1-carboxylic acid tert-butyl ester, and
4-{1-[4-(tert-butoxylcarbonyl-1H-pyrrol-2-yl)-phenyl]-3-formyl-1H-indol-2-yl}-piperazine-1-carboxylic acid tert-butyl ester.

In a further aspect of this embodiment, the compound of formula (I) wherein X is nitrogen and Y is carbon or X is carbon and Y is nitrogen is novel. Specific examples within the scope of this embodiment, without any limitation, may be enumerated as follows:
1-phenyl-2-(piperazin-1-yl)-1,3-dihydropyrrolo[2,3-b]pyridine-3-carboxaldehyde,
1-phenyl-2-(piperazin-1-yl)-1H-pyrrolo[2,3-c]pyridine-3-carboxaldehyde,
2-[1,4]diazepan-1-yl-1-phenyl-1H-pyrrolo[2,3-b]pyridine-3-carbaldehyde; trifluoro-acetic acid salt, and
2-piperazin-1-yl-1-pyridin-3-yl-1H-pyrrolo[2,3-b]pyridine-3-carbaldehyde; bis-trifluoro-acetic acid salt.

The compound of formula (I), wherein $R_2$ and $R_3$ taken together with the nitrogen atom to which they are attached form imidazolyl is also novel. A specific example of this embodiment include without any limitation, 2-imidazol-1-yl-1-phenyl-1H-indole-3-carboxaldehyde.

The compound of formula (I), wherein $R_2$ is hydrogen or methyl, and $R_3$ is dimethylaminoethyl, pyrrolidinylethylamino, and piperidinyl is also novel. Examples of compounds within the scope of this embodiment include without any limitation the following:
2-(2-dimethylaminoethylamino)-1-phenyl-1H-indole-3-carboxaldehyde,
2-[(methylpiperidin-4-yl)amino]-1-phenyl-1H-indole-3-carboxaldehyde,
1-(4-tert-butylphenyl)-2-[(2-dimethylaminoethyl)-methylamino]-1H-indole-3-carboxaldehyde,
1-(4-tert-butylphenyl)-2-(2-dimethylaminoethylamino)-1H-indole-3-carboxaldehyde, and
1-(4-tert-butylphenyl)-2-(2-pyrrolidin-1-yl-ethylamino)-1H-indole-3-carboxaldehyde hydrochloride.

Finally, the compound of formula (I), wherein $R_1$ is benzyl, naphthyl, thienyl, pyridinyl, and benzenesulfonyl is novel. Specific compounds encompassed by this embodiment without any limitation include the following:
2-(piperazin-1-yl)-1-benzyl-1H-indole-3-carboxaldehyde,
2-(piperazin-1-yl)-1-(1-naphthyl)-1H-indole-3-carboxaldehyde,
2-(piperazin-1-yl)-1-(thien-3-yl)-1H-indole-3-carboxaldehyde,
2-(piperazin-1-yl)-1-(pyridin-2-yl)-1H-indole-3-carboxaldehyde,
2-(piperazin-1-yl)-1-(pyridin-3-yl)-1H-indole-3-carboxaldehyde and
1-benzenesulfonyl-2-(piperazin-1-yl)-1H-indole-3-carboxaldehyde.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes 1-6, wherein the X, Y, Z, $R_1$, $R_2$, $R_3$ and $R_4$ are as defined for Formula (I) unless otherwise indicated.

Scheme 1 shows a general procedure for the synthesis of the starting oxindole (II). Generally, this approach is most suitable for those compounds wherein X and Y are carbon and $R_1$ is phenyl. As depicted, in Step 1, Scheme 1, the starting intermediate, oxindole (II), can be prepared in two separate pathways. In one approach, the substituted phenylamine, 1 is reacted with α-chloro-acetyl chloride, 2, in a suitable organic solvent such as toluene and in the presence of a suitable base such as triethylamine. The resulting acetanilide derivative 3 is cyclyzed in Step 2, Scheme 1, under Friedel-Crafts arylation conditions to form oxindole (II). Generally, such reactions are carried out using a Lewis acid such as aluminum chloride in an inert non-polar solvent such as 1,2-dichlorobenzene. However, various modified procedures known in the art for the preparation of such materials can also be employed.

Alternatively, as noted in Step 3, Scheme 1, the starting substituted phenylamine, 1 can directly be reacted with oxalyl chloride to form a substituted isatin derivative, 4. This reaction can be carried out in a suitable organic solvent such as toluene. The resulting isatin derivative, 4 is then converted to oxindole intermediate, (II) by reaction with hydrazine under basic conditions, typically in the presence of potassium hydroxide, in a polar solvent such as glycol.

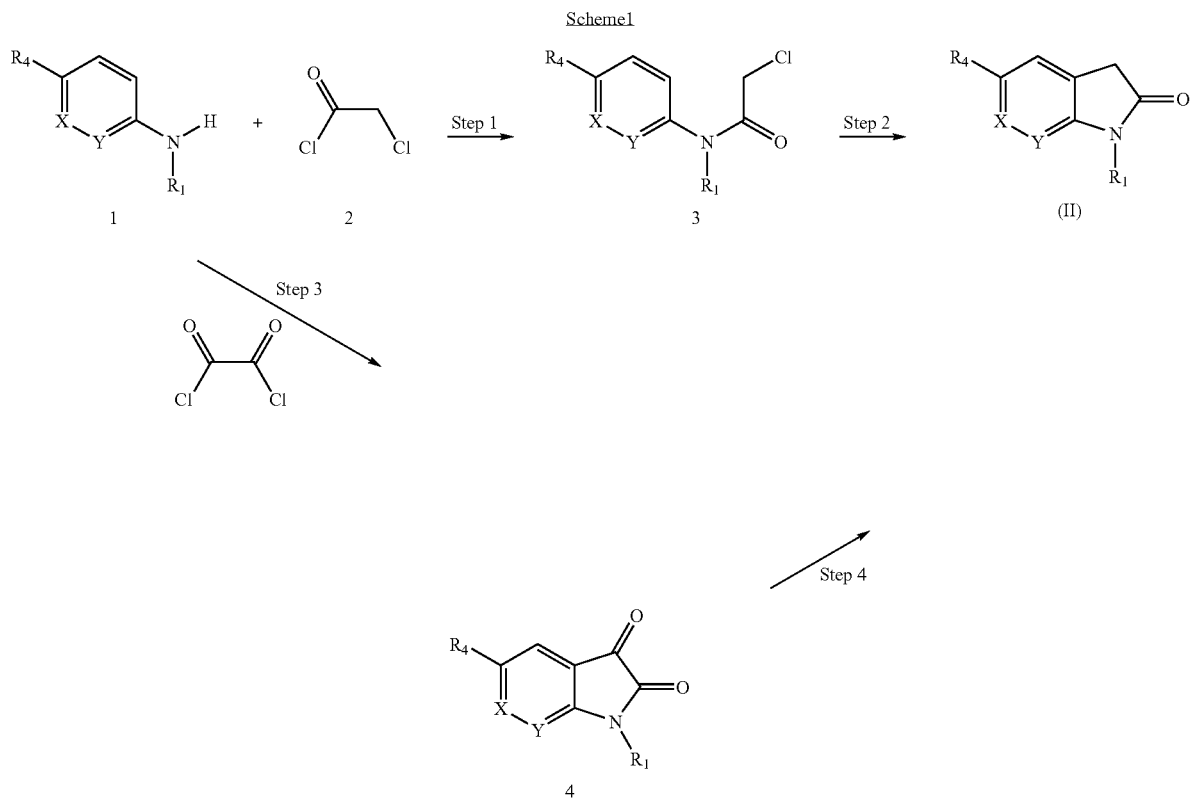

Scheme 2 illustrates an alternative procedure for the preparation of the intermediate oxindole (II). This approach is again suitable for those compounds in which X and Y are carbon. In Step 1A, Scheme 2, substituted isatin derivative 5 is reacted with a suitable $R_1$-Z to form the N-substituted isatin derivative 4 where Z is a suitable leaving group. This reaction is particularly suitable for those compounds in which $R_1$ is substituted or unsubstituted aryl such as phenyl or naphthyl. The reaction is typically carried out using aryl boronic acid (such as phenyl boronic acid for $R_1$=phenyl) in the presence of a catalyst such as copper acetate and an organic base such as triethylamine and/or pyridine in a suitable organic solvent. The isatin derivative 4 can also be prepared in an analogous manner starting from an oxindole 6. In Step 2, Scheme 2, the isatin derivative 4 is converted to oxindole intermediate (II) by reacting with hydrazine as described above. Finally, in Step 3, Scheme 2, the intermediate (II) is converted to the compound of the present invention in which R is hydrogen by reacting first with a Vilsmeier reagent formed by the action of phosphorus oxychloride with DMF and then reacting with desired amine, $R_2R_3NH$.

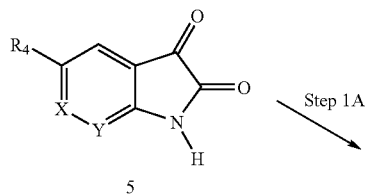

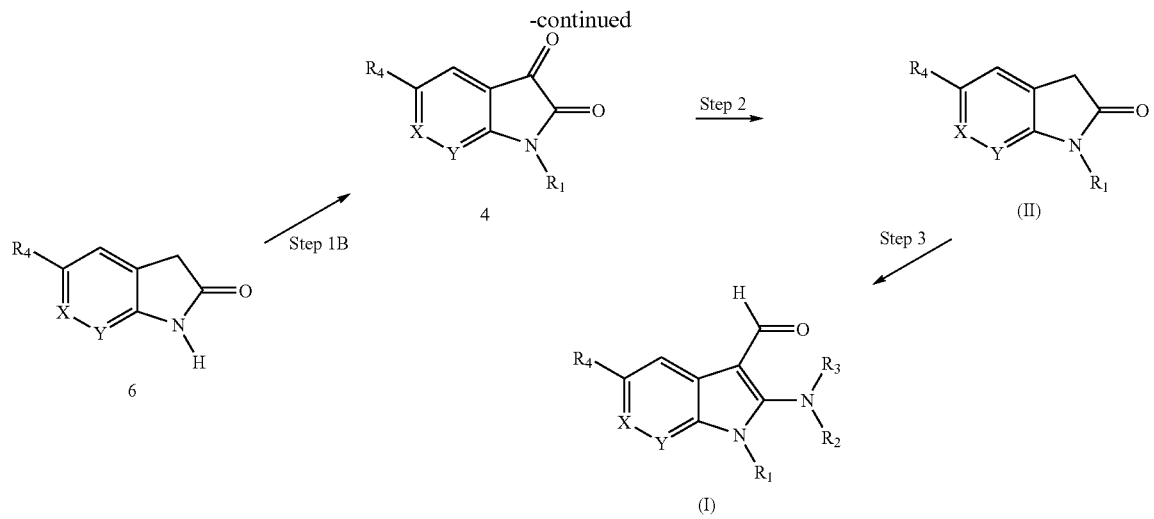

Scheme 3 illustrates an alternative procedure for the preparation of compounds of this invention in which X and Y are carbon and R is hydrogen. In Step 1, Scheme 3, the substituted oxindole 7 is reacted with a Vilsmeier reagent as described above to form 5-substituted-2-chloro-indole-3-carboxaldehyde 8. In Step 2, Scheme 3, the aldehyde 8 is subjected to N-substitution reaction using a desired $R_1Z$ as described above to form the aldehyde intermediate (III). In general, such a substitution reaction is carried out using a boronic acid, $R_1B(OH)_2$, in the presence of a catalyst such as copper acetate and a mixture of organic base such as triethylamine and pyridine in an aprotic non-polar organic solvent such as dichloromethane. Finally, in Step 3, Scheme 3, the aldehyde intermediate (III) is reacted with desired amine, $R_2R_3NH$, to form the compound (I) of this invention in which R is hydrogen.

-continued

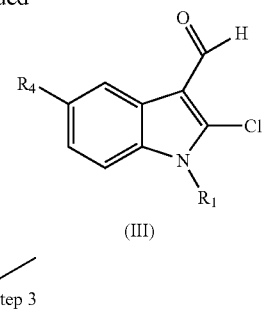

Scheme 3

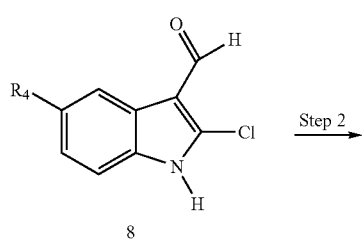

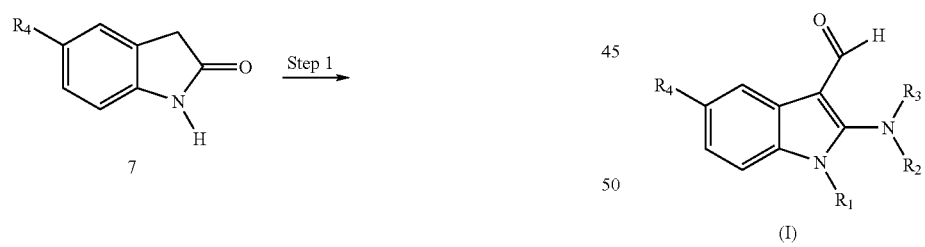

Scheme 4 illustrates yet another approach to the preparation of the intermediate oxindole (II). This approach is particularly suitable for the preparation of the compounds of this invention in which $R_1$ is heteroaryl and X and Y are carbon. In Step 1, Scheme 4, 5-substituted-indole 9 is first reacted with heteroaryl compound of the formula $R_1$-Z where Z is a halogen. This approach is especially suitable for the preparation of compounds where $R_1$ is pyridinyl or thienyl.

Thus, in accordance with this procedure the indole, 9 is reacted with either 3-bromopyridine, 2-bromothiophene or 2-fluoropyridine in the presence of a suitable base and a catalyst depending upon the type of heteroaryl compound, $R_1$-Z employed. Thus for example, with 2-fluoropyridine, sodium hydride is used as the base in DMF. Sodium tert-butoxide, tris(dibenzylideneacetone)palladium, 2-(ditert-butylphosphine)biphenyl in toluene is used for coupling 3-bromopyridine. Potassium carbonate and cuprous bromide in NMP are used to couple 2-bromothiophene. The N-substituted indole 10 so formed is then oxidized to oxindole II in Step 2, Scheme 4. The latter oxidation step can be carried out using any of the known procedures in the art. Typically, such oxidations are carried out using N-chlorosuccinimide in dichloromethane at ambient temperature and subsequently working-up the reaction product in acetic acid and phosphoric acid to produce the oxindole (II), which is then converted to the desired compound of this invention following any of the procedures described above in Schemes 1-3.

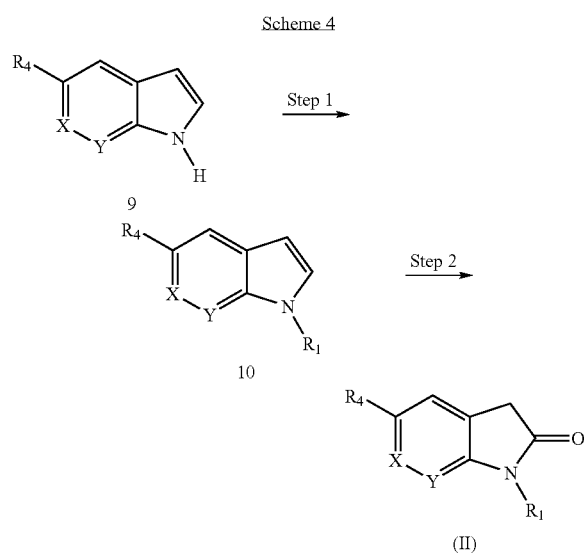

Scheme 5 illustrates another procedure for the preparation of the compounds of this invention in which Y is nitrogen. A suitable pyridine derivative 11 is converted to oxindole intermediate (IIA) in Steps 1 to 3, Scheme 5. Thus, in Step 1, Scheme 5, the pyridine derivative 11 is oxidized to form pyridine-N-oxide 12, which is chlorinated with a suitable chlorinating agent in Step 2, Scheme 5. The chlorination can be carried out, for example, using phosphorus oxychloride to form the 2-chloro-pyridine intermediate 13. In Step 3, Scheme 5, the intermediate 13 is cyclyzed under suitable reaction conditions to form the oxindole intermediate (IIA), which can further be converted to the compounds of this invention using any of the procedures of Schemes 1 to 3 or Scheme 6 as described below.

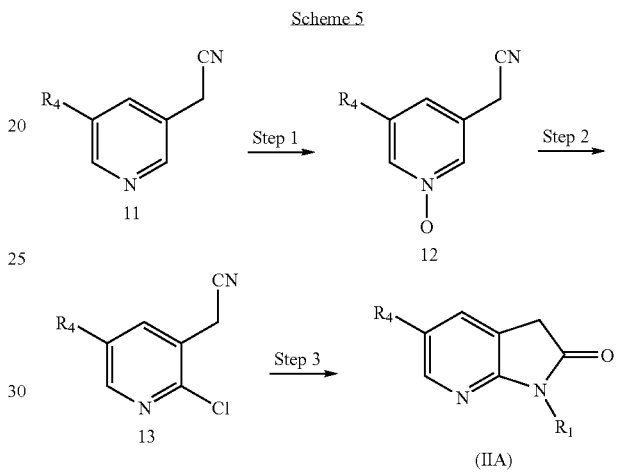

Finally, Scheme 6 illustrates yet another procedure for the preparation of the compounds of this invention (I) in which X is nitrogen. Steps 1 to 4, Scheme 6 show an approach of converting a pyridine derivative 14 to oxindole intermediate 18. The oxindole 18 so formed is converted to compounds of this invention (IB) following the Steps 5 to 8, Scheme 6.

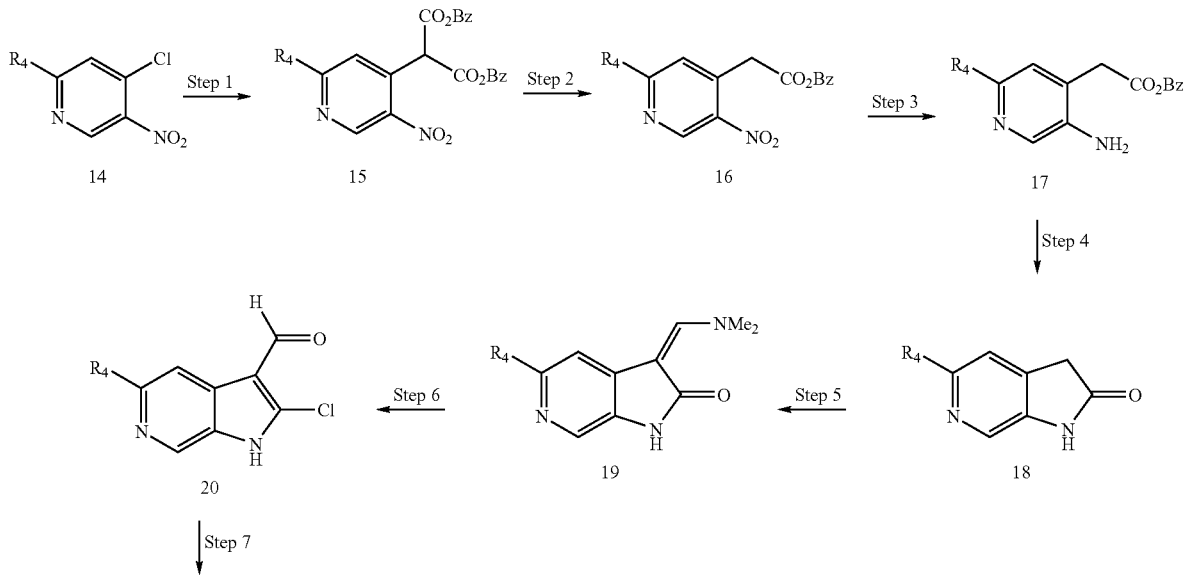

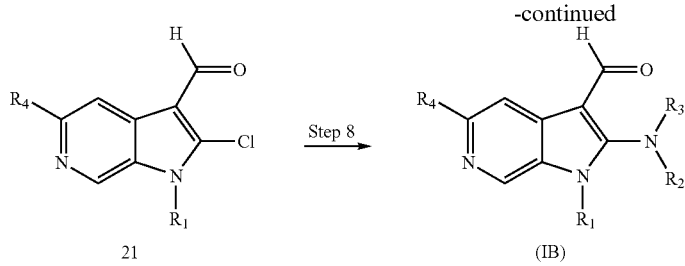

Finally, in yet another embodiment of this invention, there is also provided a pharmaceutical composition comprising a pharmaceutically acceptable carrier and a compound, including enantiomers, stereoisomers, and tautomers of said compound and pharmaceutically acceptable salts, solvates or derivatives thereof, with said compound having the general structure shown in formula (I) as described herein.

As described herein, the pharmaceutical compositions of this invention feature PARP inhibitory activity and thus are useful in treating any disease, condition or a disorder caused due to the effects of PARP in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1$H NMR spectra are run at 300 MHz on a Gemini 300 or Varian VXR 300 spectrometer and are determined in a deuterated solvent, such as DMSO-$D_6$ or $CDCl_3$ unless otherwise noted. Chemical shifts values are indicated in parts per million (ppm) with reference to tetramethylsilane (TMS) as the internal standard. The LC/MS are run on a Micromass Platform LCZ.

As used in the examples and preparations that follow, the terms used therein shall have the meanings indicated: "kg" refers to kilograms, "g" refers to grams, "mg" refers to milligrams, "μg" refers to micrograms, "pg" refers to picograms, "lb" refers to pounds, "oz" refers to ounces, "mol" refers to moles, "mmol" refers to millimoles, "μmole" refers to micromoles, "nmole" refers to nanomoles, "L" refers to liters, "mL" or "ml" refers to milliliters, "μL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "μM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "μCi" refers to microcuries, "i.p." refers to intraperitoneally, "i.v." refers to intravenously, anhyd=anhydrous; aq=aqueous; min=minute; hr=hour; d=day; sat=saturated; s=singlet, d=doublet; t=triplet; q=quartet; m=multiplet; dd=doublet of doublets; br=broad; LC=liquid chromatograph; MS=mass spectrograph; ESIMS=electrospray ionization/mass spectrograph; RT=retention time; M=molecular ion.

The following examples describe the procedures used for the preparation of various starting materials employed in the preparation of the compounds of this invention.

Preparation 1

1-Phenyl-1H-indol-2-one

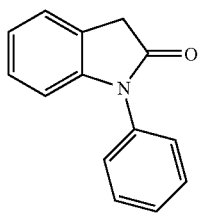

The title compound is prepared in accordance with the procedures described in Latrell, Bartmann, Granzier DE 2 707 268 (1978) as follows. A solution of diphenylamine (40 g, 237 mmol) and triethylamine (66.1 mL, 474 mmol) in toluene (65 mL) is added dropwise to a solution of chloroacetyl chloride (20.7 mL, 260 mmol) in toluene (40 mL) while cooling in an ice-water bath. The cold bath is removed and the reaction mixture is heated at 55-65° C. for 3 hr. The cooled reaction mixture is diluted with toluene (100 mL), filtered and the filtrate concentrated to give 2-chloro-N,N-diphenylacetamide (24.4 g, 42% yield) as a light brown solid. NMR (CDCl$_3$) 7.56-7.19 (10H, m), 4.01 (2H, s).

Aluminum chloride (8.0 g, 60 mmol) is added in two portions to a solution of the above amide (5.0 g, 20.4 mmol) in 1,2-dichlorobenzene (10 mL). The reaction mixture is heated at reflux for 30 min, cooled slightly, poured onto ice (100 g) and the resulting solids are collected by filtration and washed with pentane. The resulting beige solid is dissolved in ethyl acetate, dried, filtered and concentrated to give 1-phenyl-1H-indol-2-one (2.53 g, 60% yield) as a beige solid. NMR 7.57 (2H, t), 7.41 (3H, m), 7.32 (1H, d), 7.2 (1H, t), 7.09 (1H, t), 6.79 (1H, d); 3.73 (2H, d).

Preparation 2

2-Chloro-1-phenyl-1H-indole-3-carboxaldehyde

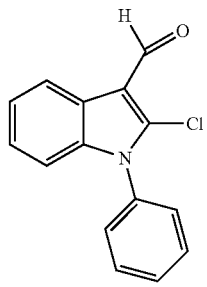

The title compound can be synthesized in accordance with the procedures described in Andreani, A.; Bonazzi, D. et al. J. Med. Chem. 20, 1344-1346, 1977; Latrell, Bartmann, Granzier DE 2 707 268 (1978) or in accordance with the procedures set forth below.

Phosphorous oxychloride (50 mL, 538 mmol) is added slowly to a solution of DMF (50 mL) in dichloromethane (50 mL) maintaining the temperature at 5° C. After 30 min, a solution of 1-phenyl-1H-indol-2-one (25 g, 120 mmol) and pyridine (25 mL, 309 mmol) in chloroform (125 mL) is added and the reaction is stirred 48 hr at room temperature. The reaction is poured into ice water (600 mL) and the aqueous layer is separated and extracted with chloroform (3×200 mL). The combined organic layer and extracts is dried, filtered and concentrated. The solid residue is crystallized from ethanol to afford 2-chloro-1-phenyl-1H-indole-3-carboxaldehyde (12.0 g, 39.25% yield) as an orange solid. NMR (CDCl$_3$) 10.21 (1H, s), 8.37 (1H, d), 7.60 (3H, m), 7.41 (2H, m), 7.38 (1H, t), 7.28 (1H, m), 7.10 (1H, d). A second crop (7.5 g, 24.5% yield) is obtained by concentration of the filtrate and chromatography the residue eluting with dichloromethane.

Preparation 3

1-Phenyl-1H-indole-2,3-dione

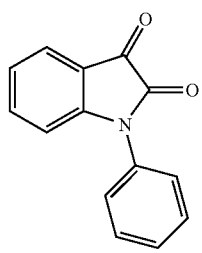

The title compound is prepared following the procedures of Bryant, N. M., III et al. Syn Commun, 23, 1617-25 (1993) as follows. A solution of diphenylamine (26.6 g, 157 mmol) in toluene (65 mL) is added slowly to a solution of oxalyl chloride (14.8 mL, 170 mmol) in toluene (35 mL) while cooling in an ice-water bath to maintain the temperature below 40° C. The resulting brown slurry is heated at 55-65° C. for 1 hr. CAUTION: There is vigorous evolution of hydrogen chloride gas. Approximately 100 mL of solvent is removed by distillation (it contains unreacted oxalyl chloride) and the residue is heated overnight at 118-125° C. The reaction is cooled and then poured into ice-water (200 mL), extracted with ethyl acetate (4×250 mL). The combined extract is dried, filtered and concentrated to give 1-phenyl-1H-indole-2,3-dione (33.0 g, 94% yield). H-NMR 7.70 (1H, d), 7.58 (3H, d), 7.43 (3H, m), 7.19 (1H, t), 6.90 (1H, d).

Preparation 4

2-Chloro-1-phenyl-1H-indole-3-carboxaldehyde

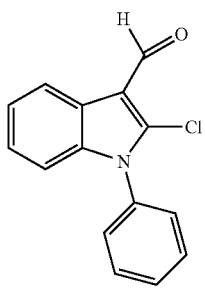

A mixture of 2-chloro-1H-indole-3-carboxaldehyde (5.00 g, 27.8 mmol), phenylboronic acid (6.79 g, 55.6 mmol), cupric acetate (10.11 g, 55.7 mmol), pyridine (4.40 g, 55.7 mmol), triethylamine (5.63 g, 55.6 mmol), 4 Å molecular sieves (15.0 g) dichloromethane (300 mL) is stirred at room temperature for 4 d. The reaction mixture is filtered through a pad of Celite and the filtrate is washed with water, with 2N aq hydrochloric acid, with sat aq sodium bicarbonate, with brine, dried, filtered and concentrated. The residue is purified by chromatography eluting with dichloromethane. Product containing fractions are combined and concentrated to afford 2-chloro-1-phenyl-1H-indole-3-carboxaldehyde (4.40 g, 88% yield) as a yellow solid. NMR (CDCl$_3$) 12.30 (1H, s), 8.37 (1H, d), 7.58-7.70 (3H, m), 7.43 (2H, d), 7.23-7.40 (2H, m), 7.10 (1H, d).

Preparation 5

5-Methyl-1-phenyl-1H-indole-2,3-dione

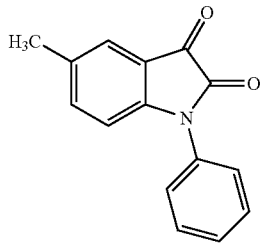

A mixture of 5-methyl-1H-indole-2,3-dione (5-methylisatin, 2.0 g, 12.41 mmol), phenylboronic acid (3.027 g, 24.82 mmol), anhyd cupric acetate (4.50 g, 24.77 mmol), activated 4A molecular sieve (6.6 g), triethylamine (3.47 mL, 24.9 mmol), pyridine (2.01 mL, 24.9 mmol) and dichloromethane (165 mL) is stirred for 24 hr at room temperature. The mixture is filtered through a pad of hyflo and evaporated. The residue is stirred with ethyl acetate, the insoluble copper salts removed by filtration and the filtrate is evaporated. The residue is purified by flash chromatography eluting with dichloromethane to give the title compound (1.91 g, 65% yield) as an orange solid. MS 238 (M+H).

Preparation 6

1-(4-Pyridyl)-1H-indole-2,3-dione

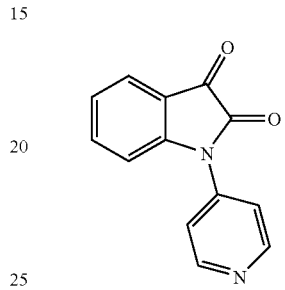

A mixture of 1H-indole-2,3-dione (isatin, 552 mg, 3.75 mmol), pyridine-4-boronic acid (922 mg, 7.5 mmol), anhyd cupric acetate (1.36 mg, 7.5 mmol), activated 4A molecular sieve (2.0 g), triethylamine (1.05 mL, 7.5 mmol), pyridine (607 μL, 7.5 mmol) and dichloromethane (50 mL) is stirred for 24 hr at room temperature. The mixture is filtered through a pad of hyflo and evaporated. The residue is stirred with ethyl acetate, the insoluble copper salts removed by filtration and the filtrate is evaporated. The residue is purified by flash chromatography eluting with pentne-30 to 80% ethyl acetate to give the title compound.

Preparation 7

1-Phenyl-1H-indol-2-one

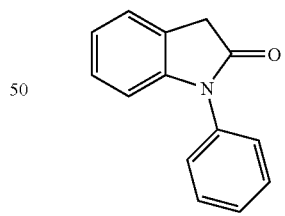

To a solution of commercially available 1-phenyl-1H-indole-2,3-dione (10.10 g, 45.7 mmol) in ethylene glycol (125 mL) is added powdered potassium hydroxide (7.4 g, 112 mmol), hydrazine hydrate (16.35 mL) and water (4 mL). The reaction is heated to 160° C. for 1.5 hr after which it is cooled to room temperature, made acidic with conc. hydrochloric acid, diluted with water and the resulting solids are collected by filtration. The solid is washed with water, dissolved in dichloromethane, dried and the solvent removed to give the 1-phenyl-1H-indol-2-one (8.6 g, 90% yield) as a solid.

Preparation 8

5-Methyl-1-phenyl-1H-indol-2-one

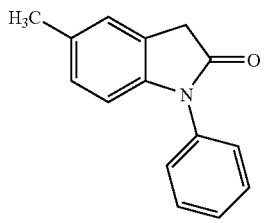

A suspension of 1-phenyl-1H-indole-2,3-dione (1.908 g, 11.83 mmol) in ethylene glycol (30 mL) is treated with powdered potassium hydroxide (1.92 g, 112 mmol), hydrazine hydrate (16.35 mL) and water (4 mL) as described hereinabove. The crude product is purified by flash chromatography eluting with dichloromethane. Product containing fractions are combined, concentrated and the residue is triturated with pentane to afford 5-methyl-1-phenyl-1H-indol-2-one as an off-white solid. MS 224 (M+1)

Preparation 9

2-Chloro-1-methyl-1H-indole-3-carboxaldehyde

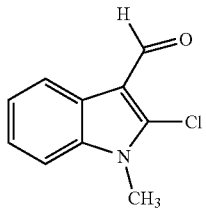

A solution of 2-chloro-1H-indole-3-carboxaldehyde (1.0 g, 5.5 mmol) in DMF (30 mL) is treated portionwise over 10 min with 60% sodium hydride (440 mg, 11 mmol). After stirring for 30 min, methyl iodide (685 µL, 11 mmol) is slowly added and the resulting mixture is stirred 3 hr at room temperature. Water (5 mL) is cautiously added and the solvents are removed. The residue is dissolved in ethyl acetate and washed with water, with brine, dried, filtered and concentrated to give 2-chloro-1-methyl-1H-indole-3-carboxaldehyde (1.16 g, 105%), mp 94.5-95.5° C., as a white solid. MS 194 (M+H).

Preparation 10

2-Chloro-1-benzyl-1H-indole-3-carboxaldehyde

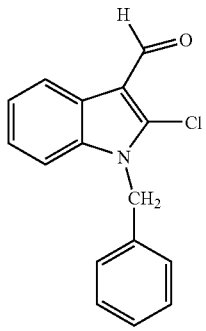

The procedure of PREPARATION 9 is essentially repeated in this preparation except for employing the following two starting materials: 2-Chloro-1H-indole-3-carboxaldehyde (1.0 g, 5.5 mmol) and benzyl bromide (1.88 g, 11 mmol) to yield the title compound (77%) as a white solid. MS 270 (M+H).

Preparation 11

2-Chloro-1-phenyl-1H-pyrrolo[2,3-b]pyridine-3-carbaldehyde

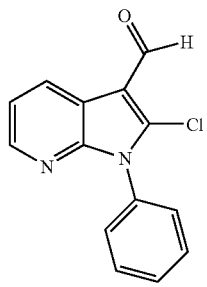

Step 1: 1-Phenyl-7-azaindole: To a mixture of 7-azaindole (550 mg, 4.66 mmol), copper iodide (7.4 mg, 0.038 mmol) and potassium phosphate (1.74 g, 8.18 mmol) under a $N_2$ atmosphere is added racemic trans-1,2-diaminocyclohexane (0.046 mL, 0.38 mmol), iodobenzene (0.436 mL, 3.9 mmol) followed by anhydrous dioxane (5 mL). The resulting suspension is heated in an oil bath at 110° C. with magnetic stirring for 24 hours. The resulting mixture is filtered through a short pad of silica gel, washing the cake well with ethyl acetate. The filtrate is evaporated to leave a brown oil. The residue is purified by flash chromatography on a 10-gram silica gel cartridge by elution with heptane:ethyl acetate (4:1). Fractions containing the product are combined and the solvent evaporated, and further purified by flash chromatography on a 10-gram silica gel cartridge by elution with heptane: ethyl acetate (19:1). Clean fractions containing the product are combined and evaporated to give 758 mg of 1-phenyl-7-azaindole as a light brown oil (100% yield). $^1$H NMR (300 MHz, CDCl$_3$): 8.37 (1H, dd), 7.97 (1H, dd), 7.76 (2H, d), 7.56-7.49 (3H, m), 7.35 (1H, t), 7.13 (1H, dd), 6.63 (1H, d).

Step 2: 3,3-Dibromo-1-phenyl-1,3-dihydro-pyrrolo[2,3-b] pyridin-2-one: A solution of 1-phenyl-7-azaindole (325 mg, 1.68 mmol) in tert-butanol (12 mL) under $N_2$ atmosphere is treated with pyridinium bromide perbromide (2.15 g, 6.71 mmol) portion wise over 3.5 hours, with occasional gentle heating on a hot plate to prevent freezing of the reaction mixture. Part of the way through the addition the mixture crashes out to give a thick orange suspension. The reaction is stirred for an additional 2.5 hours. The reaction mixture is evaporated and the residue is partitioned between water and ethyl acetate. The ethyl acetate layer is separated and washed with 2 further portions of water and a portion of saturated brine, and is dried over magnesium sulfate. Filtering and evaporation gives a orange solid. The crude product is triturated with ether, and the resulting solid separated, and dried under vacuum to give 612 mg of 3,3-dibromo-1-phenyl-1,3-dihydro-pyrrolo[2,3-b]pyridin-2-one as an orange solid (99% yield). MS: m/e 367/369/371 (M+H), 389/391/393 (M+Na). $^1$H NMR (300 MHz, CDCl$_3$): 8.24 (1H, dd), 7.94 (1H, dd), 7.51-7.60 (4H, m), 7.47 (1H, m), 7.18 (1H, dd).

Step 3: 1-Phenyl-1,3-dihydro-pyrrolo[2,3-b]pyridin-2-one: 3,3-dibromo-1-phenyl-1,3-dihydro-pyrrolo[2,3-b]pyridin-2-one (600 mg, 1.63 mmol) and 10% by weight palladium on activated charcoal (300 mg) are suspended in absolute ethanol (60 mL). This mixture is allowed to stir under a hydrogen atmosphere at atmospheric pressure for 17 hours. The reaction mixture is filtered through a pad of hiflo, washing the cake well with ethanol. Concentration of the filtrate gives crude 1-phenyl-1,3-dihydro-pyrrolo[2,3-b]pyridin-2-one as an orange brown solid. This material was used without any further purification. MS: m/e 211 (M+H), 443 (2M+Na).

Step 4: 2-Chloro-1-phenyl-1H-pyrrolo[2,3-b]pyridine-3-carbaldehyde: An ice-acetone cooled solution of anhydrous dimethylformamide (0.71 mL, 9.17 mmol) and anhydrous dichloromethane (1 mL) under a $N_2$ atmosphere is treated drop-wise with phosphorus oxychloride (0.69 mL, 7.42 mmol). The resulting yellowish mixture is continued to stir for 30 mins to give an opaque gel. Crude 1-phenyl-1,3-dihydro-pyrrolo[2,3-b]pyridin-2-one is added portion wise as a solid over 10 minutes to form a red mixture. Further dichloromethane (1 mL) is added followed by pyridine (0.45 mL, 5.56 mmol) to give a dark red mixture. The reaction is allowed to warm slowly to room temperature over 1 hour, and stirred at room temperature for 38 hours. The red reaction mixture is concentrated, and the residue is treated with phosphorus oxychloride (8 mL) and the mixture heated in an oil bath at 110° C. for 3 hours. After concentration of the red mixture, the residue is treated with ice water, and treated with saturated aqueous sodium hydrogen carbonate solution until the effervescence ceases. The mixture is extracted with 5 portions of dichloromethane, the combined extracts are dried over magnesium sulfate, filtered and evaporated to leave an orange solid. The residue is purified by flash chromatography on a 5-gram silica gel cartridge by elution with dichloromethane. Fractions containing the product are combined and the solvent evaporated, and after trituration with heptane gives 220 mg of 2-chloro-1-phenyl-1H-pyrrolo[2,3-b]pyridine-3-carbaldehyde as a fluffy pink solid (53% yield from 3,3-dibromo-1-phenyl-1,3-dihydro-pyrrolo[2,3-b]pyridin-2-one). MS: m/e 257/259 (M+H). $^1$H NMR (300 MHz, CDCl$_3$): 10.24 (1H, s), 8.62 (1H, dd), 8.39 (1H, dd), 7.68-7.56 (3H, m), 7.49 (2H, d), 7.31 (1H, dd).

Preparation 12

2-Chloro-1-pyridin-3-yl-1H-pyrrolo[2,3-b]pyridine-3-carabaldehyde

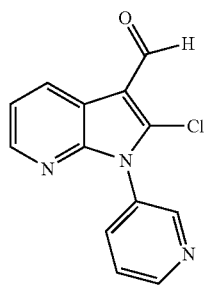

Step 1: 1-Pyridin-3-yl-7-azaindole: To a mixture of 7-azaindole (550 mg, 4.66 mmol), copper iodide (7.4 mg, 0.038 mmol) and potassium phosphate (1.74 g, 8.18 mmol) under a $N_2$ atmosphere is added racemic trans-1,2-diaminocyclohexane (0.046 mL, 0.38 mmol), 3-bromo-pyridine (0.376 mL, 3.9 mmol) followed by anhydrous dioxane (5 mL). The resulting suspension is heated in an oil bath at 110° C. with magnetic stirring for 38 hours. Further copper iodide (65 mg, 0.341 mmol) is added and the resulting mixture heated in an oil bath at 110° C. for 57 hours to give a brown sludgy mixture. Filtration through a short pad of silica gel, washing the cake well with ethyl acetate and evaporation of the filtrate gives the crude product as a dark brown oil. The residue is purified by flash chromatography on a 10-gram silica gel cartridge by elution with heptane:ethyl acetate: dichloromethane (3:1:1, increasing to 32:13:5 and 24:16:10). Fractions containing the product are combined and evaporated to give 818 mg of 1-pyridin-3-yl-7-azaindole as a light brown oil (108% yield). MS: m/e 196 (M+H). $^1$H NMR (300 MHz, CDCl$_3$): 9.01 (1H, br.s), 8.60 (1H, br.s), 8.39 (1H, dd), 8.30 (1H, d), 8.00 (1H, dd), 7.55 (1H, d), 7.49 (1H, dd), 7.18 (1H, dd), 6.70 (1H, d).

Step 2: 3,3-Dibromo-1-pyridin-3-yl-1,3-dihydro-pyrrolo[2,3-b]pyridin-2-one: A solution of 1-pyridin-3-yl-7-azaindole (crude, 800 mg, 4.10 mmol) in tert-butanol (40 mL) under $N_2$ atmosphere is treated with pyridinium bromide perbromide (4.36 g, 13.6 mmol) portion wise over 2.75 hours, with occasional gentle heating on a hot plate to prevent freezing of the reaction mixture. Part of the way through the addition the mixture crashes out to give a thick orange suspension. The reaction is stirred for an additional 3 hours. The reaction mixture is evaporated and the residue is partitioned between water and ethyl acetate. The ethyl acetate layer is separated and washed with 2 further portions of water and a portion of saturated brine, and is dried over magnesium sulfate. Filtering and evaporation gives a crunchy brown solid. The crude product is triturated with ether, and the resulting solid separated, and dried under vacuum to give 2.12 g of crude 3,3-dibromo-1-pyridin-3-yl-1,3-dihydro-pyrrolo[2,3-b]pyridin-2-one (140% yield). MS: m/e 368/370/372 (M+H). $^1$H NMR (300 MHz, DMSO-d$_6$): 9.03 (1H, br.s), 8.81 (1H, m), 8.40 (1H, m), 8.31 (1H, d), 8.24 (1H, d), 7.89 (1H, dd), 7.41 (1H, dd).

Step 3: 1-Pyridin-3-yl-1,3-dihydro-pyrrolo[2,3-b]pyridin-2-one: 3,3-dibromo-1-pyridin-3-yl-1,3-dihydro-pyrrolo[2,3-b]pyridin-2-one (crude, 2.12 g) and 10% by weight palladium on activated charcoal (750 mg) are suspended in absolute ethanol (85 mL). This mixture is allowed to stir under a hydrogen atmosphere at atmospheric pressure for 19 hours. The reaction mixture is filtered through a pad of hiflo, washing the cake well with copious amounts of boiling ethanol. Concentration of the filtrate gives crude 1-pyridin-3-yl-1,3-dihydro-pyrrolo[2,3-b]pyridin-2-one as an sticky brown solid. Saturated aqueous sodium hydrogen carbonate (30 mL) is added and the mixture extracted with 8 portions of dichloromethane. The combined extracts are dried over magnesium sulfate, filtered and evaporated to give a brown residue. The crude material is purified by flash chromatography on a 5-gram silica gel cartridge by elution with dichloromethane: methanol (99:1). Fractions containing the product are combined and evaporated to give 380 mg of 1-pyridin-3-yl-1,3-dihydro-pyrrolo[2,3-b]pyridin-2-one (47% yield starting from 3-bromopyridine). MS: m/e 212 (M+H). $^1$H NMR (300 MHz, CDCl$_3$): 8.90 (1H, d), 8.62 (1H, dd), 8.19 (1H, d), 7.96 (1H, dt), 7.61 (1H, d), 7.47 (1H, dd), 7.08 (1H, dd), 3.78 (2H, s).

Step 4: 2-Chloro-1-pyridin-3-yl-1H-pyrrolo[2,3-b]pyridine-3-carbaldehyde: An ice-acetone cooled solution of anhydrous dimethylformamide (0.71 mL, 9.2 mmol) and anhydrous dichloromethane (2 mL) under a $N_2$ atmosphere is treated drop-wise with phosphorus oxychloride (0.93 mL, 10 mmol). The resulting yellowish mixture is continued to stir for 40 mins to give a cloudy mixture. A solution of 1-pyridin-3-yl-1,3-dihydro-pyrrolo[2,3-b]pyridin-2-one (370 mg, 1.75 mmol) and pyridine (0.30 mL, 3.7 mmol) in dichloromethane (1 mL) is added drop-wise over 20 minutes to form a red mixture. The reaction is allowed to warm slowly to room temperature over 1 hour, and stirred at room temperature for 24 hours. The red reaction mixture is concentrated, and the residue is treated with phosphorus oxychloride (10 mL) and the mixture heated in an oil bath at 110° C. for 3 hours. After concentration of the red mixture, the residue is treated with ice water, and treated with saturated aqueous sodium hydrogen carbonate solution until the effervescence ceases. The mixture is extracted with 5 portions of dichloromethane, the combined extracts are dried over magnesium sulfate, filtered and evaporated to leave a brown solid. The residue is purified by flash chromatography on a 10-gram silica gel cartridge by elution with dichloromethane. Fractions containing the product are combined and the solvent evaporated, and the residue is purified by flash chromatography on a 10-gram silica gel cartridge by elution with dichloromethane. After trituration with heptane 36 mg of 2-chloro-1-pyridin-3-yl-1H-pyrrolo[2,3-b]pyridine-3-carbaldehyde is obtained as a fluffy cream powder. A further 11 mg of product is obtained by purifying the heptane supernatant by flash chromatography on a 5-gram silica gel cartridge by elution with dichloromethane:methanol (99:1) increasing to ethyl acetate. Total yield, 47 mg, 10% yield. MS: m/e 258/260 (M+H).

Example 1

1-Phenyl-2-(thiomorphin-4-yl)-1H-indole-3-carboxaldehyde

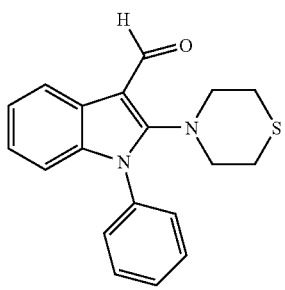

A solution of 2-chloro-1-phenyl-1H-indole-3-carboxaldehyde (130 mg, 0.51 mmol) and thiomorpholine (105 mg, 1.02 mmol) in dioxane (6 mL) is refluxed for 10 hr. The solvent is removed and the residue is purified by chromatography eluting with dichloromethane to afford 1-phenyl-2-(thiomorphin-4-yl)-1H-indole-3-carboxaldehyde (135 mg, 82% yield) as a yellow solid. MS 323 (M+H); NMR (CDCl$_3$) 8.30 (1H, d), 7.5-7.70 (3H, m), 7.40 (2H, d), 7.28 (1H, t), 7.19 (1H, t), 6.98 (1H, d), 3.55 (4H, t), 2.46 (4H, t).

Example 2
2-[4-(2-Hydroxyethyl)piperazin-1-yl]-1-phenyl-1H-indol-2-one

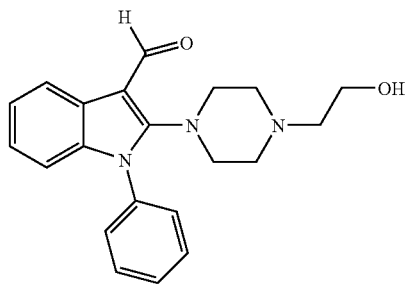

2-Chloro-1-phenyl-1H-indole-3-carboxaldehyde (2.55 g, 19.6 mmol), 4-(2-hydroxyethyl)-piperazine (1.00 g, 3.92 mmol) in dioxane (13 mL) is heated overnight at reflux. The cooled reaction is diluted with water and extracted with dichloromethane. The organic layer is dried, filtered and evaporated to a semi-solid that is triturated with ether to give the 2-[4-(2-hydroxyethyl)piperazin-1-yl]-1-phenyl-1H-indole-3-carboxaldehyde as a brownish solid. MS 350 (M+H).

Example 3
2-(piperazin-1-yl)-1-phenyl-1H-indole-3-carboxaldehyde

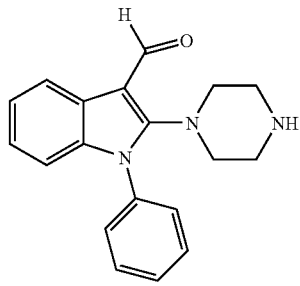

A mixture of 2-chloro-1-phenyl-1H-indole-3-carboxaldehyde (2.0 g, 7.83 mmol), piperazine (6.73 g, 78.3 mmol) and dioxane (25 mL) is heated at reflux overnight. After cooling to room temperature, water (100 mL) is added and after 1 hr the solids are collected by filtration, washed with water and purified by flash chromatography eluting with chloroform-5% methanol. Product containing fractions are combined and concentrated to afford 2-(piperazin-1-yl)-1-phenyl-1H-indol-3-carboxaldehyde (0.87 g, 36%) as a beige solid. A sample, mp 175° C., is purified by flash chromatography eluting with dichloromethane-5% methanol. NMR (CDCl$_3$) 10.29 (1H, s), 8.27 (1H, d), 7.60 (2H, m), 7.51 (1H, t), 7.40 (2H, d), 7.23 (1H, m), 7.15 (1H, t), 6.98 (1H, d), 3.27 (4H, m), 2.78 (4H, m).

Example 4
5-methyl-1-phenyl-2-(piperazin-1-yl)-1H-indole-3-carboxaldehyde

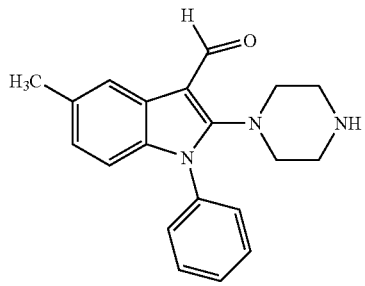

2-Chloro-5-methyl-1-phenyl-1H-indole-3-carboxaldehyde is reacted with piperazine as described in Example 2 to give 5-methyl-1-phenyl-2-(piperazin-1-yl)-1H-indole-3-carboxaldehyde as a pale yellow solid (63% yield).

Example 5

2-(2-Dimethylaminoethylamino)-1-phenyl-1H-indole-3-carboxaldehyde

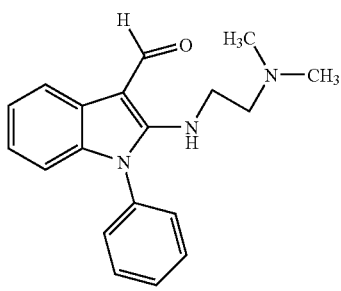

2-Chloro-1-phenyl-1H-indole-3-carboxaldehyde is reacted with N,N-dimethylethanediamine as described in Example 2 to give the title compound as a beige solid (42% yield). NMR (CDCl$_3$) 10.0 (1H, s), 7.73 (1H, br s), 7.59 (4H, m), 7.42 (2H, m), 7.18 (1H, t), 7.0 (1H, t), 6.77 (1H, d), 2.98 (2H, br), 2.38 (2H, br t), 2.12 (6H, s).

Example 6

2-(Piperidin-1-yl)-1-phenyl-1H-indole-3-carboxaldehyde

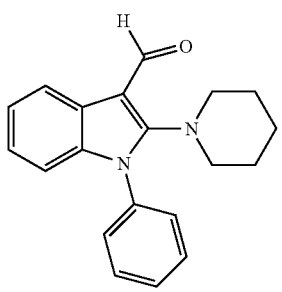

2-Chloro-1-phenyl-1H-indole-3-carboxaldehyde is reacted with piperidine as described in Example 2 to give, after flash chromatography, the title compound (50% yield). NMR (CDCl$_3$) 10.23 (1H, s), 8.29 (1H, d), 7.59 (2H, m), 7.50 (1H, m), 7.40 (2H, d), 7.22 (1H, m), 7.11 (1H, t), 6.98 (1H, d), 3.25 (4H, m), 1.53 (2H, m), 1.42 (4H, m).

Example 7

2-(Azepan-1-yl)-1-phenyl-1H-indole-3-carboxaldehyde

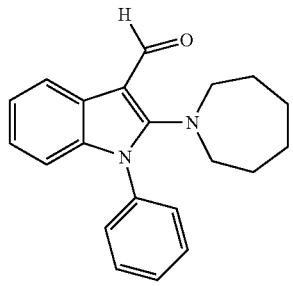

2-Chloro-1-phenyl-1H-indole-3-carboxaldehyde is reacted with azepane as described in Example 2 to give the title compound (42% yield). NMR (CDCl$_3$) 10.25 (1H, s), 8.23 (1H, d), 7.58 (2H, m), 7.51 (1H, m), 7.39 (2H, d), 7.25 (1H, m), 7.15 (1H, t), 6.98 (1H, d), 3.50 (4H, m), 2.55 (4H, m), 2.33 (3H, s), 1.78 (2H, m).

Example 8

2-[(Methylpiperidin-4-yl)amino]-1-phenyl-1H-indole-3-carboxaldehyde

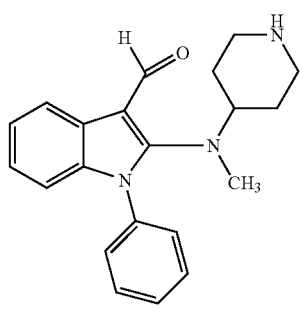

2-Chloro-1-phenyl-1H-indole-3-carboxaldehyde is reacted with 4-methylamino-piperidine-1-carboxylic acid tert-butyl ester as described in Example 2 to give the title compound (18% yield). LC-RT 2.20 min.; MS 334 (M+H).

Example 9

2-(piperazin-1-yl)-1-methyl-1H-indole-3-carboxaldehyde

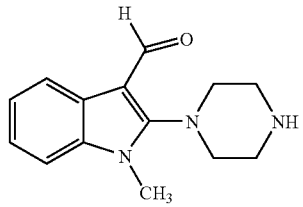

2-Chloro-1-methyl-1H-indole-3-carboxaldehyde (1.0 g, 5.5 mmol) is reacted with piperazine as described in Example 2 to yield the title compound (24%) as an orange-brown solid. MS 244 (M+H).

Example 10

2-(piperazin-1-yl)-1-benzyl-1H-indole-3-carboxaldehyde

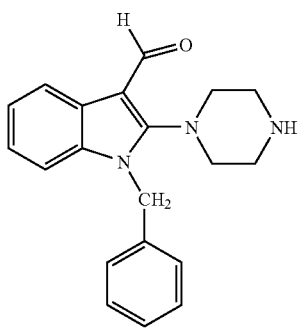

2-Chloro-1-benzyl-1H-indole-3-carboxaldehyde (1.0 g, 5.5 mmol) is reacted with piperazine as described in Example 2 to yield the title compound (64%), mp 163-165° C., as a pale yellow solid. MS 320 (M+H).

Example 11

2-(piperazin-1-yl)-1-aryl-1H-indole-3-carboxaldehyde

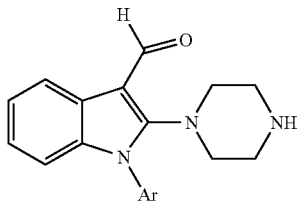

A series of aryl substituted title compounds are synthesized in two steps following the procedure as set forth below in a parallel fashion.

Step A: 2-chloro-1-aryl-1H-indole-3-carboxaldehyde

In 11 sealable reaction tubes are placed 2-chloro-1H-indole-3-carboxaldehyde (200 mg, 1.1 mmol), cupric acetate (400 mg, 2.2 mmol), 4A molecular sieves (587 mg), the required arylboronic acid (2.2 mmol), dichloromethane (15 mL), triethylamine (308 μL, 2.2 mmol) and pyridine (178 μL, 2.2 mmol) and the reaction mixtures are stirred at room temperature for 36 hr. They are diluted with ether, filtered through Hiflo and the filtrates are concentrated. The residues are purified by chromatography eluting with pentane-10% ethyl acetate to afford the corresponding 2-chloro-1-aryl-1H-indole-3-carboxaldehyde. The resulting product and the yield in each of these 11 examples are tabulated in Table 1.

TABLE 1

| Example No. | Product | Yield (%) |
|---|---|---|
| Example 11A-1 | 2-chloro-1-(3-nitrophenyl)-1H-indole-3-carboxaldehyde | 78 |
| Example 11A-2 | 2-chloro-1-(1-naphthyl)-1H-indole-3-carboxaldehyde | 29 |
| Example 11A-3 | 2-chloro-1-(4-methoxyphenyl)-1H-indole-3-carboxaldehyde | 46 |
| Example 11A-4 | 2-chloro-1-(4-tert-butylphenyl)-1H-indole-3-carboxaldehyde | 30 |
| Example 11A-5 | 2-chloro-1-(4-bromophenyl)-1H-indole-3-carboxaldehyde | 42 |
| Example 11A-6 | 2-chloro-1-(4-chlorophenyl)-1H-indole-3-carboxaldehyde | 61 |
| Example 11A-7 | 2-chloro-1-(3-chloro-4-fluorophenyl)-1H-indole-3-carboxaldehyde | 66 |
| Example 11A-8 | 2-chloro-1-(3-methoxyphenyl)-1H-indole-3-carboxaldehyde | 35 |
| Example 11A-9 | 2-chloro-1-(4-thiomethylphenyl)-1H-indole-3-carboxaldehyde | 16 |
| Example 11A-10 | 2-chloro-1-(3-fluorophenyl)-1H-indole-3-carboxaldehyde | 67 |
| Example 11A-11 | 2-chloro-1-(3-methylphenyl)-1H-indole-3-carboxaldehyde | 46 |

Step B: 2-(piperazin-1-yl)-1-aryl-1H-indole-3-carboxaldehyde

In 11 reaction tubes are placed 2-chloro-1-aryl-1H-indole-3-carboxaldehyde obtained from Step A, piperazine (860 mg, 10 mmol) and dioxane (10 mL) and the solutions are heated at reflux temperature for 36 hr. After cooling to room temperature, water is added and the mixtures are extracted with ethyl acetate. The extracts are washed with water, with saline, dried, filtered and concentrated. The crude 2-(piperazin-1-yl)-1-aryl-1H-indole-3-carboxaldehydes are purified by flash chromatography eluting with dichloromethane-10% methanol. The resulting product and the yield in each of these 11 examples are tabulated in Table 2. All of the listed final products exhibited characteristic $^1$H NMR spectra.

TABLE 2

| Example No. | Product | Yield (mg) |
|---|---|---|
| Example 11B-1 | 2-(Piperazin-1-yl)-1-(3-nitrophenyl)-1H-indole-3-carboxaldehyde | 25 |
| Example 11B-2 | 2-(Piperazin-1-yl)-1-(1-naphthyl)-1H-indole-3-carboxaldehyde | 32 |
| Example 11B-3 | 2-(Piperazin-1-yl)-1-(4-methoxyphenyl)-1H-indole-3-carboxaldehyde | 93 |
| Example 11B-4 | 2-(Piperazin-1-yl)-1-(4-tert-butylphenyl)-1H-indole-3-carboxaldehyde | 61 |
| Example 11B-5 | 2-(Piperazin-1-yl)-1-(4-bromophenyl)-1H-indole-3-carboxaldehyde | 80 |
| Example 11B-6 | 2-(Piperazin-1-yl)-1-(4-chlorophenyl)-1H-indole-3-carboxaldehyde | 110 |
| Example 11B-7 | 2-(Piperazin-1-yl)-1-(3-chloro-4-fluorophenyl)-1H-indole-3-carboxaldehyde | 35 |
| Example 11B-8 | 2-(Piperazin-1-yl)-1-(3-methoxyphenyl)-1H-indole-3-carboxaldehyde | 55 |
| Example 11B-9 | 2-(Piperazin-1-yl)-1-(4-thiomethylphenyl)-1H-indole-3-carboxaldehyde | 32 |
| Example 11B-10 | 2-(Piperazin-1-yl)-1-(3-fluorophenyl)-1H-indole-3-carboxaldehyde | 88 |
| Example 11B-11 | 2-(Piperazin-1-yl)-1-(3-methylphenyl)-1H-indole-3-carboxaldehyde | 72 |

Example 12

2-(Piperazin-1-yl)-1'-(thien-3-yl)-1H-indole-3-carboxaldhyde

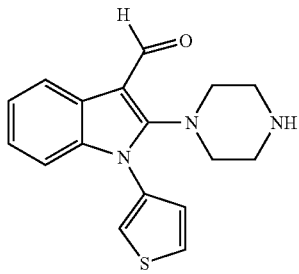

Step 1: 1-(Thien-3-yl)-1H-indole

A mixture of indole (5.64 g, 48.3 mmol), 3-bromothiophene (4.84 mL, 51.6 mmol), potassium carbonate (7.16 g, 51.6 mmol), cuprous bromide (298 mg, 2.1 mmol) and N-methylpyrrolidinone (57 mL) is stirred at 180° C. under nitrogen atmosphere for 48 hr. After cooling to room temperature, the reaction mixture is poured into water (300 mL) and then extracted with ethyl acetate. The extract is washed with water, with brine, dried, filtered and concentrated to give a brown oil that is purified by chromatography eluting with heptane-10% dichloromethane. Product containing fraction are combined and concentrated to afford 1-(thien-3-yl)-1H-indole (6.20 g, 64% yield) as a colorless oil.

Step 2: 1-(Thien-3-yl)-1H-indol-2-one

A solution of the above 1-(thien-3-yl)-1H-indole (6.10 g, 30.6 mmol), N-chlorosuccinimide (4.30 g, 32.2 mmol) and dichloromethane (230 mL) is stirred for 2 hr at room temperature. The solvent is then removed, the residue is dissolved in acetic acid (127 mL) and heated to 70° C. Then 85% phosphoric acid is added and the reaction mixture is heated at gentle reflux for 24 hr. After cooling to room temperature, the reaction is concentrated to about its volume, poured onto ice and water and extracted with ethyl acetate. The combined extract is washed with water, with brine, dried, filtered and concentrated. The black residue is purified by chromatography eluting with dichloromethane-0 to 5% methanol. Product containing fractions are combined and concentrated to afford 1-(thien-3-yl)-1H-indol-2-one (4.12 g, 63% yield) as a brown solid.

MS 216 (M+H).

Step 3: 2-chloro-1-(thien-3-yl)-1H-indole-3-carboxaldehyde

Phosphorous oxychloride (1.9 mL, 20.9 mmol) is added slowly to a stirred solution of dimethylformamide (2 mL) and dichloromethane (2 mL) cooled to 0-5° C. After 5 min a solution of the above 1-(thien-3-yl)-1H-indol-2-one (1.0 g, 2.65 mmol), pyridine (1 mL) and dichloromethane (4 mL) is added and the reaction is stirred at room temperature for 48 hr. The reaction mixture is poured into ice/water and extracted with ethyl acetate. Some solids are removed by filtration and the organic layer is separated, dried, filtered and concentrated. The residue is purified by chromatography eluting with pentane-10% ethyl acetate. Product containing fraction are combined and concentrated to afford 2-chloro-1-(thien-3-yl)-1H-indole-3-carboxaldehyde (694 mg, 57%) as a light orange solid. MS 262 (M+H).

Step 4: 2-(Piperazin-1-yl)-1-(thien-3-yl)-1H-indole-3-carboxaldehyde

2-Chloro-1-(thien-3-yl)-1H-indole-3-carboxaldehyde as prepared above is reacted with piperazine as described in Example 3 to give the title compound as a pale yellow solid (78% yield). MS 409 (M+H)

Example 13

2-(piperazin-1-yl)-1-(pyridin-3-yl)-1H-indole-3-carboxaldehyde

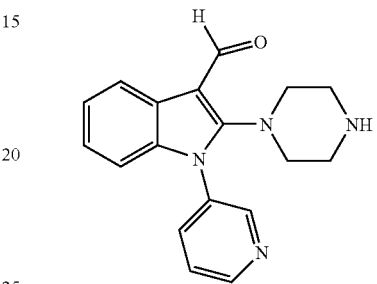

Step 1: 1-(pyridin-3-yl)-1H-indole

Under an argon atmosphere, a solution of bromopyridine (1.7 mL, 17.6 mmol) in toluene (15 mL) is added to indole (2.0 g, 17.1 mmol), tris(dibenzylideneacetone)palladium (480 mg, 0.52 mmol), 2-(di-tert-butylphosphino)biphenyl (5.52 mg, 0.76 mmol), sodium tert-butoxide and toluene (25 mL) and the stirred mixture is heated at 100° C. for 48 hr. After cooling to room temperature, ether is added and the reaction mixture is filtered through Hi-Flo and concentrated. The residue is purified by chromatography eluting with pentane-25% ethyl acetate. Product containing fractions are combined and concentrated to afford 1-(pyridin-3-yl)-1H-indole (485 mg, 15%) as a yellow-brown oil.

Step 2: 1-(pyridin-3-yl)-1,3-dihydroindol-2-one

1-(pyridin-3-yl)-1H-indole is reacted with N-chlorosuccinimide as described in Example 12 to give 1-(pyridin-3-yl)-1,3-dihydroindol-2-one (59% yield) as a light brown solid.

Step 3: 2-chloro-1-(pyridin-3-yl)-1,3-dihydroindole-3-carboxaldehyde

Phosphorous oxychloride (500 μL, 5.39 mmol) is added slowly to a stirred solution of dimethylformamide (516 μL) in dichloromethane (516 μL) at 0-5° C. After 15 min, a solution of 1-(pyridin-3-yl)-1,3-dihydroindol-2-one (250 mg, 1.2 mmol) and pyridine (258 μL) in dichloromethane (2 mL) is added. The reaction mixture is warmed to room temperature and stirred for 24 hr. The reaction is diluted with water, made basic with ammonium hydroxide, extracted with dichloromethane and the extract is concentrated. The residue is treated with phosphorous oxychloride (5 mL) and heated at reflux for 2 hr. After cooling to room temperature, the excess phosphorous oxychloride is removed and the residue is treated with ice/water, made basic with ammonium hydroxide and extracted with dichloromethane. The combined extract is washed with brine, dried, filtered and concentrated. The residue is purified by chromatography eluting with pentane-30% ethyl acetate. Product containing fractions are combined and concentrated to afford 2-chloro-1-(pyridin-3-yl)-1,3-dihydroindole-3-carboxaldehyde (42 mg, 14% yield) as a yellow solid.

MS 257 (M+H).

Step 4: 2-(piperazin-1-yl)-1-(pyridin-3-yl)-1H-indole-3-carboxaldehyde 2-chloro-1-(pyridin-3-yl)-1,3-dihydroindole-3-carboxaldehyde is reacted with piperazine as described in Example 2 to give, after flash chromatography, the title compound (23% yield).

Example 14

1-Phenyl-2-(piperazin-1-yl)-13-dihydropyrrolo[2,3-b]pyridine-3-carboxaldehyde

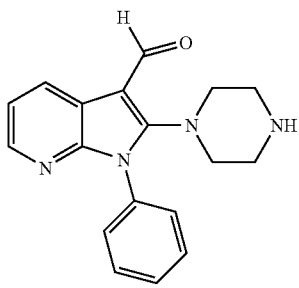

Step 1: (1-oxypyridin-3-yl)acetonitrile

The title compound is prepared in accordance with the procedures as outlined in S. Okuda et al., *J. Am. Chem. Soc.*, 81, 740, (1959). Peracetic acid (38%, 40 mL, 0.2 mol) is added to a stirred solution of 3-pyridylacetonitrile (15.0 g, 127 mmol) in acetic acid (75 mL) and the reaction is heated at 95° C. for 24 hr, then stirred at room temperature for 24 hr. Water is added and the solvents are removed. More water (100 mL) is added and again removed. This process is repeated with toluene and with ether to give (1-oxypyridin-3-yl)acetonitrile as a cream solid.

Step 2: (2-chloropyridin-3-yl)acetonitrile (1-oxypyridin-3-yl)acetonitrile (7.5 g, 35.9 mmol) is carefully added to vigorously stirred phosphorous oxychloride (100 mL). The mixture is slowly heated to 80° C. (in 5° C. increments) over 1.5 hr. (CAUTION. If heating is too quick, violent decomposition occurs at ca 70° C.) All the solids dissolved. The reaction is heated at reflux for 3 hr. The excess phosphorous oxychloride is removed and the residue is cautiously treated with cold water. Saturated sodium bicarbonate is added to make the mixture basic, then it is extracted with ethyl acetate (3×). The combined extract is washed with brine, dried, filtered and concentrated. The residue is purified by chromatography eluting with pentane-10 to 100% ether. The second compound off the column is the desired (2-chloropyridin-3-yl)acetonitrile (2.35 g, 42.9% yield) a light brown solid.

Step 3: (2-Chloropyridin-3-yl)acetic acid:

(2-Chloropyridin-3-yl)acetonitrile (1.0 g, 6.55 mmol) in conc. hydrochloric acid (15 mL) is stirred at 100° C. for 2 hr. After cooling to room temperature the reaction mixture is diluted with water and the solution is concentrated to dryness. The residue is dissolved in water, made basic with ammonium hydroxide, re-acidified with acetic acid and extracted with ethyl acetate. The combined extract is washed with brine, dried, filtered and concentrated to give (2-chloropyridin-3-yl)acetic acid (442 mg, 39%) as a white solid.

Step 4: 1-Phenyl-1,3-dihydropyrrolo[2,3-b]pyridin-2-one:

The title compound is synthesized following the procedures of Ting, P. C. et al., *J. Med. Chem.*, 33, 2697 (1990), as follows. A stirred mixture of (2-chloropyridin-3-yl)acetic (400 mg, 2.3 mmol), aniline (456 μL, 5.0 mmol), tosic acid (10 mg) and pentanol (5 mL) is heated at reflux for 24 hr. After cooling to room temperature, water (80 mL) is added and the mixture is extracted with ethyl acetate-25% dichloromethane. The organic layer is separated, dried, filtered and concentrated. The residue is purified by chromatography eluting with dichloromethane-0 to 5% methanol. The product containing fractions are combined and concentrated to afford 1-phenyl-1,3-dihydropyrrolo[2,3-b]pyridin-2-one (356 mg, 76%) as a light brown solid. MS 211 (M+H).

Step 5: 3-Dimethylaminomethylene-1,3-dihydropyrrolo[2,3-b]pyridin-2-one:

Phosphorous oxychloride (693 μL, 7.47 mmol) is added slowly to a stirred solution of dimethylformamide (714 μL) and dichloromethane (714 μL) cooled to 0-5° C. After 10 min, a solution of the above 1-phenyl-1,3-dihydropyrrolo[2,3-b]pyridin-2-one (350 mg, 1.66 mmol), pyridine (357 μL) and dichloromethane (1.43 mL) is added and the reaction is stirred at room temperature for 24 hr. The reaction mixture is poured into water, the pH adjusted to 8 with ammonium hydroxide and extracted with dichloromethane (2×). The combined extract is dried, filtered and concentrated. The residue is purified by chromatography eluting with dichlormethane-2% methanol. Product containing fractions are combined and concentrated to afford 3-dimethylaminomethylene-1,3-dihydropyrrolo[2,3-b]pyridin-2-one (211 mg, 47.9% yield).

Step 6: 2-chloro-1-phenyl-1,3-dihydropyrrolo[2,3-b]pyridine-3-carboxaldehyde:

3-Dimethylaminomethylene-1,3-dihydropyrrolo[2,3-b]pyridin-2-one (210 mg, 0.79 mmol) is treated with phosphorous oxychloride (10 mL) and stirred at reflux for 2 hr. The excess phosphorous oxychloride is removed and the residue is treated with ice/water and extracted with ethyl acetate. The combined extract is washed with water, with brine, dried, filtered and concentrated to give 2-chloro-1-phenyl-1,3-dihydropyrrolo[2,3-b]pyridine-3-carboxaldehyde (231 mg). MS 257 (M+H).

Step 7: 1-Phenyl-2-(piperazin-1-yl)-1,3-dihydropyrrolo[2,3-b]pyridine-3-carboxaldehyde:

2-Chloro-1-phenyl-1,3-dihydropyrrolo[2,3-b]pyridine-3-carboxaldehyde is reacted with piperazine as described in Example 2 to give 1-phenyl-2-(piperazin-1-yl)-1,3-dihydropyrrolo[2,3-b]pyridine-3-carboxaldehyde (63% yield).

Example 15

1-Phenyl-2-(piperazin-1-yl)-1H-pyrrolo[2,3-c]pyridine-3-carboxaldehyde

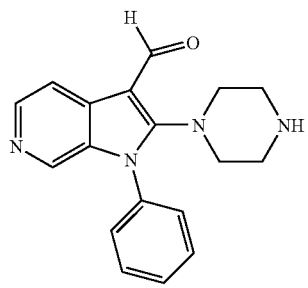

Step 1: 4-chloro-3-nitropyridine:

4-Hydroxy-3-nitropyridine (10.0 g, 71.4 mmol) is added portionwise to a mechanically stirred mixture of phosphorous pentachloride (16.32 g, 78.6 mmol) and phosphorous oxychloride (16.2 mL) at 55-60° C. After the addition is complete, the temperature is raised to 130-140° C. for 4 hr. After cooling to room temperature, the phosphorous oxychloride is removed and the residue is cautiously treated with ice/water, made basic with sodium carbonate and extracted with ether. The combined extract is dried, filtered and concentrated to yield 4-chloro-3-nitropyridine (5.1 g, 45% yield) as a pale yellow solid.

Step 2: 2-(3-Nitropyridin-4-yl)malonic acid dibenzyl ester:

The title compound is prepared following the procedures of Daisley, R. W.; Hanbali, J. R. *Synth. Commun.*, 763, (1981) as follows. Dibenzyl malonate (3.47 mL, 13.9 mmol) is added dropwise to a stirred mixture of 60% oil dispersion of sodium hydride (556 g, 13.9 mmol) in toluene (20 mL). After 1 hr, the mixture is treated with a solution of 4-chloro-3-nitropyridine (2.0 g, 12.6 mmol) in toluene (10 mL) and then heated at reflux for 2 hr. After cooling to room temperature, the reaction is concentrated and the residue is treated with 1M aq hydrochloric acid (6 mL) and extracted with ethyl acetate. The combined extract is washed with saline, dried, filtered and concentrated. The residue is purified by chromatography eluting with pentane-20% ethyl acetate. Product containing fractions are combined and concentrated to give 2-(3-nitropyridin-4-yl)malonic acid dibenzyl ester (1.72 g, 33.6% yield) as a yellow oil.

Step 3: (3-Nitropyridin-4-yl)acetic acid benzyl ester:

The title compound is prepared following the procedures of WO, 00 55159 as follows. A solution of 2-(3-nitropyridin-4-yl)malonic acid dibenzyl ester (1.58 g, 5.6 mmol), lithium chloride (250 mg, 10.6 mmol), dimethylsulfoxide (35 mL) and water (95 mL) is heated at reflux for 8 hr. After cooling to room temperature, the reaction is diluted with water and extracted with ethyl acetate. The combined extract is extracted with water, with brine, dried, filtered and concentrated to yield (3-nitropyridin-4-yl)acetic acid benzyl ester (1.13 g, 99% yield) as a yellow-orange oil. The material is purified by chromatography eluting with pentane-20 to 30% ethyl acetate to afford the product as a pink oil. MS 273 (M+H).

Step 4: (3-Aminopyridin-4-yl)acetic acid benzyl ester:

The title compound is prepared following the procedures of WO, 00 55159 as follows. A mixture of (3-nitropyridin-4-yl)acetic acid benzyl ester (1.10 g, 5.23 mmol), 10% palladium on charcoal (200 mg) and denatured alcohol (100 mL) is stirred under an atmosphere of hydrogen for 6 hr. The catalyst is removed by filtration through a pad of Hi-Flo and the filtrate is concentrated to yield (3-aminopyridin-4-yl)acetic acid benzyl ester (0.92 g, 98% yield) as a yellow-brown oil. MS 181 (M+H).

Step 5: 1,3-Dihydropyrrolo[2,3-c]pyridine-2-one hydrochloride:

The title compound is prepared following the procedures of WO, 00 55159 as follows. A mixture of (3-nitropyridin-4-yl)acetic acid benzyl ester (0.92 g, 5.1 mmol), ether (45 mL) and 10% aq hydrochloric acid (2.5 mL) is stirred vigorously for 18 hr. The organic layer is separated and washed with water (15 mL). The combined water layer and wash is concentrated to yield 1,3-dihydropyrrolo[2,3-b]pyridine-2-one hydrochloride (also known as 6-aza-1,3-dihydroindol-2-one) (790 mg, 91% yield) as a pale yellow solid. MS 135 (M+H).

Step 6: 3-Dimethylaminomethylene-1,3-dihydropyrrolo[2,3-c]pyridin-2-one:

Phosphorous oxychloride (1.93 mL, 3.17 mmol) is added slowly to a stirred solution of dimethylformamide (1.99 mL) and dichloromethane (3 mL) cooled to 0-5° C. After 10 min, a solution of the above 1,3-dihydropyrrolo[2,3-b]pyridine-2-one hydrochloride (6-aza-1,3-dihydroindol-2-one) (790 mg, 4.63 mmol), pyridine (1.5 mL) and dichloromethane (5 mL) is added over 5 min and the reaction is stirred at room temperature for 18 hr. The solvents are removed to yield crude 3-dimethylaminomethylene-1,3-dihydropyrrolo[2,3-b]pyridin-2-one.

Step 7: 2-Chloro-1H-pyrrolo[2,3-c]pyridine-3-carboxaldehyde:

The above crude 3-dimethylaminomethylene-1,3-dihydropyrrolo[2,3-b]pyridin-2-one is treated with phosphorous oxychloride (10 mL) and stirred at reflux for 3 hr. The excess phosphorous oxychloride is removed and the residue is treated with ice/water, made basic with ammonium hydroxide and extracted with dichloromethane. The aqueous layer is concentrated, the residue is dissolved in a small volume of water, saturated with sodium chloride and continuously extracted overnight with ethyl acetate. The organic extract is concentrated and the residue is purified by chromatography eluting with dichloromethane-5% methanol to afford 2-chloro-1H-pyrrolo[2,3-b]pyridine-3-carboxaldehyde (75 mg, 9% yield) as a pale yellow solid. LC-MS: 1.02 min; 181 (M+H).

Step 8: 2-Chloro-1-phenyl-1H-pyrrolo[2,3-c]pyridine-3-carboxaldehyde:

A mixture of 2-chloro-1H-pyrrolo[2,3-b]pyridine-3-carboxaldehyde (70 mg, 0.39 mmol) cupric acetate (140 mg, 0.77 mmol), phenylboronic acid (93 mg, 0.76 mmol), 4A molecular sieve (200 mg), triethylamine (106 µL), pyridine (61 µL) and dichloromethane (5.5 mL) is vigorously stirred at room temperature for 48 hr. The solids are removed by filtration through a pad of Hi-Flo and the filtrate is concentrated. The residue is purified by chromatography eluting with dichloromethane-2% methanol. Product containing fractions are combined and concentrated to give 2-chloro-1-phenyl-1H-pyrrolo[2,3-b]pyridine-3-carboxaldehyde (25 mg, 25% yield) as a pale yellow oil.

Step 9: 1-Phenyl-2-(piperazin-1-yl)-1H-pyrrolo[2,3-c]pyridine-3-carboxaldehyde:

2-Chloro-1-phenyl-1H-pyrrolo[2,3-b]pyridine-3-carboxaldehyde is reacted with piperazine as described in Example 2 to give the title compound as a light brown oil (29.4% yield). LC-MS 0.4 min; 307 (M+H).

Example 16

2-(piperazin-1-yl)-1-phenyl-1H-indole-3-carboxylic acid amide

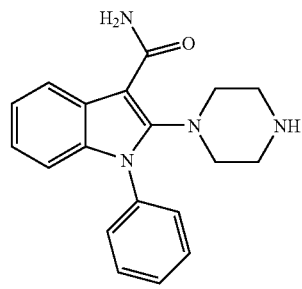

Step 1: 2-Chloro-1-phenyl-1H-indole-2-carboxylic cid:

To a vigorously stirred solution of 2-chloro-1-phenyl-1H-indole-3-carboxaldehyde (4.0 g, 15.6 mmol), 2 M 2-methyl-2-butene (74 mL, 148 mmol) in dioxane (58 mL) at 25° C. is added dropwise over 30 min a solution of sodium chlorite (7.8 g, 86 mmol) and sodium dihydrogenphosphate hydrate (7.8 g, 56 mmol) in water (40 mL). After 2.5 hr, more sodium chlorite (1.92 g, 21.2 mmol) and sodium dihydrogenphosphate hydrate (1.92 g) are added. After 2.5 hr, more sodium chlorite (0.96 g, 10.6 mmol) and sodium dihydrogenphosphate hydrate (0.96 g) are added. After a total reaction time of 6.5 hr, ethyl acetate (100 mL) is added and stirring continued for 45 min. The aqueous layer is separated and extracted with ethyl acetate (2×60 mL). The combined ethyl acetate layer and extracts is concentrated to approximately 80 mL and then extracted with 1% aq. sodium hydroxide (3×150 mL). The combined aqueous extract is made acidic with conc. hydrochloric acid. The resulting solids are collected by filtration, washed with water and crystallized from 2-propanol to afford 2-chloro-1-phenyl-1H-indole-2-carboxylic acid (3.28 g, 77.5% yield) as a pale yellow solid. NMR (CDCl$_3$) 8.30 (1H, d), 7.60 (3H, m), 7.41 (2H, d), 7.38 (1H, t), 7.23 (1H, m), 7.10 (1H, d).

Step 2: 2-Chloro-1-phenyl-1H-indole-2-carboxylic acid amide:

The title compound is prepared in accordance with the procedure set forth in *J. Heterocyclic Chem*. 25, 1519, (1988) as follows. 2-Chloro-1-phenyl-1H-indole-2-carboxylic acid (500 mg, 1.85 mmol) in thionyl chloride (3.6 mL) is refluxed for 6 hr. The unreacted thionyl chloride is removed and the residue is treated with conc. ammonium hydroxide and stirred at over night at room temperature. The solids are collected by filtration and crystallized from ethanol to afford 2-chloro-1-phenyl-1H-indole-2-carboxylic acid amide (300 mg, 60% yield). NMR (CDCl$_3$) 8.39 (1H, d), 7.6 (3H, m), 7.40 (2H, d), 7.35-7.10 (2H, m), 7.05 (1H, d), 6.43 (1H, br s), 5.62 (1H, br s).

Step 3: 2-(piperazin-1-yl)-1-phenyl-1H-indole-3-carboxylic acid amide:

2-Chloro-1-phenyl-1H-indole-2-carboxylic acid amide is reacted with piperazine as described in Example 2 to give the title compound (59% yield) as a white solid. NMR (CDCl$_3$) 8.39 (1H, d), 7.95 (1H, br s), 7.59 (3H, m), 7.4 (2H, m), 7.22 (1H, m), 7.11 (1H, t), 6.8 (1H, d), 5.45 (1H, br s), 3.01 (4H, m), 2.83 (4H, m).

Example 17

2-(piperazin-1-yl)-1-phenyl-1H-indole-3-carboxylic acid methyl ester

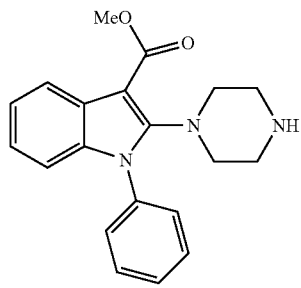

Step 1: 2-Chloro-1-phenyl-1H-indole-2-carboxylic acid methyl ester:

2-Chloro-1-phenyl-1H-indole-2-carboxylic acid (500 mg, 1.85 mmol) in thionyl chloride (3.6 mL) is refluxed for 6 hr. The unreacted thionyl chloride is removed and the residue is treated with methanol (15 mL) and stirred at over night at room temperature. The methanol is removed and the residue is dissolved in dichloromethane, washed with water, dried, filtered and concentrated to give 2-chloro-1-phenyl-1H-indole-2-carboxylic acid methyl ester (450 mg, 85% yield) as an amber oil. NMR (CDCl$_3$) 8.20 (1H, d), 7.60 (3H, m), 7.40 (2H, d), 7.31 (1H, t), 7.21 (1H, m), 7.02 (1H, d), 4.0 (3H, s).

Step 2: 2-(piperazin-1-yl)-1-phenyl-1H-indole-3-carboxylic acid methyl ester:

2-Chloro-1-phenyl-1H-indole-2-carboxylic acid methyl ester is reacted with piperazine as described in Example 2 to give the title compound (69% yield) as a cream solid. NMR (CDCl$_3$) 8.08 (1H, d), 7.58 (2H, m), 7.50 (1H, m), 7.36 (2H, d), 7.22 (1H, t), 7.11 (1H, t), 6.99 (1H, d), 3.98 (3H, s), 3.14 (4H, m), 2.70 (4H, m).

Example 18

2-(4-Oxiranylmethylpiperazin-1-yl)-1-phenyl-1H-indole-3-carboxaldehyde

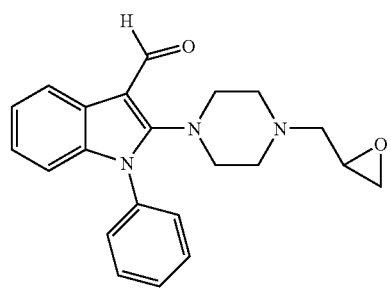

A stirred mixture of 1-phenyl-2-(piperazin-1-yl)-1H-indole-3-carboxaldehyde (438 mg, 1.37 mmol), epibromohydrin (188 mg, 1.37 mmol), potassium carbonate (758 mg, 5.49 mmol) and acetonitrile (20 ml) is heated at reflux for 2.5 hr. The reaction is cooled and the solids are removed by filtration. The filtrate is concentrated and the residue is purified by chromatography eluting with dichloromethane-1 to 5% methanol. Fractions containing the desired product are combined and concentrated to afford 2-(4-oxiranylmethylpiperazin-1-yl)-1-phenyl-1H-indole-3-carboxaldehyde (41% yield) as a yellow solid. LC/MS: MS 376 (M+H); RT 2.65 min; NMR (CDCl$_3$): 10.28 (1H, s), 8.26 (1H, d), 7.43-7.65 (3H, m), 7.17-7.42 (3H, m), 7.13 (1H, t), 6.96 (1H, d), 3.49 (4H, m), 3.03 (1H, m), 2.56-2.86 (4H, m), 2.30-2.50 (2H, m), 1.74 (2H, m), 1.56 (2H, s).

Example 19

{2-[4-(3-Formyl-1-phenyl-2,3-dihydro-1H-indol-2-yl)-piperazin-1-yl]-ethyl}-carbamic acid tert-butyl ester

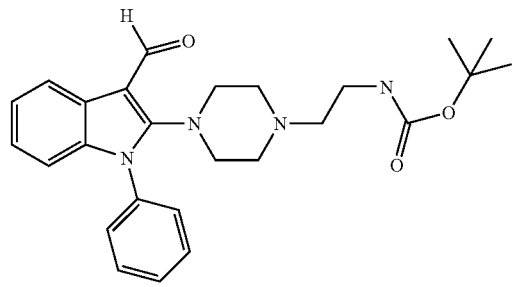

2-Chloro-1-phenyl-1H-indole-3-carboxaldehyde is reacted with 2-(piperizin-1-yl-ethyl)carbamic acid tert-butyl ester as described in Example 1 to afford the title compound (35% yield) as a yellow solid. LC/MS: 449 (M+H); RT 2.77 min; NMR (CDCl$_3$): 10.28 (1H, s), 8.26 (1H, d), 7.48-7.65 (3H, m), 7.38 (2H, d), 7.22-7.26 (1H, m), 7.14(1H, t), 6.96 (1H, d), 3.15-3.50 (8H, m), 2.30-2.50 (4H, m), 1.45(9H, s).

Example 20

4-(3-Formyl-1-phenyl-1H-indole-2-yl)-piperazine-2-carboxylic Acid Methyl Ester

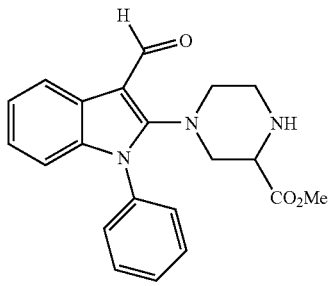

2-Chloro-1-phenyl-1H-indole-3-carboxaldehyde is reacted with piperazine-2-carboxylic acid methyl ester as described in Example 1 to afford 4-(3-formyl-1-phenyl-1H-indole-2-yl)-piperazine-2-carboxylic acid methyl ester (9% yield) as a yellow solid. LC/MS: MS 364 (M+H); RT 2.54 min; NMR (CDCl$_3$): 10.29 (1H, s), 8.26 (1H, d), 7.07-7.65 (m, buried), 6.98 (1H, d), 3.60-4.10 (4H, m), 2.60-3.55 (6H, m).

Example 21

2-(2,5-Diazabicyclo[2.2.1]hept-2-yl)-1-phenyl-1H-indole-3-carboxaldehyde

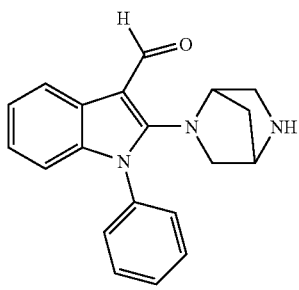

5-diazabicyclo[2.2.1]heptane-2-carboxylic acid tert-butyl ester (275 mg, 0.66 mmol) and trifluoroacetic acid (2 mL) in dichloromethane (1 mL) is stirred overnight at room temperature. The solvent is evaporated and the residue dissolved in dichloromethane (10 mL), washed with 5% aq sodium carbonate, with water, with brine, dried, filtered and concentrated to give 2-(2,5-diazabicyclo[2.2.1]hept-2-yl)-1-phenyl-1H-indole-3-carboxaldehyde (180 mg, 87% yield) as a white solid. MS: 319 (M+H); NMR (CDCl$_3$): 10.30 (1H, s), 8.28 (1H, d), 7.45-7.63 (3H, m), 7.40 (2H, d), 7.23 (1H, d), 7.14 (1H, t), 6.96 (1H, d), 3.20-3.37 (4H, m), 2.70-2.80 (4H, m).

Example 22

2-[1,4]Diazepan-1-yl-1-phenyl-1H-indole-3-carboxaldehyde

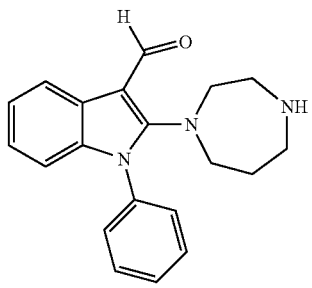

Step 1: 4-(3-formyl-1-henyl-1H-indole-2-yl)-[1,4]diazepane-1-carboxylic acid tert-butyl ester:

2-Chloro-1-phenyl-1H-indole-3-carboxaldehyde is reacted with [1,4]diazepane-1-carboxylic acid tert-butyl ester as described in Example 1 to afford 4-(3-formyl-1-phenyl-1H-indole-2-yl)-[1,4]diazepane-1-carboxylic acid tert-butyl ester (87% yield) as a yellow solid. LC/MS MS 420 (M+H); RT 3.55 min; NMR (CDCl$_3$): 10.25 (1H, s), 8.27 (1 H, d), 7.46-7.66 (3H, m), 7.37 (2H, d), 7.22-7.30 (1H, t), 7.16(1 H, t), 6.96 (1 H, d), 3.25-3.45 (8H, m), 1.56 (2H, m), 1.44(9H, s).

Step 2: 2-[1,4]Diazepan-1-yl-1-phenyl-1H-indole-3-carboxaldehyde:

4-(3-Formyl-1-phenyl-1H-indole-2-yl)-[1,4]diazepan ester (1.06 g, 2.53 mmol) and trifluoroacetic acid (10 mL) in dichloromethane (4 mL) is stirred overnight at room temperature. The solvent is evaporated off and the residue dissolved in dichloromethane (10 mL), washed with 5% aq sodium carbonate, with water, with brine, dried, filtered and concentrated. The residue is purified by chromatography eluting with dichloromethane-5 to 10% methanol. Product containing fraction are combined and concentrated to afford 2-[1,4]diazepan-1-yl-1-phenyl-1H-indole-3-carboxaldehyde (86% yield) as a white solid. LC/MS: MS 320 (M+H); 2.5 min; NMR (CDCl$_3$) 10.30 (1H, s), 8.25 (1H, d), 7.03-7.70 (7H, m), 6.97 (1H, d), 3.20-3.46 (4H, m), 2.84 (4H, m) 1.62(2H, m).

Example 23

2-(4-Formyl-[1,4]diazepan-1-yl)-1-phenyl-1H-indole-3-carboxaldehyde

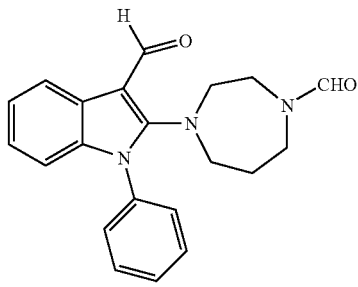

2-Chloro-1-phenyl-1H-indole-3-carboxaldehyde is reacted with [1,4]diazepane-1-carboxaldehyde as described in Example 1 to afford 2-(4-formyl-[1,4]diazepan-1-yl)-1- phenyl-1H-indole-3-carboxaldehyde (97% yield) as a yellow solid. LC/MS: MS 348 (M+H); RT 2.77 min; (CDCl₃): 10.26 (1H, d), 8.22 (1H, d), 8.00 (0.5H, s), 7.86 (0.5H, s), 7.47-7.69 (3H, m), 7.23-7.38 (3H, m), 7.17(1H, t), 6.97 (1H, d), 3.25-3.70 (8H, m), 1.50-1.73(2H, m).

Example 24

2-[4-(2-Hydroxyethyl)diazepan-1-yl]-1-phenyl-1H-indole-3-carboxaldehyde

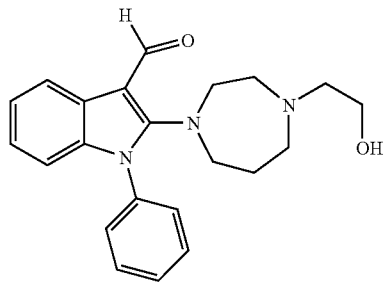

A solution of 2-chloro-1-phenyl-1H-indole-3-carboxaldehyde is reacted with 2-[1,4]diazepam-1-yl-ethanol as described in Example 1 to afford 2-[4-(2-hydroxyethyl)diazepan-1-yl]-1-phenyl-1H-indole-3-carboxaldehyde (20% yield) as a white solid. LC/MS: 346 (M+H); RT 2.77 min; NMR (CDCl₃): 7.66 (1H, d), 7.38-7.60 (5H, m), 7.00-7.18 (3H, m), 6.36 (1H, s), 3.96 (2H, s), 3.84 (2H, m), 3.61 (2H, m), 3.10 (2H, m), 2.60 (2H, m), 1.56-2.20 (4H, m).

Example 25

2-(4-Oxiranylmethyl-[1,4]diazepan-1-yl)-1-phenyl-1H-indole-3-carboxaldehyde

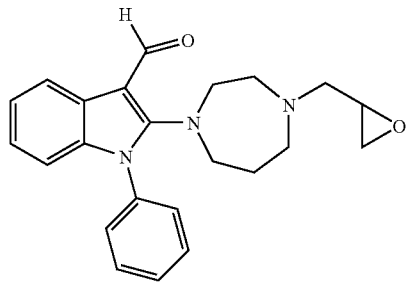

A solution of 2-[1,4]diazepan-1-yl-1-phenyl-1H-indole-3-carboxaldehyde (438 mg, 1.37 mmol), epibromohydrin (188 mg, 1.37 mmol) and potassium carbonate (758 mg, 5.49 mmol) in acetonitrile (20 mL) is refluxed for 2.5 hr. The reaction mixture is cooled, the solvent is removed and the residue is purified by chromatography eluting with dichloromethane-1 to 5% methanol. Fractions containing product are combined and concentrated to afford 2-(4-oxiranylmethyl-[1,4]diazepan-1-yl)-1-phenyl-1H-indole-3-carboxaldehyde (41% yield) as a yellow solid. LC/MS: 376 (M+H), RT 2.65 min; NMR (CDCl₃): 10.28 (1H, s), 8.26 (1H, d), 7.43-7.65 (3H, m), 7.17-7.42 (3H, m), 7.13(1H, t), 6.96 (1H, d), 3.49 (4H, m), 3.03 (1H, m), 2.56-2.86 (4H, m), 2.30-2.50 (2H, m), 1.74(2H, m), 1.56 (2H, s).

Example 26

2-(5-Oxo-[1,4]diazepan-1-yl)-1-phenyl-1H-indole-3-carboxaldehyde

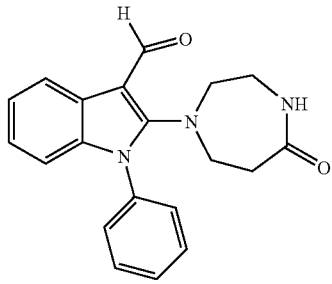

2-Chloro-1-phenyl-1H-indole-3-carboxaldehyde is reacted with [1,4]diazepan-5-one as described in Example 1 to afford 2-(5-oxo-[1,4]diazepam-1-yl)-1-phenyl-1H-indole-3-carboxaldehyde (35% yield) as a yellow solid. LC/MS: MS 334 (M+H); RT 2.64 min; NMR (CDCl₃): 10.26 (1H, d), 8.21(1H, d), 7.52-7.69(3H, m), 7.37 (2H, m), 7.28(1H, t), 7.17(1H, t), 6.98 (1H, d), 3.41 (4H, m), 3.20(2H, m), 2.45(2H, m).

Example 27

2-Imidazol-1-yl-1-phenyl-1H-indole-3-carboxaldehyde

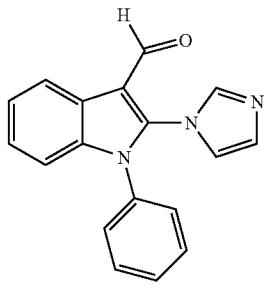

2-Chloro-1-phenyl-1H-indole-3-carboxaldehyde is reacted with imidazole as described in Example 1 to afford 2-imidazol-1-yl-1-phenyl-1H-indole-3-carboxaldehyde (12% yield) as a white solid. LC/MS: 288 (M+H); RT 2.55 min; NMR (CDCl₃): 9.94 (1H, s), 8.45 (1H, d), 7.63 (1H, s), 7.35-7.54 (6H, m), 7.17-7.29 (2H, m), 7.12 (1H, s), 7.03 (1H, s).

Example 28

1-Phenyl-2-[1,4,7]triazocan-1-yl-1H-indole-3-carboxaldehyde

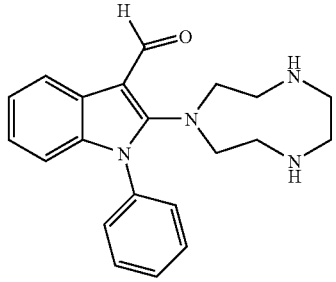

2-Chloro-1-phenyl-1H-indole-3-carboxaldehyde is reacted with [1,4,7]triazocane as described in Example 1 to afford 1-phenyl-2-[1,4,7]triazocan-1-yl-1H-indole-3-carboxaldehyde (37% yield) as a yellow solid. LC/MS: 321 (M+H—H$_2$O); RT 2.96 min; NMR (CDCl$_3$): 7.37 (1H, d), 7.18-7.30 (3H, m), 7.13 (1H, t), 6.97 (2H, d), 6.90 (1H, t), 6.79 (1H, t), 2.76-3.10 (12H, m).

Example 29

1-(4-tert-Butylphenyl)-2-piperazin-1-yl-1H-indole-3-carboxaldehyde

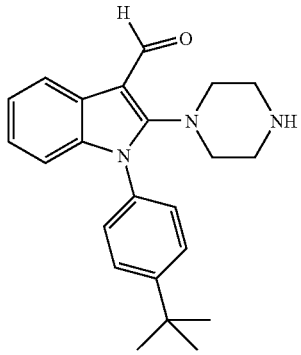

Step 1: 1-(4-tert-Butyl-phenyl)-2-chloro-1H-indole-3-carboxaldehyde:

A mixture of 2-chloro-1H-indole-3-carboxaldehyde (2.2 g, 12.25 mmol), 4-t-butylphenylboronic acid (4.36 g, 24.49 mmol), copper acetate (4.45 g, 24.50 mmol), 4A molecular sieve (2.5 g), pyridine (3.0 mL) and dichloromethane (40 mL) is stirred overnight at room temperature. The reaction mixture is diluted with dichloromethane (100 mL), washed with water (50 mL), with 3N aqueous hydrochloric acid (10 mL), the precipitate removed by filtration and the dichloromethane layer is washed again with water (50 mL), aq sodium bicarbonate, with brine, dried and filtered. The filtrate is concentrated to give a solid. The crude is crystallized from dichloromethane-methanol to afford 1-(4-tert-butylphenyl)-2-chloro-1H-indole-3-carboxaldehyde (3.09 g, 81% yield) as a yellow solid. TLC (silica gel, 20% ethyl acetate/heptane) R$_f$ 0.50; ESI/MS 312 (M+H), RT 4.32 min; NMR: 10.12 (1H, s); 8.20 (1H, d, J=6 Hz); 7.71 (2H, d); 7.53 (2H, d); 7.38 (2H, m); 7.11 (1H, d); 1.38 (9H, s).

Step 2: 1-(4-tert-Butylphenyl)-2-piperazin-1-yl-1H-indole-3-carboxaldehyde:

A mixture of 1-(4-tert-butylphenyl)-2-chloro-1H-indole-3-carboxaldehyde (2.95 g, 9.46 mmol), piperazine (10.60 g, 123 mmol) in dioxane (50 mL) is heated overnight at 110° C. Water is added and the reaction mixture is extracted with ethyl acetate. The combined ethyl acetate layers are washed with brine, dried and concentrated. The crude material is purified by chromatography eluting with dichloromethane-5% methanol. Fractions containing product are combined and concentrated to afford 1-(4-tert-butylphenyl)-2-piperazin-1-yl-1H-indole-3-carboxaldehyde (2.4 g, 70% yield) as a light cream solid. TLC (silica gel, dichloromethane-10% methanol) R$_f$ 0.27; ESI/MS 362 (M+H), RT 3.27 min; NMR 10.14 (1H, s); 8.12 (1H, d, J=3 Hz); 8.09 (2H, d); 7.68 (2H, d); 7.47 (2H, m); 6.91 (1H, d, J=6 Hz); 3.20 (4H, m); 2.53 (4H, m); 2.25 (1H, br s); 1.36 (9H, s).

Example 30

1-(4-tert-Butylphenyl)-2-[4-(2-hydroxyethyl)piperazin-1-yl]-1H-indole-3-carboxaldehyde

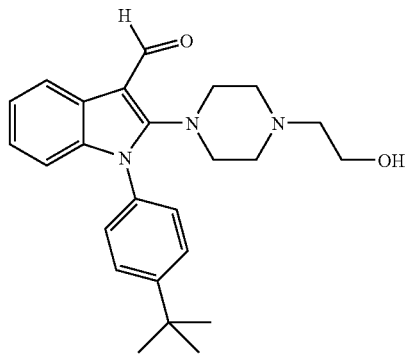

A mixture of 1-[(4-tert-butylphenyl)-2-piperazin-1-yl]-1H-indole-3-carboxaldehyde (1.3 g, 3.60 mmol), 2-bromoethanol (600 mg, 4.80 mmol), potassium carbonate (2.0 g, 14.50 mmol) and acetonitrile (30 mL) is refluxed for 60 hr. More 2-bromoethanol (0.5 mL) is added and refluxing is continued for 25 hr. The cooled reaction mixture is dissolved in water and extracted with ethyl acetate (3×). The combined ethyl acetate layers are washed with brine, dried and concentrated. The residue is purified by chromatography eluting with ethyl acetate-5% to 10% methanol. Product containing fractions are combined and concentrated to afford 1-(4-tert-butylphenyl)-2-[4-(2-hydroxyethyl)piperazin-1-yl]-1H-indole-3-carboxaldehyde (1.2 g, 82% yield) as a pale-yellow solid. TLC (silica gel, dichloromethane-10% methanol) R$_f$ 0.23; ESI/MS 406 (M+H), RT 3.22 min; $^1$H NMR 10.13 (1H, s); 8.11 (1H, d, J=6 Hz); 7.66 (2H, d, J=9 Hz); 7.44 (2H, d, J=6 Hz); 7.19 (2H, m); 6.91 (1H, d, 6 Hz); 4.39 (1H, t); 3.47 (2H, q); 3.26 (4H, br t); 2.34 (6H, br m); 1.36 (9H, s). $^{13}$C NMR 183.17; 156.49; 151.24; 135.68; 134.03; 127.34; 126.58; 125.16; 122.56; 119.97; 109.63; 105.70; 60.18; 58.35; 52.75; 51.50; 34.56; 31.08.

Example 31

Phosphoric Acid 2-{4-[1-(4-tert-butylphenyl)-3-formyl-1H-indol-2-yl]-piperazin-1-yl}-ethyl Ester Diethyl Ester Hydrochloride

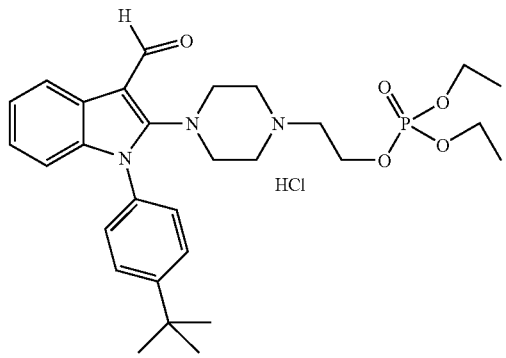

Step 1: Phosphoric acid 2-{4-[1-(4-tert-butylphenyl)-3-formyl-1H-indol-2-yl]-piperazin-1-yl}-ethyl ester diethyl ester:

Diethyl chlorophosphate (0.22 mL, 1.52 mmol) is added to a solution of 1-(4-tert-butylphenyl)-2-[4-(2-hydroxyethyl) piperazin-1-yl]-1H-indole-3-carboxaldehyde (510 mg, 1.26 mmol) and triethylamine (0.35 mL, 2.49 mmol) in tetrahydrofuran (5 mL). The resulting orange solution is stirred overnight at room temperature. Water is added and the mixture is extracted with ethyl acetate. The combined ethyl acetate layers are washed with water, with brine, dried and concentrated to give an oil that is purified by chromatography eluting with ethyl acetate and ethyl acetate-5% methanol to afford the phosphoric acid 2-{4-[1-(4-tert-butylphenyl)-3-formyl-1H-indol-2-yl]-piperazin-1-yl}-ethyl ester diethyl ester (280 mg, 68% yield) as a white powder. ESI/MS 542 (M+H)$R_f$ 3.52 min; $^1$H NMR 10.13 (1H, s); 8.11 (1H, d, J=6 Hz); 7.66 (2H, d, J=6 Hz); 7.46 (2H, d, J=9 Hz); 7.19 (2H, m); 6.92 (1H, d, 9 Hz); 4.04 (6H, m); 3.33 (2H, br s); 3.26 (4H, br s); 2.49 (4H, br s); 1.36 (9H, s); 1.30 (6H, t).

Step 2: Phosphoric Acid 2-{4-[1-(4-tert-butylphenyl)-3-formyl-1H-indol-2-yl]-piperazin-1-yl}-ethyl Ester Diethyl Ester Hydrochloride:

Phosphoric acid 2-{4-[1-(4-tert-butylphenyl)-3-formyl-1H-indol-2-yl]-piperazin-1-yl}-ethyl ester diethyl ester (90 mg, 0.166 mmol) is dissolved in methanol and treated with 1M ethereal hydrochloric acid. The solvents are reduced to half and triturated with ether to obtain phosphoric acid 2-{4-[1-(4-tert-butylphenyl)-3-formyl-1H-indol-2-yl]-piperazin-1-yl}-ethyl ester diethyl ester hydrochloride (85 mg, 89% yield) as a solid. ESI/MS 542 (M+H), RT 3.52 min; $^1$H NMR 10.06 (1H, s); 8.11 (1H, d, J=6 Hz); 7.69 (2H, d, J=9 Hz); 7.51 (2H, d, J=6 Hz); 7.24 (2H, m); 6.96 (1H, d, J=6 Hz); 4.33 (2H, br s); 4.10 (4H, q); 3.68 (2H, br s); 3.39 (6H, br s); 3.03 (2H, br s); 1.37 (9H, s); 1.27 (6H, t); $^{13}$C NMR 229.09; 209.60; 197.36; 184.62; 183.17; 154.06; 151.49; 135.32; 133.45; 127.20; 126.81; 124.98; 122.94; 119.71; 113.77; 109.99; 109.53; 106.00; 63.72; 63.65; 51.36; 48.00; 34.59; 31.06; 15.97; 15.88.

Example 32

1-(4-tert-Butylphenyl)-2-(4-methyl-piperazin-1-yl)-1H-indole-3-carboxaldehyde

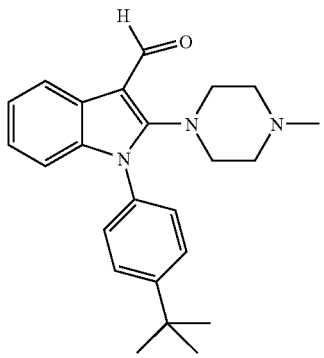

1-(4-tert-Butylphenyl)-2-chloro-1H-indole-3-carboxaldehyde is reacted with 1-methyl piperazine as described in Step 2 of Example 29 to afford 1-(4-tert-butylphenyl)-2-(4-methyl-piperazin-1-yl)-1H-indole-3-carboxaldehyde as a light brown solid. TLC (silica gel, ethyl acetate-16.5% methanol-0.8% 7N methanolic ammonia); $R_f$ 0.23; ESI/MS 376 (M+H), RT 3.4 min; NMR 10.14 (1H, s); 8.12 (1H, d, J=9 Hz); 7.67 (2H, d); 7.45 (2H, d); 7.19 (2H, m); 6.92 (1H, d, J=6 Hz); 3.26 (4H, m); 2.18 (7H, m); 1.37 (9H, s).

Example 33

1-(4-tert-Butylphenyl)-2-piperidin-1-yl-1H-indole-3-carboxaldehyde

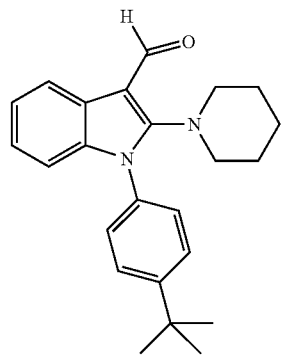

1-(4-tert-Butylphenyl)-2-chloro-1H-indole-3-carboxaldehyde is reacted with piperidine as described in Step 2 of Example 29 to afford 1-(4-tert-butylphenyl)-2-piperidin-1-yl-1H-indole-3-carboxaldehyde (87% yield) as an off-white solid. TLC (silica gel, heptane-30% ethyl acetate); $R_f$ 0.23; ESI/MS 361 (M+H); RT 4.48 min; NMR 10.14 (1H, s); 8.11 (1H, d, J=6 Hz); 7.66 (2H, d); 7.46 (2H, d); 7.16 (2H, m); 6.91 (1H, d, J=9 Hz); 3.27 (4H, m); 1.46 (6H, m); 1.36 (9H, s).

Example 34

1-(4-tert-Butylphenyl)-2-[(2-dimethylaminoethyl)-methylamino]-1H-indole-3-carboxaldehyde

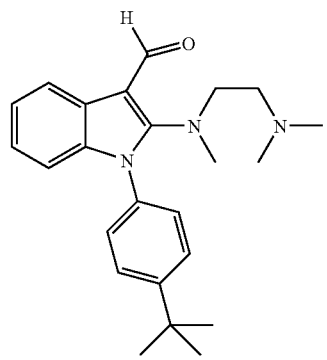

1-(4-tert-Butylphenyl)-2-chloro-1H-indole-3-carboxaldehyde is reacted with N,N,N'-trimethylethylenediamine as described in Step 2 of Example 29 to afford 1-(4-tert-butylphenyl)-2-[(2-dimethylaminoethyl)-methylamino]-1H-indole-3-carboxaldehyde (42% yield) as a light tan solid. TLC (silica gel, 7N NH3 in methanol/MeOH/Ethyl acetate (0.1:2:10 mL)) $R_f$ 0.29. ESI/MS 378 (M+H); RT 3.43 min. NMR 10.18 (1H, s); 8.10 (1H, d, J=9 Hz); 7.66 (2H, d); 7.48 (2H, d); 7.17 (1H, t); 7.08 (1H, t); 6.88 (1H, d, J=9 Hz); 3.21 (2H, t); 3.02 (3H, s); 2.18 (2H, t); 2.00 (6H, t); 1.36 (9H, s).

Example 35

1-(4-tert-Butylphenyl)-2-(2-dimethylaminoethylamino)-1H-indole-3-carboxaldehyde

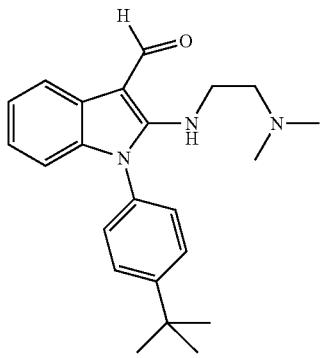

1-(4-tert-Butylphenyl)-2-chloro-1H-indole-3-carboxaldehyde is reacted with N,N-dimethylethylenediamine as described in Step 2 of Example 29 to afford 1-(4-tert-butylphenyl)-2-(2-dimethylaminoethylamino)-1H-indole-3-carboxaldehyde (26% yield) as a light tan solid. ESI/MS 364 (M+H); RT 3.39 min. NMR 9.94 (1H, s); 7.84 (1H, br s); 7.67 (2H, d); 7.48 (2H, d, J=9 Hz); 7.10 (1H, t); 6.98 (1H, t); 6.66 (1H, d, J=9 Hz); 3.05 (2H, br s); 2.30 (2H, BR t); 2.03 (6H, S); 1.36 (9H, s).

Example 36

4-[1-(4-tert-Butylphenyl)-3-formyl-1H-indol-2-yl]piperazine-1-carboxylic acid tert-butyl Ester

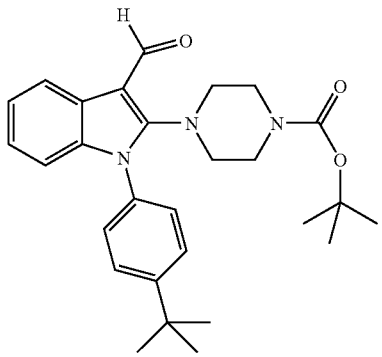

1-(4-tert-Butylphenyl)-2-chloro-1H-indole-3-carboxaldehyde is reacted with 1-Boc-piperazine as described in Step 2 of Example 29 to afford 4-[1-(4-tert-butylphenyl)-3-formyl-1H-indol-2-yl]piperazine-1-carboxylic acid tert-butyl ester (70% yield) as a light yellow solid. TLC (heptane-30% ethyl acetate) $R_f$ 0.19; ESI/MS 462 (M+H); RT=4.42 min.; NMR10.13 (1H, s); 8.13 (1H, d, J=9 Hz); 7.68 (2H, d); 7.49 (2H, d); 7.21 (2H, m); 6.95 (1H, d, J=9 Hz); 3.20 (8H, m); 1.37 (18H, s).

Example 37

5-[1-(4-tert-Butylphenyl)-3-formyl-1H-indol-2-yl]-2,5-diazabicyclo[2.2.1]heptane-2-carboxylic acid tert-butyl ester

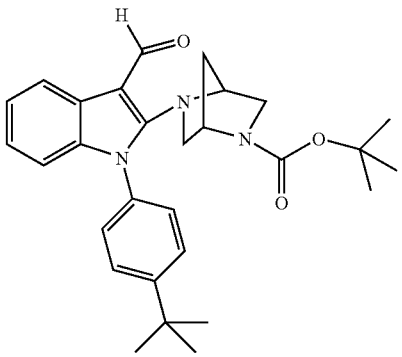

1-(4-tert-Butylphenyl)-2-chloro-1H-indole-3-carboxaldehyde is reacted with (1S, 4S)-2-t-Boc-2,5-diazabicyclo[2.2.1]heptane as described in Step 2 of Example 29 to afford 5-[1-(4-tert-butylphenyl)-3-formyl-1H-indol-2-yl]-2,5-diazabicyclo[2.2.1]heptane-2-carboxylic acid tert-butyl ester (66% yield) as a green solid. TLC (heptane-30% ethyl acetate) $R_f$ 0.07. ESI/MS 418 (M-C(CH$_3$)$_3$), 474 (M+H); RT 4.16 min; NMR 10.02 (1H, s); 8.18 (1H, d, J=6 Hz); 7.63 (4H, br m); 7.13 (2H, m); 6.66 (1H, d, J=9 Hz); 4.75 (1H, br s); 4.30 (1H, br s); 3.28 (2H, br m); 3.08 (2H, br m); 1.99 (2H, br s); 1.35 (18H, 2 peaks overlapping).

Example 38

1-(4-tert-Butyl-phenyl)-2-(2-methyl-aziridin-1-yl)-1H-indole-3-carboxaldehyde

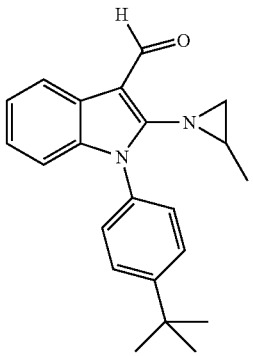

A side-arm tube under a nitrogen atmosphere is charged with 1-(4-tert-butylphenyl)-2-chloro-1H-indole-3-carboxaldehyde (100 mg, 0.321 mmol), Pd$_2$(dba)$_3$ (15 mg, 0.016 mmol), 2,2'-bis(diphenylphosphino)-1,1'-binaphthyl (BINAP) (20 mg, 0.032 mmol) and sodium tert-butylate (46 mg, 0.479 mmol). To this is added toluene (3.0 mL), a solution of 2-methylaziridine (37 mg, 0.678 mmol) in toluene (1.0 mL) and the resulting mixture is stirred overnight at 80° C. The reaction is cooled, water added and the mixture is extracted with ethyl acetate. The combined ethyl acetate layer are washed with water, with brine, dried over sodium sulfate, filtered and the solvent concentrated to give an oil that is purified by chromatography eluting with heptane-5 to 30% ethyl acetate. Product containing fractions are combined and concentrated to afford 1-(4-tert-butyl-phenyl)-2-(2-methyl-aziridin-1-yl)-1H-indole-3-carboxaldehyde (70 mg, 66% yield) as a yellow solid. TLC (heptane-30% ethyl acetate/) R$_f$ 0.20; ESI/MS 333 (M+H); RT 4.15 min; NMR 10.16 (1H, s); 8.08 (1H, d, J=6 Hz); 7.70 (2H, d, J=9 Hz); 7.49 (2H, d, 9 Hz); 7.21 (2H, m); 6.91 (1H, d, J=9 Hz); 2.43 (2H, m); 2.28 (1H, d); 1.38 (9H, s); 0.79 (3H, d, J=6 Hz).

Example 39

1-(4-tert-Butylphenyl)-2-(2-pyrrolidin-1-yl-ethylamino)-1H-indole-3-carboxaldehyde Hydrochloride

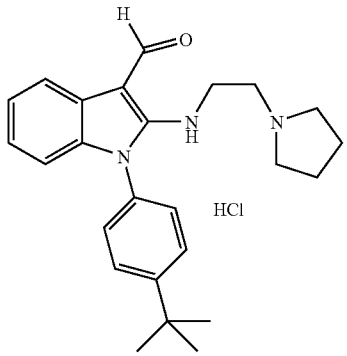

1-(4-tert-Butylphenyl)-2-chloro-1H-indole-3-carboxaldehyde is reacted with 1-(2-aminoethyl)pyrrolidine as described in Step 2 of Example 29 to obtain oil. The oil is dissolved in small amount of methanol and treated with 1M ethereal hydrochloric acid. The solvents are removed and the residue is triturated with ether to yield 1-(4-tert-butylphenyl)-2-(2-pyrrolidin-1-yl-ethylamino)-1H-indole-3-carboxaldehyde hydrochloride (20% yield) as a light beige solid. ESI/MS 390 (M+H); RT 3.42 min. NMR 10.68 (1H, s); 7.95 (1H, d, J=9 Hz); 7.67 (2H, d, J=9 Hz); 7.47 (2H, d, J=9 Hz); 7.10 (2H, m); 6.63 (1H, d, J=9 Hz); 3.54 (2H, m); 3.40 (2H, m); 3.21 (2H, m); 2.83 (2H, m); 1.91 (4H, m); 1.35 (9H, s).

Example 40

4-(3-Formyl-1-phenyl-1H-indol-2-yl)piperazine-1-carboxylic acid tert-butyl ester

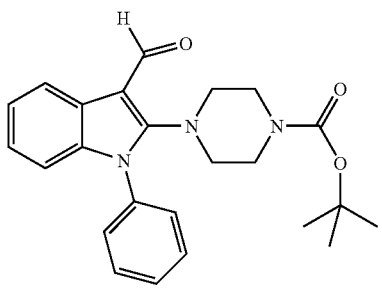

2-Chloro-1H-indole-3-carboxaldehyde is reacted with t-butyl-1-piperazinecarboxylate as described in Step 2 of Example 29 to afford 4-(3-formyl-1-phenyl-1H-indol-2-yl)piperazine-1-carboxylic acid tert-butyl ester (43% yield) as a yellow solid. ESI/MS 300 (M), 306 [M-CO$_2$C(CH$_3$)$_3$], 350 [M-C(CH$_3$)$_3$], 406 (M+H); RT=3.89 min; NMR 10.15 (1H, s); 8.14 (1H, d, J=9 Hz); 7.69 (5H, m); 7.22 (2H, m); 6.94 (1H, d, J=9 Hz); 3.22 (8H, 2 br m); 1.37 (9H, s).

Example 41

2-[4-(2-Hydroxyethyl)piperazin-1-yl]-1-phenyl-1H-indole-3-carboxaldehyde Hydrochloride

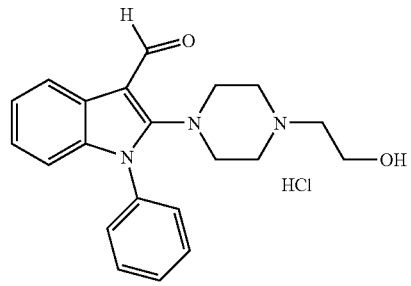

Step 1: 2-[4-(2-Hydroxyethyl)piperazin-1-yl]-1-phenyl-1H-indole-3-carboxaldehyde:
1-Phenyl-2-piperazin-1-yl-1H-indole-3-carboxaldehyde is reacted with bromoethanol as described in Example 30 to afford 2-[4-(2-hydroxyethyl)piperazin-1-yl]-1-phenyl-1H-indole-3-carboxaldehyde (87% yield) as a yellow solid. TLC (ethyl acetate-10% methanol) R$_f$ 0.13; ESI/MS 350 (M+H); RT 2.67 min; NMR 10.16 (1H, s); 8.13 (1H, d, J=6 Hz); 7.68 (5H, m); 7.20 (2H, m); 6.91 (1H, d, J=6 Hz); 4.39 (1H, t); 3.47 (2H, q); 3.2 (4H, m); 2.34 (6H, m).

Step 2: 2-[4-(2-Hydroxyethyl)-piperazin-1-yl]-1-phenyl-1H-indole-3-carboxaldehyde Hydrochloride:
2-[4-(2-Hydroxyethyl)piperazin-1-yl]-1-phenyl-1H-indole-3-carboxaldehyde is dissolved in methanol and treated with 1M ethereal hydrochloric acid. After stirring for 30 min., the solvent is removed and the residue is dissolved in a small amount of methanol and treated with ether to precipitate 2-[4-(2-hydroxyethyl)piperazin-1-yl]-1-phenyl-1H-indole-3-carboxaldehyde hydrochloride (85% yield) as a cream solid. ESI/MS 350 (M+H); RT 2.32 min; NMR 10.15 (1H, s); 8.13 (1H, d, 9 Hz); 7.70 (5H, m); 7.25 (2H, m); 6.96 (1H, d, J=6 Hz); 5.31 (1H, br s); 3.73 (2H, br s); 3.56 (6H, br m); 3.17 (2H, br s); 2.97 (2H, br s).

Example 42

Phosphoric Acid 2-[4-(3-Formyl-1-phenyl-1H-indol-2-yl)piperazin-1-yl]ethyl Ester Diethyl Ester Hydrochloride

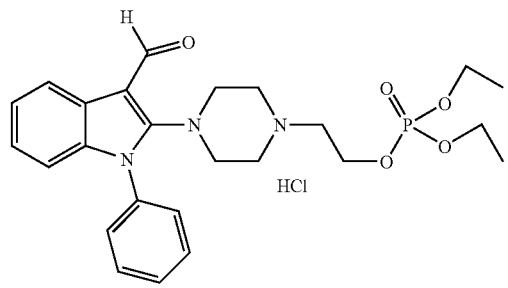

Step 1: Phosphoric Acid Diethyl Ester 2-[4-(3-formyl-1-phenyl-1H-indol-2-yl)-piperazin-1-yl]-ethyl ester:

2-[4-(2-Hydroxyethyl)piperazin-1-yl]-1-phenyl-1H-indole-3-carboxaldehyde is reacted with diethyl chlorophosphate as described in Step 1 of Example 31 to afford phosphoric acid diethyl ester 2-[4-(3-formyl-1-phenyl-1H-indol-2-yl)piperazin-1-yl]ethyl ester (71% yield) as a yellow solid. ESI/MS 486 (M+H); RT 2.94 min; NMR 10.15 (1H, s); 8.13 (1H, d, J=9 Hz); 7.68 (5H, m); 7.20 (2H, m); 6.91 (1H, d, J=6 Hz), 4.04 (6H, m); 3.28 (6H, m); 2.49 (4H, br s); 1.23 (6H, t).

Step 2: Phosphoric acid diethyl ester 2-[4-(3-formyl-1-phenyl-1H-indol-2-yl)-piperazin-1-yl]-ethyl ester Hydrochloride:

Phosphoric acid diethyl ester 2-[4-(3-formyl-1-phenyl-1H-indol-2-yl)piperazin-1-yl]ethyl ester is treated with 1M ethereal hydrochloric acid as described in Step 2 of Example 31 to obtain phosphoric acid diethyl ester 2-[4-(3-formyl-1-phenyl-1H-indol-2-yl)-piperazin-1-yl]-ethyl ester hydrochloride (54% yield) as pink powder. ESI/MS 486 (M+H); RT 2.52 min: NMR 10.15 (1H, s); 8.13 (1H, d, J=6 Hz); 7.70 (5H, m); 7.24 (2H, m); 6.96 (1H, d, J=9 Hz); 4.30 (2H, br s); 4.07 (6H, m); 3.59 (8H, br m); 1.27 (6H, t).

Example 43

2-(Morpholin-4-yl)-1-phenyl-1H-indole-3-carboxaldehyde

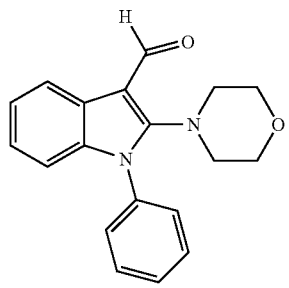

2-Chloro-1-phenyl-1H-indole-3-carboxaldehyde is reacted with morpholine as described in Step 2 of Example 29 to afford 2-(morpholin-4-yl)-1-phenyl-1H-indole-3-carboxaldehyde (885 yield) as a fluffy, creamy solid. ESI/MS 307 (M+H); RT 2.99 min; NMR 10.15 (1H, s); 8.14 (1H, d, J=6 Hz); 7.69 (5H, m); 7.22 (2H, m); 6.94 (1H, d, J=9 Hz); 3.45 (4H, m); 3.28 (4H, m).

Example 44

2-(3,5-Dimethylpiperazin-1-yl)-1-phenyl-1H-indole-3-carboxaldehyde Hydrochloride

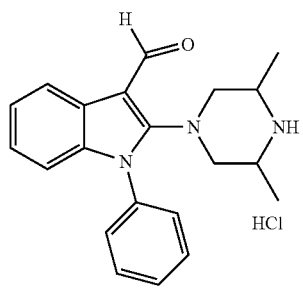

2-Chloro-1-phenyl-1H-indole-3-carboxaldehyde is reacted with 2,6-dimethylpiperazine as described in Step 2 of Example 29 to afford 2-(3,5-dimethylpiperazin-1-yl)-1-phenyl-1H-indole-3-carboxaldehyde as a solid. The solid is dissolved in methanol, treated with 1M ethereal hydrochloric acid and concentrated. The residue triturated with ether to give 2-(3,5-dimethylpiperazin-1-yl)-1-phenyl-1H-indole-3-carboxaldehyde hydrochloride (74% yield) as a purple solid. ESI/MS 334 (M+H); RT=2.52 min.

Example 45

5-(3-Formyl-1-phenyl-1H-indol-2yl)-2,5-diazabicyclo[2.2.1]heptane-2-carboxylic acid tert-butyl ester

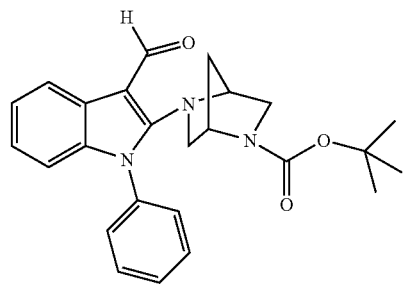

2-Chloro-1-phenyl-1H-indole-3-carboxaldehyde is reacted with (1S, 4S)-2-t-boc-2,5-diazabicyclo[2.2.1]heptane as described in Step 2 of Example 29 to afford 5-(3-formyl-1-phenyl-1H-indol-2yl)-2,5-diazabicyclo[2.2.1]heptane-2-carboxylic acid tert-butyl ester (98% yield) as a purple solid. TLC (heptane-50% ethyl acetate) $R_f$ 0.46; NMR 10.27 (1H, s); 8.26 (1H, d, J=9 Hz); 7.62 (3H, m); 7.41 (2H, d); 7.24 (1H, m); 7.18 (1H, t); 6.99 (1H, d, J=9 Hz); 3.32 (8H, 2 broad s peaks); 1.44 (9H, s).

Example 46

1-(3-Formylphenyl)-2-(piperazin-2-yl)-1H-indole-3-carboxaldehyde

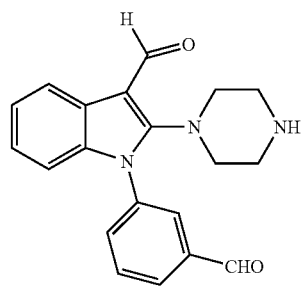

Step 1: 2-Chloro-1-(3-formylphenyl)-1H-indole-3-carboxaldehyde:

2-Chloro-1H-indole-3-carboxaldehyde is reacted with 3-formylphenylboronic acid as described in Step 1 of Example 29 to afford 2-chloro-1-(3-formylphenyl)-1H-indole-3-carboxaldehyde (99% yield) as a white solid. ESI/MS 284 (M+H); RT 3.37 min; NMR 10.15 (1H, s); 10.12 (1H, s); 8.23 (3H, m); 7.98 (2H, m); 7.41 (2H, m); 7.18 (1H, d, J=9 Hz).

Step 2: 1-(3-Formylphenyl)-2-(piperazin-2-yl)-1H-indole-3-carboxaldehyde:

2-Chloro-1-(3-formylphenyl)-1H-indole-3-carboxaldehyde is reacted with piperazine as described in Step 2 of Example 29 to afford 1-(3-formylphenyl)-2-(piperazin-2-yl)-1H-indole-3-carboxaldehyde (59% yield) as a cream solid. ESI/MS 334 (M+H); RT 2.29 min.

Example 47

1-(Biphenyl-4-yl)-2-piperazin-1-yl-1H-indole-3-carboxaldehyde Hydrochloride

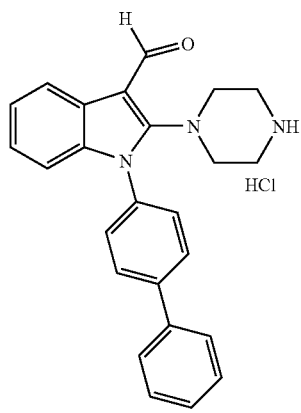

Step 1: 1-Biphenyl-4-yl-2-chloro-1H-indole-3-carboxaldehyde:

2-Chloro-1H-indole-3-carboxaldehyde is reacted with 4-biphenylboronic acid as described in Step 1 of Example 29 to afford 1-biphenyl-4-yl-2-chloro-1H-indole-3-carboxaldehyde (52% yield) as a yellow solid. ESI/MS 332 (M+H), RT 4.14 min; NMR 10.15 (1H, s); 8.23 (1H, d, J=9 Hz); 7.99 (2H, d, J=9 Hz); 7.82 (2H, d, J=9 Hz); 7.69 (7H, m); 7.54 (1H, m).

Step 2: 1-(Biphenyl-4-yl)-2-piperazin-1-yl-1H-indole-3-carboxaldehyde Hydrochloride:

1-(Biphenyl-4-yl)-2-chloro-1H-indole-3-carboxaldehyde is reacted with piperazine as described in Step 2 of Example 29 and subsequently treated with hydrochloric acid as described in Example 44 to afford 1-(biphenyl-4-yl)-2-(piperazin-1-yl)-1H-indole-3-carboxaldehyde hydrochloride (44% yield) as a cream solid. ESI/MS 382 (M+H), RT=2.87 min.

Example 48

1-(4-Ethylphenyl)-2-(piperazin-1-yl)-1H-indole-3-carboxaldehyde Hydrochloride

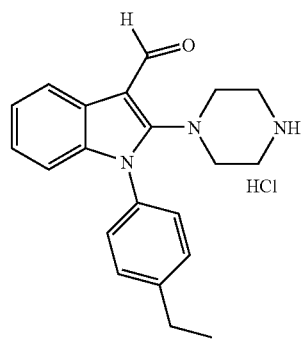

Step 1: 2-Chloro-1-(4-ethylphenyl)-1H-indole-3-carboxaldehyde:

2-Chloro-1H-indole-3-carboxaldehyde is reacted with 4-ethylphenylboronic acid as described in Step 1 of Example 29 to afford 2-chloro-1-(4-ethyl-phenyl)-1H-indole-3-carboxaldehyde (73% yield) as a light yellow solid. ESI/MS 284 (M+H); RT 4.04 min; NMR 10.12 (1H, s); 8.20 (1H, d, J=9 Hz); 7.54 (4H, m); 7.38 (2H, m); 7.28 (1H, d); 2.77 (2H, q); 1.28 (3H, t).

Step 2: 1-(4-Ethylphenyl)-2-(piperazin-1-yl)-1H-indole-3-carboxaldehyde Hydrochloride:

2-Chloro-1-(4-ethylphenyl)-1H-indole-3-carboxaldehyde is reacted with piperazine as described in Step 2 of Example 29 and subsequently treated with hydrochloric acid as described in Example 44 to afford 1-(4-ethylphenyl)-2-(piperazin-1-y)-1H-indole-3-carboxaldehyde hydrochloride (39% yield) as a cream solid. ESI/MS 334 (M+H); RT=2.67 min; NMR 10.13 (1H, s); 8.11 (1H, d, J=6 Hz); 7.50 (4H, s); 7.24 (2H, m); 6.94 (1H, d, J=6 Hz); 3.42 (4H, m); 2.95 (4H, m); 2.76 (2H, q); 1.30 (3H, t).

Example 49

1-(3-Bromophenyl)-2-piperazin-1-yl-1H-indole-3-carboxaldehyde

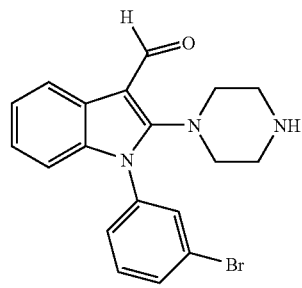

Step 1: 1-(3-Bromophenyl)-2-chloro-1H-indole-3-carboxaldehyde:

2-Chloro-1H-indole-3-carboxaldehyde is reacted with 3-bromophenylboronic acid as described in Step 1 of Example 29 to afford 1-(3-bromophenyl)-2-chloro-1H-indole-3-carboxaldehyde (87% yield) as a cream solid. ESI/MS 334 (M), 375 [(M+2+CH$_3$CN) adduct]; RT 3.59 min.

Step 2: 1-(3-Bromophenyl)-2-piperazin-1-yl-1H-indole-3-carboxaldehyde:

1-(3-bromo-phenyl)-2-chloro-1H-indole-3-carboxaldehyde is reacted with piperazine as described in Step 2 of Example 29 to afford 1-(3-bromophenyl)-2-piperazin-1-yl-1H-indole-3-carboxaldehyde (31% yield). ESI/MS 384 (M), 386 (M+2); RT 2.70 min; NMR (CDCl$_3$) 10.31 (1H, s); 8.28 (1H, d, J=9 Hz); 7.67 (2H, m); 7.63-7.16 (5H, m); 7.01 (1H, d, J=9 Hz); 3.31 (4H, m); 2.82 (4H, m).

Example 50

1-(4-Methyl-3-nitrophenyl)-2-(piperazin-1-yl)-1H-indole-3-carboxaldehyde

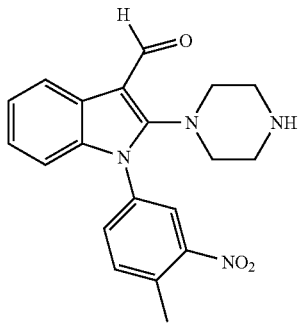

Step 1: 2-Chloro-1-(4-methyl-3-nitrophenyl)-1H-indole-3-carboxaldehyde:

2-Chloro-1H-indole-3-carboxaldehyde is reacted with 4-methyl-3-nitrophenylboronic acid as described in Step 1 of Example 29 to afford 2-chloro-1-(4-methyl-3-nitrophenyl)-1H-indole-3-carboxaldehyde (35% yield) as a light cream solid. ESI/MS 315 (M+H); 356 [(M+1+CH$_3$CN) adduct]; RT 3.35 min.

Step 2: 1-(4-Methyl-3-nitrophenyl)-2-(piperazin-1-yl)-1H-indole-3-carboxaldehyde:

2-chloro-1-(4-methyl-3-nitrophenyl)-1H-indole-3-carboxaldehyde is reacted with piperazine as described in Step 2 of Example 29 to afford 1-(4-methyl-3-nitrophenyl)-2-(piperazin-1-yl)-1H-indole-3-carboxaldehyde (68% yield). ESI/MS 365 (M+H); RT=2.65 min; NMR (CDCl$_3$) 10.35 (1H, s); 8.31 (1H, d, J=9 Hz); 8.11 (1H, s); 7.61 (2H); 7.31 (2H); 7.01 (1H, d, J=9 Hz); 3.31 (4H, m); 2.88 (4H, m); 2.74 (3H, s).

Example 51

1-(4-Dimethylaminophenyl)-2-piperazin-1-yl-1H-indole-3-carboxaldehyde

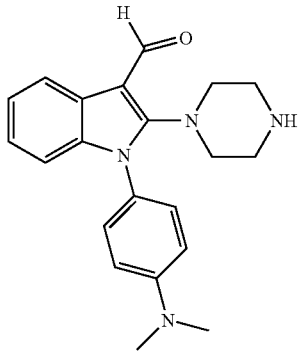

Step 1: 2-Chloro-1-(4-dimethylamino-phenyl)-1H-indole-3-carboxaldehyde:

2-Chloro-1H-indole-3-carboxaldehyde is reacted with (4-dimethylamino)-phenylboronic acid as described in Step 1 of Example 29 to afford 2-chloro-1-(4-dimethylamino-phenyl)-1H-indole-3-carboxaldehyde (80% yield) as a light beige solid. ESI/MS 299 (M+H); RT 3.37 min.

Step 2: 1-(4-Dimethylaminophenyl)-2-piperazin-1-yl-1H-indole-3-carboxaldehyde:

2-chloro-1-(4-dimethylaminophenyl)-1H-indole-3-carboxaldehyde is reacted with piperazine as described in Step 2 of Example 29 to afford 1-(4-dimethylaminophenyl)-2-piperazin-1-yl-1H-indole-3-carboxaldehyde (51% yield). ESI/MS 349 (M+H); RT 2.44 min; NMR (CDCl$_3$) 10.24 (1H, s); 8.25 (1H, d, J=9 Hz); 7.20 (3H, m); 7.10 (1H, m); 6.97 (1H, d, J=9 Hz); 6.83 (2H, d); 3.29 (4H, m); 3.05 (6H, s); 2.82 (4H, m).

Example 52

1-(4-Phenoxyphenyl)-2-(piperazin-1-y)l-1H-indole-3-carboxaldehyde

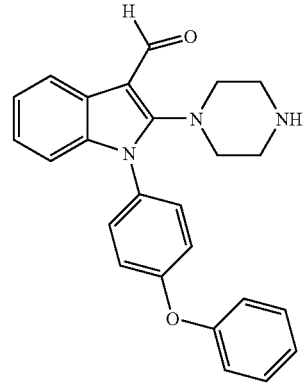

Step 1: 2-Chloro-1-(4-phenoxy-phenyl)-1H-indole-3-carboxaldehyde:

2-Chloro-1H-indole-3-carboxaldehyde is reacted with 4-phenoxyphenylboronic acid as described in Step 1 of Example 29 to afford 2-chloro-1-(4-phenoxyphenyl)-1H-indole-3-carboxaldehyde (34% yield) as a cream solid. ESI/MS 348 (M+H), 389 [(M+1+CH$_3$CN) adduct], RT 3.74 min.

Step 2: 1-(4-Phenoxyphenyl)-2-(piperazin-1-y)l-1H-indole-3-carboxaldehyde:

2-chloro-1-(4-phenoxyphenyl)-1H-indole-3-carboxaldehyde is reacted with piperazine as described in Step 2 of Example 29 to afford 1-(4-phenoxyphenyl)-2-piperazin-1-yl-1H-indole-3-carboxaldehyde (40% yield). ESI/MS 398 (M+H); RT=2.95 min; NMR (CDCl$_3$) 10.28 (1H, s); 8.28 (1H, d, J=9 Hz); 7.46-7.10 (1H, m); 7.00 (1H, d, J=9 Hz); 3.31 (4H, m); 2.81 (4H, m).

Example 53

1-(4-Methylphenyl)-2-(piperazin-1-yl)-1H-indole-3-carboxaldehyde

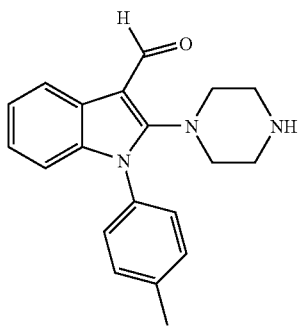

Step 1: 2-Chloro-1-p-tolyl-1H-indole-3-carboxaldehyde:
2-Chloro-1H-indole-3-carboxaldehyde is reacted with 4-tolylboronic acid as described in Step 1 of Example 29 to afford 2-chloro-1-(4-methylphenyl)-1H-indole-3-carboxaldehyde (48% yield) as a cream solid. ESI/MS 270 (M+H), 311 [(M+1+CH$_3$CN) adduct]: RT 3.55 min.

Step 2: 1-(4-Methylphenyl)-2-(piperazin-1-yl)-1H-indole-3-carboxaldehyde:
2-chloro-1-(4-methylphenyl)-1H-indole-3-carboxaldehyde is reacted with piperazine as described in Step 2 of Example 29 to afford 1-(4-methylphenyl)-2-(piperazin-1-yl)-1H-indole-3-carboxaldehyde (29% yield). ESI/MS 320 (M+H); RT=2.64 min; NMR (CDCl$_3$) 10.27 (1H, s); 8.27 (1H, d, J=9 Hz); 7.38-7.15 (6H, m); 6.96 (1H, d, J=6 Hz); 3.26 (4H, m); 2.81 (4H, m); 2.47 (3H, s).

Example 54

1-(4-Fluorophenyl)-2-(piperazin-1-yl)-1H-indole-3-carboxaldehyde Hydrochloride

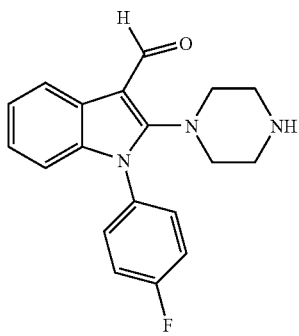

Step 1: 2-Chloro-1-(4-fluorophenyl)-1H-indole-3-carboxaldehyde:
2-Chloro-1H-indole-3-carboxaldehyde is reacted with 4-fluorophenylboronic acid as described in Step 1 of Example 29 to afford 2-chloro-1-(4-fluorophenyl)-1H-indole-3-carboxaldehyde (84% yield) as a cream solid. ESI/MS 274 (M+H); RT 3.64 min; NMR 10.12 (1H, s); 8.20 (1H, d, J=6 Hz); 7.72 (2H, m); 7.58 (2H, m); 7.39 (2H, m); 7.12 (1H, d, J=9 Hz).

Step 2: 1-(4-Fluorophenyl)-2-(piperazin-1-yl)-1H-indole-3-carboxaldehyde Hydrochloride:
2-Chloro-1-(4-fluorophenyl)-1H-indole-3-carboxaldehyde is reacted with piperazine as described in Step 2 of Example 29 and subsequently treated with hydrochloric acid as described in Example 44 to afford 1-(4-fluorophenyl)-2-(piperazin-1-yl)-1H-indole-3-carboxaldehyde hydrochloride (40% yield) as a cream solid. ESI/MS 324 (M+H); RT 2.44 min; NMR 10.15 (1H, s); 8.13 (1H, d, J=9 Hz); 7.71 (2H, m); 7.54 (2H, m); 7.23 (2H, m); 6.95 (1H, d, J=9 Hz); 3.33 (4H, br s); 2.95 (4H, br s).

Example 55

1-(3-Chlorophenyl-2-(piperazin-1-yl)-1H-indole-3-carboxaldehyde

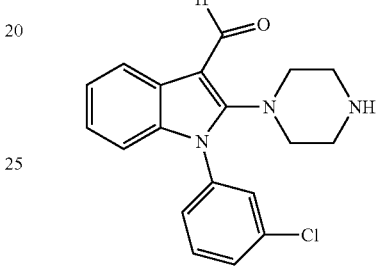

Step 1: 2-Chloro-1-(3-chlorophenyl)-1H-indole-3-carboxaldehyde:
2-Chloro-1H-indole-3-carboxaldehyde is reacted with 3-chlorophenylboronic acid as described in Step 1 of Example 29 to afford 2-chloro-1-(3-chlorophenyl)-1H-indole-3-carboxaldehyde (70% yield) as a cream solid. ESI/MS 290 (M+H); RT 3.55 min; NMR 10.13 (1H, s); 8.21 (1H, d); 7.84 (1H, d); 7.74 (3H, m); 7.38 (2H, m); 7.16 (1H, d, J=9 Hz).

Step 2: 1-(3-Chlorophenyl-2-(piperazin-1-yl)-1H-indole-3-carboxaldehyde:
2-Chloro-1-(3-chlorophenyl)-1H-indole-3-carboxaldehyde is reacted with piperazine as described in Step 2 of Example 29 to afford 1-(3-chlorophenyl)-2-(piperazin-1-yl)-1H-indole-3-carboxaldehyde (64% yield) as a cream solid. ESI/MS 340 (M+H); RT 2.66 min.

Example 56

2-(piperazin-1-yl)-1-(4-vinylphenyl)-1H-indole-3-carboxaldehyde

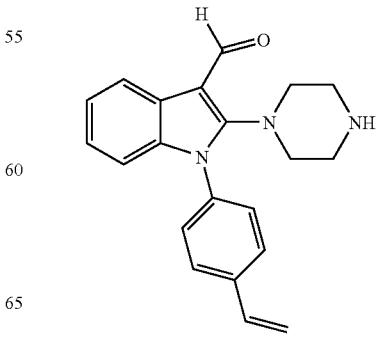

Step 1: 2-Chloro-1-(4-vinylphenyl)-1H-indole-3-carboxaldehyde:

2-Chloro-1H-indole-3-carboxaldehyde is reacted with 4-vinylphenylboronic acid as described in step-1 of Example 29 to afford 2-chloro-1-(4-vinylphenyl)-1H-indole-3-carboxaldehyde (28% yield) as a off white solid. ESI/MS 282 (M+H); RT 3.59 min; NMR 10.22 (1H, s); 8.36 (1H, d, J=6 Hz); 7.65 (2H, d); 7.37 (5H, m); 6.87 (1H, dd); 5.92 (1H, d, J=18 Hz); 5.45 (1H, d, J=12 Hz).

Step 2: 2-(piperazin-1-yl)-1-(4-vinylphenyl)-1H-indole-3-carboxaldehyde:

2-Chloro-1-(4-vinylphenyl)-1H-indole-3-carboxaldehyde is reacted with piperazine as described in Step 2 of Example 29 to afford 2-(piperazin-1-yl)-1-(4-vinylphenyl)-1H-indole-3-carboxaldehyde (44% yield) as a yellow solid. ESI/MS 332 (M+H), RT 2.57 min; NMR (CDCl₃) 10.29 (1H, s); 8.28 (1H, d, J=6 Hz); 7.62 (2H, d, J=6 Hz); 7.38 (4H, m); 7.00 (1H, d, J=9 Hz); 6.85 (1H, dd); 5.89 (1H, d, J=15 Hz); 5.42 (1H, d, J=18 Hz); 3.38 (4H, m); 2.77 (4H, m).

Example 57

1-(3-Hydroxymethylphenyl)-2-(piperazin-1-yl)-1H-indole-3-carboxaldehyde

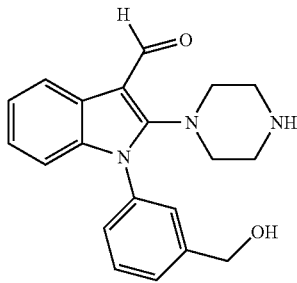

Step 1: 2-Chloro-1-(3-hydroxymethylphenyl)-1H-indole-3-carboxaldehyde:

2-Chloro-1H-indole-3-carboxaldehyde is reacted with 3-(hydroxymethyl)-phenylboronic acid as described in Step 1 of Example 29 to afford 2-chloro-1-(3-hydroxymethylphenyl)-1H-indole-3-carboxaldehyde (17% yield) as a pink solid. ESI/MS 286 (M+H); RT 2.85 min.

Step 2: 1-(3-Hydroxymethylphenyl)-2-(piperazin-1-yl)-1H-indole-3-carboxaldehyde:

2-Chloro-1-(3-hydroxymethylphenyl)-1H-indole-3-carboxaldehyde is reacted with piperazine as described in Step 2 of Example 29 to afford 1-(3-hydroxymethylphenyl)-2-(piperazin-1-yl)-1H-indole-3-carboxaldehyde (32% yield) as a red solid. ESI/MS 336 (M+H); RT 2.37 min.

Example 58

1-(3-Ethoxyphenyl)-2-(piperazin-1-yl)-1H-indole-3-carboxaldehyde

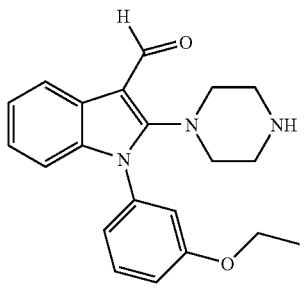

2-Chloro-1H-indole-3-carboxaldehyde is reacted with 4-ethoxyphenylboronic acid as described in Step 1 of Example 29 to afford 2-chloro-1-(4-ethoxyphenyl)-1H-indole-3-carboxaldehyde (37% yield) as a off white solid. ESI/MS 300 (M+H); RT 3.56 min.

Step 2: 1-(3-Ethoxyphenyl)-2-(piperazin-1-yl)-1H-indole-3-carboxaldehyde:

2-Chloro-1-(3-ethoxyphenyl)-1H-indole-3-carboxaldehyde is reacted with piperazine as described in Step 2 of Example 29 to afford 1-(3-ethoxyphenyl)-2-(piperazin-1-yl)-1H-indole-3-carboxaldehyde (37% yield) as a light yellow solid. ESI/MS 350 (M+H); RT 2.69 min; NMR (CDCl₃) 10.26 (1H, s); 8.26 (1H, d, J=6 Hz); 7.28 (3H, m); 7.21 (3H, m); 6.95 (1H, d, J=9 Hz); 4.15 (2H, q); 3.29 (4H, m); 2.79 (4H, m); 1.49 (3H, t).

Example 59

1-Benzenesulfonyl-2-(piperazin-1-yl)-1H-indole-3-carboxaldehyde

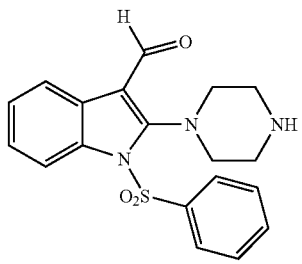

Step 1: 1-Benzenesulfonyl-2-chloro-1H-indole-3-carboxaldehyde:

The title compound is prepared in accordance with the procedure of O. Olton et al., *Tetrahedron*, 54 (1998), 13915-13928 as follows. Sodium hydroxide is added to a stirred solution of 2-chloro-1H-indole-3-carboxaldehyde (239 mg, 1.33 mmol) in ethanol (10 mL). After 2 hr, the solvent is removed and the solid residue is dissolved in acetone and treated with benzenesulfonyl chloride (0.25 mL, 1.96 mmol). Soon a solid precipitated. After stirring for 1.5 hr at room temperature, the reaction mixture is heated to reflux for 1.5 hr. After cooling, water is added and the reaction is extracted with dichloromethane. The combined dichloromethane layer is washed with brine, dried over sodium sulfate and concentrated to an oil that is purified by chromatography eluting with heptane-0 to 10% ethyl acetate. Product containing fractions are combined and concentrated to afford 1-benzenesulfonyl-2-chloro-1H-indole-3-carboxaldehyde (70 mg, 17% yield) as a yellow solid. MS 320 (M+H); NMR 10.09 (1H, s); 8.26 (1H, d, J=9 Hz); 8.15 (3H, m); 7.85 (3H, m); 7.56 (2H, m).

Step 2: 1-Benzenesulfonyl-2-(piperazin-1-yl)-1H-indole-3-carboxaldehyde:

1-Benzenesulfonyl-2-chloro-1H-indole-3-carboxaldehyde is reacted with piperazine as described in Step 2 of Example 29 to afford 1-benzenesulfonyl-2-(piperazin-1-yl)-1H-indole-3-carboxaldehyde (45% yield). ESI/MS 370 (M+H); RT 2.59 min.

Example 60

2-(piperazin-1-yl)-1-(pyridin-2-yl)-1H-indole-3-carboxaldehyde

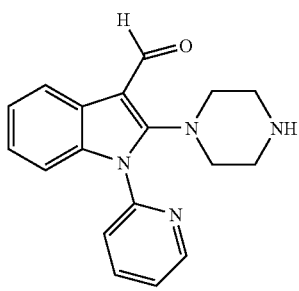

Step 1: 2-Chloro-1-pyridin-2-yl-1H-indole-3-carboxaldehyde:

The title compound is prepared following the procedure of Andreani, A. et al., *J. Med. Chem.* 20, (1977) 1344-1346 as follows. To a mixture of dimethylformamide (0.50 mL) and dichloromethane (0.50 mL) is added phosphorus oxychloride (0.50 mL) at 0° C. After stirring for 15 min, a solution of 1-(pyridin-2-yl)-1,3-dihydroindol-2-one (Le Baunt, G. et al., EP 0 580 502) (250 mg, 1.2 mmol) in dichloromethane (2.0 mL) and pyridine (0.25 mL) is added and the resulting dark-red solution is stirred for 36 hr. The reaction mixture is poured onto ice water and extracted with dichloromethane. The combined organic layer is washed with water, with saturated sodium bicarbonate, with brine, dried over sodium sulfate, filtered and concentrated. The dark residue is purified by chromatography eluting with dichloromethane-0 to 3% methanol. Product containing fractions are combined and concentrated to afford 2-chloro-1-(pyridin-2-yl)-1H-indole-3-carboxaldehyde (70 mg, 23% yield) as a beige solid. TLC (dichloromethane) $R_f$ 0.18; ESI/MS 257 (M+H); RT 2.99 min; NMR 10.16 (1H, s); 8.79 (1H, d); 8.25 (2H, m); 7.84 (1H, d, J=9 Hz); 7.73 (1H, m); 7.40 (3H, m).

Step 2: 2-(piperazin-1-yl)-1-(pyridin-2-yl)-1H-indole-3-carboxaldehyde:

2-Chloro-1-(pyridin-2-yl)-1H-indole-3-carboxaldehyde is reacted with piperazine as described in Step 2 of Example 29 to afford 2-(piperazin-1-yl)-1-(pyridin-2-yl)-1H-indole-3-carboxaldehyde (72% yield) as an orange solid. ESI/MS 307 (M+H); RT 2.23 min; NMR 10.30 (1H, s); 8.75 (1H, m); 8.26 (1H, d, J=9 Hz); 7.98 (1H, m); 7.46 (5H, m); 3.30 (4H, m); 2.81 (4H, m).

Example 61

1-(4-Butylphenyl)-2-(piperazin-1-yl)-1H-indole-3-carboxaldehyde Hydrochloride

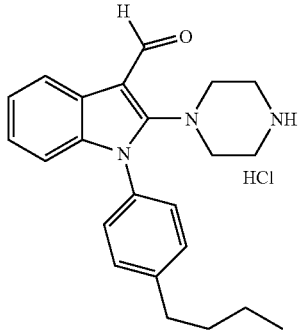

1-(4-Butylphenyl)-2-chloro-1H-indole-3-carboxaldehyde is reacted with piperazine as described in Step 2 of Example 29 and subsequently treated with hydrochloric acid as described in Example 44 to afford 1-(4-butylphenyl)-2-(piperazin-1-yl)-1H-indole-3-carboxaldehyde hydrochloride (46% yield) as a cream solid. ESI/MS 362 (M+H); RT=3.02 min; NMR 10.13 (1H, s); 8.12 (1H, d, J=9 Hz); 7.48 (4H, s); 7.21 (2H, m); 6.94 (1H, d, J=9 Hz); 3.41 (4H, br m); 2.97 (4H, br m); 2.74 (2H, t); 1.64 (2H, p); 1.37 (2H, m); 0.97 (3H, t).

Example 62

N-{3-[3-Formyl-2-(piperazin-1-yl)-indol-1-yl]phenyl}-acetamide Hydrochloride

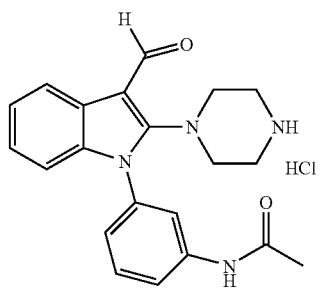

N-[3-(2-chloro-3-formyl-indol-1-yl)phenyl]-acetamide is reacted with piperazine as described in Step 2 of Example 29 and subsequently treated with hydrochloric acid as described in Example 44 to afford N-{3-[3-Formyl-2-(piperazin-1-yl)-indol-1-yl]phenyl}-acetamide hydrochloride (37% yield) as a cream solid. ESI/MS 363 (M+H); RT 2.2 min.

Example 63

4-[3-Formyl-2-(piperazin-1-yl)-indol-1-yl]-benzonitrile

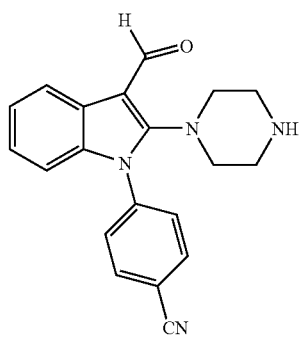

4-(2-chloro-3-formylindol-1-yl)-benzonitrile is reacted with piperazine as described in Step 2 of Example 29 to afford 4-[3-formyl-2-(piperazin-1-yl)-indol-1-yl]-benzonitrile as a light tan solid. ESI/MS 331 (M+H); NMR (CDCl$_3$) 10.35 (1H, s); 8.31 (1H, d, J=9 Hz); 7.92 (2H, d); 7.60 (2H, d); 7.31 (3H, m); 6.99 (1H, d, J=9 Hz); 3.28 (4H, m); 2.79 (4H, m).

Example 64

4-[3-Formyl-1-(4-iodophenyl)-1H-indol-2-yl]-piperazine-1-carboxylic Acid tert-Butyl Ester

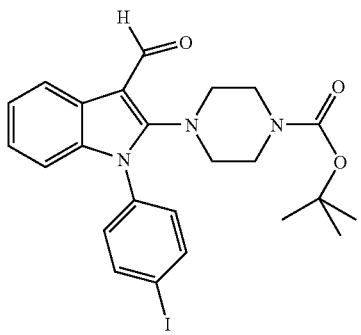

2-Chloro-1-(4-iodophenyl)-1H-indole-3-carboxaldehyde is reacted with piperazine as described in Step 2 of Example 29 to afford 4-[3-formyl-1-(4-iodophenyl)-1H-indol-2-yl]-piperazine-1-carboxylic acid tert-butyl ester (33% yield) as a light tan solid. TLC (heptane-30% ethyl acetate) $R_f$ 0.25; NMR (CDCl$_3$) 10.28 (1H, s); 8.26 (1H, d, J=9 Hz); 7.92 (2H, d, J=9 Hz); 7.26 (4H, m); 6.98 (1H, d, J=9 Hz); 3.36 (4H, m); 3.25 (4H, m); 1.46 (9H, s).

Example 65

4-[1-(4'-Cyanobiphenyl-4-yl)-3-formyl-1H-indol-2-yl]-piperazine-1-carboxylic Acid tert-Butyl Ester

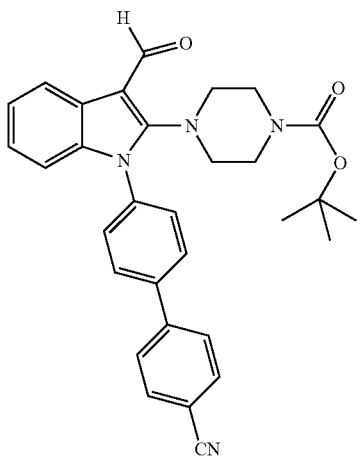

A mixture of 4-[3-formyl-1-(4-iodophenyl)-1H-indol-2-yl]-piperazine-1-carboxylic acid tert-butyl ester (294 mg, 0.553 mmol) and Pd(PPh$_3$)$_4$ (32 mg, 0.0277 mmol) are placed in a side-armed test tube and flushed with N$_2$. Tetrahydrofuran (6.0 mL) and 1M aq potassium carbonate (0.6 mL) are added followed by a solution of 4-cyanobenzeneboronic acid (122 mg, 0.830 mmol) in THF (2.0 mL). After stirring at 70° C. for 8 hr the reaction is cooled, then dissolved in ethyl acetate, washed with water (2×10 mL), with brine, dried over sodium sulfate, filtered and concentrated. The residue is purified by chromatography eluting with heptane-10 to 40% ethyl acetate. Product containing fractions are combined and concentrated to afford 4-[1-(4'-cyanobiphenyl-4-yl)-3-formyl-1H-indol-2-yl]-piperazine-1-carboxylic acid tert-butyl ester as a yellow solid. TLC (heptane-30% ethyl acetate); RT 0.13; ESI/MS 451 [M-C(CH$_3$)$_3$]; NMR (CDCl$_3$) 10.30 (1H, s); 8.28 (1H, d, J=9 Hz); 7.84 (6H, m); 7.55 (2H, d); 7.29 (3H, m); 3.34 (8H, m); 1.44 (9H, s).

Example 66

4-{1-[4-(tert-Butoxylcarbonyl-1H-pyrrol-2-yl)-phenyl]-3-formyl-1H-indol-2-yl}-piperazine-1-carboxylic Acid tert-Butyl Ester

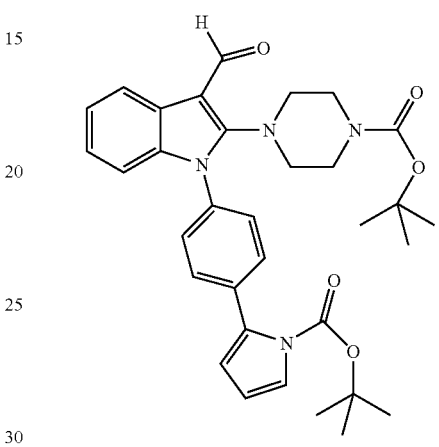

4-[3-Formyl-1-(4-iodophenyl)-1H-indol-2-yl]-piperazine-1-carboxylic acid tert-butyl ester is reacted with 1-(tert-butoxycarbonyl)pyrrole-2-boronic acid as described in Example 66 to afford 4-{1-[4-(tert-butoxylcarbonyl-1H-pyrrol-2-yl)-phenyl]-3-formyl-1H-indol-2-yl}-piperazine-1-carboxylic acid tert-butyl ester as a beige solid (56% yield). ESI/MS 571 (M+1), 515 [M-C(CH$_3$)$_3$]; NMR (CDCl$_3$) 10.28 (1H, s); 8.27 (1H, d, J=6 Hz); 7.59 (2H, d); 7.41 (6H, m); 6.32 (2H, m); 3.36 (8H, m); 1.46 (9H, s); 1.44 (9H, s).

Example 67

2-piperazin-1-yl-1-[(4-pyridin-4-yl)phenyl]-1H-indole-3-carboxaldehyde

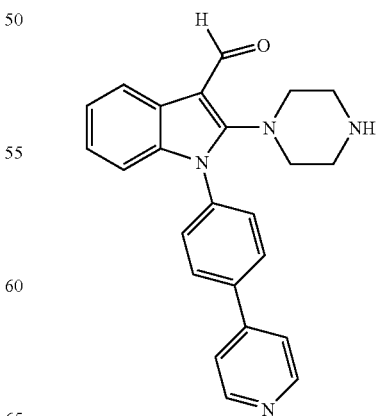

Step 1: 4-[3-Formyl-1-[(4-pyridin-4-yl)-phenyl]-1H-indol-2-yl]-piperazine-1-carboxylic acid tert-butyl ester:

4-[3-Formyl-1-(4-iodophenyl)-1H-indol-2-yl]-piperazine-1-carboxylic acid tert-butyl ester is reacted with 4-pyridylboronic acid as described in Example 65 to afford 4-[3-formyl-1-[(4-pyridin-4-yl)-phenyl]-1H-indol-2-yl]-piperazine-1-carboxylic acid tert-butyl ester (70% yield) as a yellow solid. ESI/MS 483 (M+1); NMR (CDCl$_3$) 10.30 (1H, s); 8.76 (2H, d); 8.28 (1H, d, J=6 Hz); 7.89 (2H, d, J=9 Hz); 7.64 (5H, m); 7.20 (2H, m); 3.36 (8H, m); 1.58 (9H, s).

Step 2: 2-piperazin-1-yl-1-[(4-pyridin-4-yl)phenyl]-1H-indole-3-carboxaldehyde:

4-[3-Formyl-1-[(4-pyridin-4-yl)phenyl]-1H-indol-2-yl]-piperazine-1-carboxylic acid tert-butyl ester (68 mg, 0.141 mmol) is dissolved in dichloromethane (1 mL), treated with trifluoroacetic acid (2 mL) and stirred for 2 hr at room temperature. The solvent is removed, the resulting oil is dissolved in water, made basic to pH around 7~8 with 20% aq sodium hydroxide and extracted with dichloromethane. The combined organic layer is washed with brine and dried over sodium sulfate, filtered and concentrated. The residue is purified by chromatography eluting with dichloromethane-0 to 10% methanol to afford 2-piperazin-1-yl-1-[(4-pyridin-4-yl)phenyl]-1H-indole-3-carboxaldehyde (46 mg, 85%) as a light tan solid. ESI/MS 383 (M+1).

Example 68

2-[1,4]Diazepan-1-yl-1-phenyl-1H-pyrrolo[2,3-b]pyridine-3-carbaldehyde; trifluoro-acetic acid salt

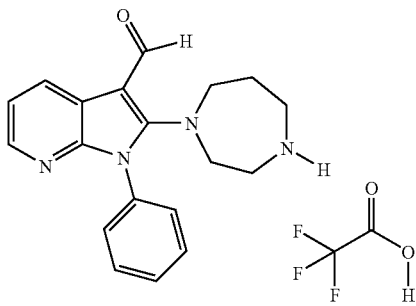

Step 1: 4-(3-Formyl-1-phenyl-1H-pyrrolo[2,3-b]pridin-2-yl)-[1,4]diazepane-1-carboxylic acid tert-butyl ester:

A solution of 2-chloro-1-phenyl-1H-pyrrolo[2,3-b]pyridine-3-carbaldehyde (210 mg, 0.818 mmol) in 1,4-dioxane (10 mL) is treated with [1,4]diazepane-1-carboxylic acid tert-butyl ester (0.80 mL, 4.11 mmol) and the resulting yellow solution is heated to 110° C. under a reflux condenser for 19.5 hours. The reaction mixture is evaporated to give an orange oil. The residue is purified by flash chromatography on a 10-gram silica gel cartridge by elution with dichloromethane, increasing to dichloromethane:methanol (99:1). Fractions containing the product are combined and the solvent evaporated to give 342 mg of 4-(3-formyl-1-phenyl-1H-pyrrolo[2,3-b]pyridin-2-yl)-[1,4]diazepane-1-carboxylic acid tert-butyl ester as a yellow orange glass (99.5% yield). MS: m/e 421 (M+H), 443 (M+Na), 365 (M-C$_4$H$_8$+H), 343(M-C$_5$H$_8$O$_2$+Na), 321(M-C$_5$H$_8$O$_2$+H). $^1$H NMR (300 MHz, CDCl$_3$): 10.23 (1H, s), 8.49 (1H, d), 8.22 (1H, dd), 7.64-7.48 (3H, m), 7.42 (2H, d), 7.19 (1H, dd), 3.50-3.29 (8H, m), 1.65-1.52 (2H, m), 1.44 (9H, s).

Step 2: 2-[1,4]Diazepan-1-yl-1-phenyl-1H-pyrrolo[2,3-b]pyridine-3-carbaldehyde; trifluoro-acetic acid salt:

A solution of 4-(3-formyl-1-phenyl-1H-pyrrolo[2,3-b]pyridin-2-yl)-[1,4]diazepane-1-carboxylic acid tert-butyl ester (330 mg, 0.786 mmol) in dichloromethane (20 mL) is treated with trifluoroacetic acid (0.60 mL, 6.04 mmol). The resulting solution is allowed to stir at room temperature for 22 hours before treating the reaction with a further aliquot of trifluoroacetic acid (0.60 mL, 6.04 mmol). After stirring for a further 18 hours, the reaction mixture is evaporated to give a gooey red oil. Trituration of the crude product salt with acetonitrile and ether gives 285 mg of 2-[1,4]diazepan-1-yl-1-phenyl-1H-pyrrolo[2,3-b]pyridine-3-carbaldehyde; trifluoro-acetic acid salt as a pink solid (84% yield). LC/MS: retention time 2.25 min, m/e 321 (M+H). $^1$H NMR (300 MHz, DMSO-d$_6$): 10.15 (1H, s), 8.60 (2H, br.s), 8.36 (1H, dd), 8.08 (1H, dd), 7.63-7.48 (5H, m), 7.22 (1H, dd), 3.63-3.48 (4H, m), 3.11-2.95 (4H, m), 1.81 (2H, m).

Example 69

2-Piperazin-1-yl-1-pyridin-3-yl-1H-pyrrolo[2,3-b]pyridine-3-carbaldehyde; bis-trifluoro-acetic acid salt

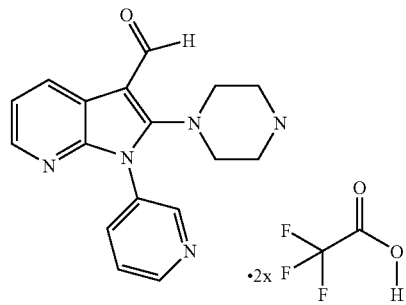

Step 1: 4-(3-Formyl-1-pyridin-3-yl-1H-pyrrolo[2,3-b]pyridin-2-yl)-piperazine-1-carboxylic acid tert-butyl ester:

A solution of 2-chloro-1-pyridin-3-yl-1H-pyrrolo[2,3-b]pyridine-3-carbaldehyde (46 mg, 0.179 mmol) in 1,4-dioxane (4 mL) is treated with piperazine-1-carboxylic acid tert-butyl ester (157 mg, 0.843 mmol) and the resulting yellow solution is heated-to 95° C. under a reflux condenser for 29 hours. The reaction mixture is evaporated to give a red oil. The residue is purified by flash chromatography on a 5-gram silica gel cartridge by elution with dichloromethane:ethyl acetate (3:1, increasing to 2:1 to 1:1). Fractions containing the product are combined and the solvent evaporated to give 62 mg of 4-(3-formyl-1-pyridin-3-yl-1H-pyrrolo[2,3-b]pyridin-2-yl)-piperazine-1-carboxylic acid tert-butyl ester as a orange waxy solid (85% yield). MS: m/e 408 (M+H), 430 (M+Na). $^1$H NMR (300 MHz, CDCl$_3$): 10.29 (1H, s), 8.78 (1H, d), 8.74 (1H, dd), 8.50 (1H, d), 8.20 (1H, dd), 7.94 (1H, dm), 7.59 (1H, dd), 7.22 (1H, dd), 3.39-3.28 (8H, m), 1.46 (9H, s).

Step 2: 2-piperazin-1-yl-1-pyridin-3-yl-1H-pyrrolo[2,3-b]pyridine-3-carbaldehyde; bis-trifluoro-acetic acid salt:

A solution of 4-(3-formyl-1-pyridin-3-yl-1H-pyrrolo[2,3-b]pyridin-2-yl)-piperazine-1-carboxylic acid tert-butyl ester (60 mg, 0.15 mmol) in dichloromethane (6 mL) is treated with trifluoroacetic acid (0.18 mL, 0.18 mmol). The resulting solution is allowed to stir at room temperature for 4 days to form a creamy suspension before treating the reaction with a further aliquot of trifluoroacetic acid (0.20 mL, 2.0 mmol) to give an orange solution. After stirring for a further 20 hours, the reaction mixture is evaporated to give an orange oil. Trituration of the crude product salt with acetonitrile and ether gives 54 mg of 2-piperazin-1-yl-1-pyridin-3-yl-1H-pyrrolo[2,3-b]pyridine-3-carbaldehyde; bis-trifluoro-acetic acid salt as a tan solid (68% yield). LC/MS: retention time 1.72 min, m/e 308 (M+H). $^1$H NMR (300 MHz, DMSO-d$_6$): 10.16 (1H, s), 8.86 (1H, d), 8.78 (2H, br.s), 8.74 (1H, d), 8.41 (1H, d), 8.17-8.13 (2H, m), 7.70 (1H, dd), 7.30 (1H, dd), 3.50-3.46 (4H, m), 3.06-3.00 (4H, m).

BIOLOGICAL EXAMPLES

Example 70

This Example illustrates the biological efficacy of the compounds of this invention in inhibiting the effects of PARP.

Cloning and Expression, and Partial Purification of Recombinant Human PARP:

Full length human PARP (PARP1) is assembled from PCR fragments of a clone from a human brain cDNA library and two Incyte clones. The PARP gene (3046 bp) is sub-cloned into pFastBac-HTb vector to give PARP-pFastBac-HTb and the sequence of this clone is verified. PARP-pFastBac-HTb is expressed to obtain protein using the Bac-to-Bac expression protocol from Gibco-BRL. The recombinant virus generated is used to scale up the material for purification.

Cell pellets from cell broth of cells expressing PARP are treated with a cocktail of protease inhibitors and lysed by 4 freeze-thaw cycles. The material is suspended in 10 mM HEPES/0.1M NaCl/pH 7.2, stirred, and then centrifuged. A 40%-70% ammonium sulfate cut of protein pellet is obtained from the supernatant. The pellet is solubilized in 10 mM HEPES/pH 7.2 and centrifuged. The supernatant buffer is exchanged to 10 mM HEPES/pH 7.2/0.1M NaCl/25% glycerol by dialysis or with a desalting column. The enzyme preparation is stored at −20° C. until use.

The compounds of this invention are then tested with this enzyme preparation using either the radioactive enzyme assay or by the "ELISA" enzyme assay as set forth below.

Radioactivity Enzyme Assay:

Incorporation of radioactivity from labeled NAD into acid-precipitated protein is measured. The reaction mixture (volume 100 µL or 50 µL, in a test-tube or 96-well plate) contained 100 µg/mL calf thymus DNA (sonicated), 100 µg/mL histones, 100 mM Tris (pH 8.0), 1.0 mM DTT, 10 mM MgCl$_2$, NAD (200 µM, 0.65 microcurie/mL), and varying amounts of enzyme. The reaction was incubated for 10 min at 37° C. or at room temperature for 60 min. The reaction was stopped and protein precipitated by addition of ice-cold trichloroacetic acid (TCA; 10% or 20% aqueous w/v). After brief storage in ice or at 4° C. for 2 hrs, the reaction mixture is filtered under vacuum through a glass fiber filter (2.5 cm disc, or 96-well filter plate). After washing with TCA and ethanol, the filter is dried and counted for tritium CPM after addition of scintillation fluid. 10 µL of a typical enzyme preparation of ~20 mg/mL protein gave 10,000 to 20,000 CPM in the 100 µL assay using filter disc, counted with 6 mL of EcoLume (ICN). Insect cells infected with wild-type virus gave no activity. The Km for NAD is established to be 111 µM (literature 50 to 100 µM). The compounds of this invention which are tested for inhibition are dissolved in water or DMSO and added to the assay to give a range of concentrations. A few of the reference compounds tested gave the following results: 3-Aminobenzamide inhibited the reaction with an IC$_{50}$ of 140 µM, nicotinamide gave IC$_{50}$~400 µM, and 1,5-isoquinolinediol gave IC$_{50}$ of 1 µM. Another literature standard DPQ gave IC$_{50}$ of 11 µM. The results obtained for the compounds of this invention are summarized in Table 3.

'ELISA' Enzyme Assay:

Incorporation of biotin-NAD into histone coated on plate is measured. A 96-well protein-binding EIA plate is coated with histone and blocked with bovine serum albumin. The reaction mixture (50 µL) contained DNA, buffer, enzyme, (test compound), and 250 µM of NAD and 5 µL of biotin-NAD (Trevigen). After reaction at room temperature the wells are washed and treated with Extravidin (Sigma). After incubation and washing color is developed with the peroxidase substrate TMB (Sigma). The TMB reaction is quenched with 2M sulfuric acid and the absorbance at 450 nm is read.

The IC$_{50}$ (fifty percent inhibitory concentration of the compound in a solution—expressed at micromolar (µM) concentration) measured in accordance with this procedure for the compounds of this invention is summarized in Table 3.

TABLE 3

| Example No. | IC$_{50}$ (µM) |
| --- | --- |
| Example 1 | 15.1 |
| Example 2 | 4.6 |
| Example 3 | 2.5 |
| Example 9 | 27.5 |
| Example 11B-1 | 2.5 |
| Example 11B-2 | 4.0 |
| Example 11B-3 | 4.5 |
| Example 11B-4 | 10.0 |
| Example 11B-5 | 3.0 |
| Example 11B-6 | 4.0 |
| Example 11B-7 | 4.0 |
| Example 11B-8 | 5.5 |
| Example 11B-9 | 4.0 |
| Example 11B-10 | 2.5 |
| Example 11B-11 | 3.0 |
| Example 12 | 2.0 |
| Example 13 | 3.0 |
| Example 19 | 8.8 |
| Example 21 | 5.1 |
| Example 22 | 4.5 |
| Example 41 | 43.1 |
| Example 43 | 11.4 |
| Example 45 | 5.1 |
| Example 46 | 0.85 |
| Example 47 | 6.9 |
| Example 48 | 15.5 |
| Example 49 | 1.9 |
| Example 50 | 1.4 |
| Example 51 | 26.0 |
| Example 52 | 42.2 |
| Example 53 | 19.9 |
| Example 54 | 3.1 |
| Example 55 | 4.1 |
| Example 56 | 1.5 |
| Example 57 | 1.4 |
| Example 58 | 0.85 |
| Example 61 | 2.7 |
| Example 62 | 0.99 |
| Example 63 | 2.3 |

Example 71

The following example illustrates the efficacy of the compounds of this invention in inhibiting the effects of PARP in a cell based assay.

Cell-Based Assay:

HL-60 (human leukemia) cells are grown and maintained using standard procedures in RPMI 1640+Glutamax medium supplemented with 10% fetal calf serum (FCS). For assay, cells are suspended in medium supplemented with 0.1% FCS at 0.5 million cells/mL and seeded into 96 well plates (100

μL/well). After preincubation for 3 hrs, cells are treated with compound for 1 hr, then Alamar Blue (Serotec) is added to the cells. After a further 24 hr incubation, fluorescence is measured (ex 560 nm, em 590 nm). Decrease in fluorescence compared to control cells (10 μM of a potent PARP inhibitor) is a measure of cell death. Increased fluorescence in the presence of test compound indicates protection from cell death induced by serum deprivation. For detection of poly-ADP-ribosylation, cells are subjected to serum deprivation in the presence and absence of compound. Cells are lysed and proteins are run on an SDS-PAGE gel. PolyADP-ribosylated proteins are detected with antibody to polyADP-ribose (Alexis or Calbiochem).

The results obtained from this study are expressed as $EC_{50}$ (median effective concentration of the test compound that was effective in preventing the cell death—expressed in micromolar (μM) concentration) for each of the tested compounds and are summarized in Table 4.

TABLE 4

| Example No. | EC50 (μM) |
| --- | --- |
| Example 2 | 3.4 |
| Example 3 | 1.9 |
| Example 9 | 8.0 |
| Example 12 | 3.0 |

Example 72

The following animal model is used to show the efficacy of the compounds of this invention in treating patients suffering from stroke.

Male Fisher 344 rats are anesthetized. The right carotid artery is isolated and ligated, and the right jugular vein is canulated for compound administration. The middle cerebral artery (MCA) was exposed through a craniotomy, and the MCA and its right branch, the lenticulostriate artery are electrocoagulated. The arteries are cut to avoid recanalization. The compounds of this invention (or standard DPQ) are administered i.v. 15 min after the MCA occlusion. The compounds are given as a 10 mg/kg bolus followed by an infusion of 5 mg/kg/hr for 6 hrs (total dose 40 mg/kg).

48 Hours post-MCA occlusion the rats are sacrificed, and the brains removed and cut into 2-mm coronal sections. The sections are incubated with triphenyltetrazolium chloride to demonstrate infarcted area, the extent and location of which is verified and quantified by image analysis.

The compound of Example 3 tested in this animal model showed the following results. A total dose of 40 mg/kg of 2-(piperazin-1-yl)-1-phenyl-1H-indole-3-carboxaldehyde (Example 3) is given as bolus plus infusion as described above. At this dose compound of Example 3 showed a significant (40-50%) reduction in infarct volume.

Example 73

This Example illustrates the efficacy of the compounds of the present invention in treating patients suffering from myocardial ischemia.

Male Sprague-Dawley rats are anesthetized and the chest is opened. A thin silk thread is placed around the left anterior descending coronary artery. The silk is passed through a plastic tube and the chest is closed. After stable hemodynamics, the coronary artery is occluded by applying tension to the thread via the tube. Successful occlusion is confirmed by a decrease in systolic blood pressure and alterations in ECG. Reperfusion is initiated by releasing the tension on the ligature.

For testing efficacy of Example 3 in this animal model, animals are divided into three groups. One group received the compound of Example 3 at 10 mg/kg i.v. 10 min prior to occlusion. A second group received compound of Example 3 at the same dose 5 min prior to reperfusion. The third group served as vehicle control. The period of occlusion is 20 min, followed by reperfusion for 60 min. After sacrifice infarct size is measured by staining of heart tissue slices with triphenyltetrazolium chloride and expressed as a percent (%) of area at risk.

A similar study is carried out with cariporide, a reference standard. The results indicated that when given prior to ischemia, both compounds showed significant protection. However, when given prior to reperfusion, cariporide showed no effect and compound of Example 3 showed a small but significant effect.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound, including enantiomers, stereoisomers, and tautomers of said compound and pharmaceutically acceptable salts solvates or derivatives thereof, with said compound having the general structure shown in formula (I):

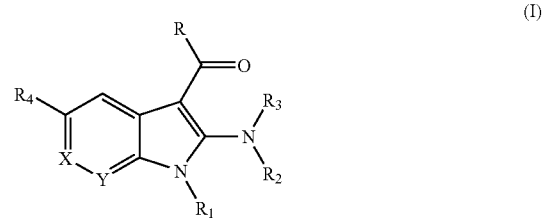

wherein
R is hydrogen, hydroxy, $C_{1-4}$alkoxy or amino;
$R_1$ is naphthyl, substituted phenyl, $C_{6-12}$aryl$C_{1-4}$alkyl, $C_{6-12}$arylsulfonyl or heteroaryl, and wherein said naphthyl, aryl or heteroaryl is optionally substituted with one or more substituents selected from the group consisting of halogen, $C_{1-6}$alkyl, $C_{1-6}$alkenyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$alkoxy, $C_{1-4}$thioalkyl, hydroxy, hydroxy$C_{1-4}$alkyl, $C_{1-4}$acyloxy, nitro, amino, $C_{1-4}$alkylamino, $C_{1-4}$dialkylamino, amino$C_{1-4}$alkyl, $C_{1-4}$alkylamino$C_{1-4}$ alkyl, $C_{1-4}$dialkylamino$C_{1-4}$alkyl, —CN, —$CO_2H$, —$CO_2C_{1-4}$ alkyl, —NHCO$C_{1-4}$alkyl, substituted or unsubstituted phenyl, substituted or unsubstituted phenoxy, substituted or unsubstituted benzyloxy, substituted or unsubstituted pyrrolyl and substituted or unsubstituted pyridyl;
$R_2$ and $R_3$ are the same or different and are each independently selected from: hydrogen, $C_{1-4}$alkyl, $C_{1-4}$dialkylamino$C_{1-4}$alkyl, pyrrolidinyl$C_{1-4}$alkyl, imidazolyl or heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of $C_{1-4}$alkyl, oxo, —CHO and —$CO_2C_{1-4}$alkyl; or R$_2$ and R$_3$ taken together with the nitrogen atom to which they are attached form an imidazolyl or a heterocycle selected from morpholinyl, thiomorpholinyl, aziridinyl, pyrrolidinyl, piperidinyl, azepanyl, piperazinyl, diazepanyl, diazabicyclo[2.2.1]hept-2-yl and triazocanyl; and wherein said heterocycle is optionally substituted with one or more substituents selected from the group consisting of C$_{1-4}$alkyl, oxo, —CHO, —CO$_2$C$_{1-4}$alkyl, hydroxyC$_{1-4}$alkyl, oxiranylC$_{1-4}$alkyl, dihydroxyC$_{1-4}$alkyl, —(CH$_2$)$_a$N—CO$_2$C$_{1-4}$alkyl, hydroxyl, and —(CH$_2$)$_a$OPO(OC$_{1-4}$alkyl)$_2$, wherein a is an integer from 1 to 4;

R$_4$ is C$_{1-4}$alkyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1, C$_{1-4}$alkoxy or C$_{1-4}$thioalkyl; and X and Y are CH.

2. The compound as set forth in claim 1, which is selected from the group consisting of:

2-(piperazin-1-yl)-1-(3-nitrophenyl)-1H-indole-3-carboxaldehyde,
2-(piperazin-1-yl)-1-(4-methoxyphenyl)-1H-indole-3-carboxaldehyde,
2-(piperazin-1-yl)-1-(4-tert-butylphenyl)-1H-indole-3-carboxaldehyde,
2-(piperazin-1-yl)-1-(4-bromophenyl)-1H-indole-3-carboxaldehyde,
2-(piperazin-1-yl)-1-(4-chlorophenyl)-1H-indole-3-carboxaldehyde,
2-(piperazin-1-yl)-1-(3-chloro-4-fluorophenyl)-1H-indole-3-carboxaldehyde,
2-(piperazin-1-yl)-1-(3-methoxyphenyl)-1H-indole-3-carboxaldehyde,
2-(piperazin-1-yl)-1-(4-thiomethylphenyl)-1H-indole-3-carboxaldehyde,
2-(piperazin-1-yl)-1-(3-fluorophenyl)-1H-indole-3-carboxaldehyde,
2-(piperazin-1-yl)-1-(3-methylphenyl)-1H-indole-3-carboxaldehyde,
1-(4-tert-butylphenyl)-2-piperazin-1-yl-1H-indole-3-carboxaldehyde,
1-(4-tert-butylphenyl)-2-piperidin-1-yl-1H-indole-3-carboxaldehyde,
1-(3-formylphenyl)-2-(piperazin-2-yl)-1H-indole-3-carboxaldehyde,
1-(biphenyl-4-yl)-2-(piperazin-1-yl)-1H-indole-3-carboxaldehyde hydrochloride,
1-(4-ethylphenyl)-2-(piperazin-1-y)-1H-indole-3-carboxaldehyde hydrochloride,
1-(3-bromophenyl)-2-piperazin-1-yl-1H-indole-3-carboxaldehyde,
1-(4-methyl-3-nitrophenyl)-2-(piperazin-1-yl)-1H-indole-3-carboxaldehyde,
1-(4-dimethylaminophenyl)-2-piperazin-1-yl-1H-indole-3-carboxaldehyde,
1-(4-phenoxyphenyl)-2-piperazin-1-yl-1H-indole-3-carboxaldehyde,
1-(4-methylphenyl)-2-(piperazin-1-yl)-1H-indole-3-carboxaldehyde,
1-(4-fluorophenyl)-2-(piperazin-1-yl)-1H-indole-3-carboxaldehyde hydrochloride,
1-(3-chlorophenyl-2-(piperazin-1-yl)-1H-indole-3-carboxaldehyde,
2-(piperazin-1-yl)-1-(4-vinylphenyl)-1H-indole-3-carboxaldehyde,
1-(3-hydroxymethylphenyl)-2-(piperazin-1-yl)-1H-indole-3-carboxaldehyde,
1-(3-ethoxyphenyl)-2-(piperazin-1-yl)-1H-indole-3-carboxaldehyde,
1-(4-butylphenyl)-2-(piperazin-1-yl)-1H-indole-3-carboxaldehyde hydrochloride,
N-{3-[3-formyl-2-(piperazin-1-yl)-indol-1-yl]phenyl}-acetamide hydrochloride,
4-[3-formyl-2-(piperazin-1-yl)-indol-1-yl]-benzonitrile, and
2-piperazin-1-yl-1-[(4-pyridin-4-yl)phenyl]-1H-indole-3-carboxaldehyde.

3. The compound as set forth in claim 1, which is selected from the group consisting of:

1-(4-tert-butylphenyl)-2-[4-(2-hydroxyethyl)piperazin-1-yl]-1H-indole-3-carboxaldehyde,
phosphoric acid 2-{4-[1-(4-tert-butylphenyl)-3-formyl-1H-indol-2-yl]-piperazin-1-yl}-ethyl ester diethyl ester hydrochloride,
1-(4-tert-butylphenyl)-2-(4-methyl-piperazin-1-yl)-1H-indole-3-carboxaldehyde,
4-[1-(4-tert-butylphenyl)-3-formyl-1H-indol-2-yl]piperazine-1-carboxylic acid tert-butyl ester,
5-[1-(4-tert-butylphenyl)-3-formyl-1H-indol-2-yl]-2,5-diazabicyclo[2.2.1]heptane-2-carboxylic acid tert-butyl ester,
1-(4-tert-butyl-phenyl)-2-(2-methyl-aziridin-1-yl)-1H-indole-3-carboxaldehyde,
4-[3-formyl-1-(4-iodophenyl)-1H-indol-2-yl]-piperazine-1-carboxylic acid tert-butyl ester,
4-[1-(4'-cyanobiphenyl-4-yl)-3-formyl-1H-indol-2-yl]-piperazine-1-carboxylic acid tert-butyl ester, and
4-{1-[4-(tert-butoxylcarbonyl-1H-pyrrol-2-yl)-phenyl]-3-formyl-1H-indol-2-yl}-piperazine-1-carboxylic acid tert-butyl ester.

4. The compound as set forth in claim 1, wherein R$_2$ and R$_3$ taken together with the nitrogen atom to which they are attached form imidazolyl.

5. The compound as set forth in claim 4, wherein said compound is 2-imidazol-1-yl-1-phenyl 1H-indole-3-carboxaldehyde.

6. The compound as set forth in claim 1, wherein R$_2$ is hydrogen or methyl, and R$_3$ is dimethylaminoethyl, pyrrolidinylethylamino, and piperidinyl.

7. The compound as set forth in claim 6, wherein said compound is selected from the group consisting of:

2-(2-dimethylaminoethylamino)-1-phenyl-1H-indole-3-carboxaldehyde,
2-[(methylpiperidin-4-yl)amino]-1-phenyl-1H-indole-3-carboxaldehyde,
1-(4-tert-butylphenyl)-2-[(2-dimethylaminoethyl)-methylamino]-1H-indole-3-carboxaldehyde,
1-(4-tert-butylphenyl)-2-(2-dimethylaminoethylamino)-1H-indole-3-carboxaldehyde, and
1-(4-tert-butylphenyl)-2-(2-pyrrolidin-1-yl-ethylamino)-1H-indole-3-carboxaldehyde hydrochloride.

8. The compound as set forth in claim 1, wherein R$_1$ is benzyl, naphthyl, thienyl, pyridinyl, and benzenesulfonyl.

9. The compound as set forth in claim 8, which is selected from the group consisting of:

2-(piperazin-1-yl)-1-benzyl-1H-indole-3-carboxaldehyde, 2-(piperazin-1-yl)-1-(1-naphthyl)-1H-indole-3-carboxaldehyde,
2-(piperazin-1-yl)-1-(thien-3-yl)-1H-indole-3-carboxaldehyde,
2-(piperazin-1-yl)-1-(pyridin-2-yl)-1H-indole-3-carboxaldehyde,
2-(piperazin-1-yl)-1-(pyridin-3-yl)-1H-indole-3-carboxaldehyde and
1-benzenesulfonyl-2-(piperazin-1-yl)-1H-indole-3-carboxaldehyde.

* * * * *